(12) United States Patent
Reddy et al.

(10) Patent No.: US 10,619,098 B2
(45) Date of Patent: Apr. 14, 2020

(54) ULTRAVIOLET LIGHT ABSORBERS

(71) Applicant: Transitions Optical, Inc., Pinellas Park, FL (US)

(72) Inventors: Ramaiahgari Reddy, Murrysville, PA (US); Cory S. Brown, Pittsburgh, PA (US); Alan Grubb, Pittsburgh, PA (US); Meng He, Palm Harbor, FL (US); Anil Kumar, Murrysville, PA (US); Ruisong Xu, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 15/514,004

(22) PCT Filed: Sep. 21, 2015

(86) PCT No.: PCT/US2015/051201
§ 371 (c)(1),
(2) Date: Mar. 24, 2017

(87) PCT Pub. No.: WO2016/053662
PCT Pub. Date: Apr. 7, 2016

(65) Prior Publication Data
US 2017/0275534 A1    Sep. 28, 2017

Related U.S. Application Data

(60) Provisional application No. 62/057,305, filed on Sep. 30, 2014.

(51) Int. Cl.
| | | |
|---|---|---|
| *C09K 19/54* | (2006.01) | |
| *C07C 233/56* | (2006.01) | |
| *C07D 239/74* | (2006.01) | |
| *C07D 249/20* | (2006.01) | |
| *C07D 277/66* | (2006.01) | |
| *C09K 19/02* | (2006.01) | |
| *A61F 2/16* | (2006.01) | |
| *C07D 249/22* | (2006.01) | |
| *C07D 263/60* | (2006.01) | |
| *C07D 277/84* | (2006.01) | |
| *C07D 213/30* | (2006.01) | |
| *C07D 235/18* | (2006.01) | |
| *C07D 263/57* | (2006.01) | |
| *C09K 19/60* | (2006.01) | |

(52) U.S. Cl.
CPC ............ *C09K 19/54* (2013.01); *A61F 2/1659* (2013.01); *C07C 233/56* (2013.01); *C07D 213/30* (2013.01); *C07D 235/18* (2013.01); *C07D 239/74* (2013.01); *C07D 249/20* (2013.01); *C07D 249/22* (2013.01); *C07D 263/57* (2013.01); *C07D 263/60* (2013.01); *C07D 277/66* (2013.01); *C07D 277/84* (2013.01); *C09K 19/02* (2013.01); *C09K 19/60* (2013.01); *A61F 2002/16965* (2015.04); *C07C 2601/14* (2017.05)

(58) Field of Classification Search
None
See application file for complete search history.

(56) References Cited

U.S. PATENT DOCUMENTS

| | | | | |
|---|---|---|---|---|
| 3,113,940 A | * | 12/1963 | Di Pietro ............ | C08K 5/3492 44/336 |
| 3,238,138 A | | 3/1966 | Braunwarth et al. | |
| 3,676,471 A | * | 7/1972 | Eggensperger ......... | C07C 49/84 524/291 |
| 3,808,278 A | * | 4/1974 | Hofer ..................... | C07C 45/46 568/333 |
| 3,988,295 A | | 10/1976 | Irick, Jr. et al. | |
| 4,029,670 A | | 6/1977 | Pond et al. | |
| 4,853,471 A | * | 8/1989 | Rody ................... | C07D 249/20 548/261 |
| 4,859,725 A | * | 8/1989 | Avar .................... | C07D 249/20 524/91 |
| 5,021,478 A | * | 6/1991 | Ravichandran ...... | C07D 211/94 524/100 |
| 5,280,124 A | * | 1/1994 | Winter ................. | C07D 249/20 548/259 |
| 5,292,890 A | * | 3/1994 | Moshchitsky ....... | C07D 249/20 548/259 |
| 5,298,652 A | * | 3/1994 | Carson ................. | C07C 235/52 554/105 |
| 5,362,881 A | * | 11/1994 | Leistner .............. | C07D 249/20 548/259 |

(Continued)

FOREIGN PATENT DOCUMENTS

| | | | |
|---|---|---|---|
| CN | 1243701 A | | 2/2000 |
| CN | 101298442 A | * | 11/2008 |

(Continued)

OTHER PUBLICATIONS

English translation of JP2008242179. (Year: 2008).*

(Continued)

*Primary Examiner* — Cynthia H Kelly
*Assistant Examiner* — Anna Malloy
(74) *Attorney, Agent, or Firm* — The Webb Law Firm

(57) ABSTRACT

Compounds that have ultraviolet light absorbing properties, and which can also have mesogenic properties. Compositions that include one or more such compounds. Articles of manufacture that include one or more such compounds, such as optical elements that include an optical substrate and a layer that includes at least one such compound.

23 Claims, No Drawings

(56) References Cited

U.S. PATENT DOCUMENTS

| | | | |
|---|---|---|---|
| 6,060,042 A | | 5/2000 | Schuhmacher et al. |
| 6,143,888 A | * | 11/2000 | Rohringer ............ C07D 251/42 |
| | | | 252/301.23 |
| 6,696,114 B1 | * | 2/2004 | Kawatsuki ........ G02F 1/133711 |
| | | | 349/123 |
| 2002/0111404 A1 | | 8/2002 | Wood et al. |
| 2006/0280882 A1 | | 12/2006 | Oka et al. |
| 2009/0108733 A1 | * | 4/2009 | Chin .................. H01L 51/0092 |
| | | | 313/504 |
| 2010/0129698 A1 | * | 5/2010 | Okada ................. B01J 31/1805 |
| | | | 429/523 |
| 2010/0213423 A1 | | 8/2010 | Shiau et al. |
| 2011/0059867 A1 | * | 3/2011 | Kim ...................... C07C 233/20 |
| | | | 506/16 |
| 2012/0021144 A1 | | 1/2012 | Dai et al. |
| 2012/0021244 A1 | * | 1/2012 | Chang ................. B23K 11/004 |
| | | | 428/621 |
| 2013/0289105 A1 | * | 10/2013 | Vasioukhin ............ A61K 31/40 |
| | | | 514/468 |
| 2013/0306909 A1 | * | 11/2013 | Goto .................. C09K 19/3003 |
| | | | 252/299.63 |
| 2016/0137646 A1 | * | 5/2016 | Ong ..................... C07D 487/04 |
| | | | 514/248 |

FOREIGN PATENT DOCUMENTS

| | | | | |
|---|---|---|---|---|
| EP | 2261279 A1 | | 12/2010 | |
| GB | 1212466 A | * | 11/1970 | ............ C07C 45/71 |
| GB | 2315073 A | | 1/1998 | |
| JP | 5512586 B2 | | 2/1980 | |
| JP | 56125721 A | | 10/1981 | |
| JP | 05194931 A | * | 8/1993 | .......... D06M 13/352 |
| JP | 2006241199 A | | 9/2006 | |
| JP | 2008242179 A | * | 10/2008 | |
| WO | 2003018682 A1 | | 3/2003 | |

OTHER PUBLICATIONS

English translation of CN101298442. (Year: 2008).*
English translation of JP05194931. (Year: 1993).*
Lopez-Ruiz, et al., Phenylboronic acid catalyzed-cyanide promoted, one-pot synthesis of 2-(2-hydroxyphenyl)benzoxazole derivatives, Jun. 17, 2011, Tetrahedron Letters, 52, 4308-4312. (Year: 2011).*
Oliveira et al., On the use of 2,1,3-benzothiadiazole derivatives as selective live cell fluorescence imaging probes, Aug. 20, 2010, Bioorganic & Medicinal Chemistry Letters, 20, 6001-6007. (Year: 2010).*

\* cited by examiner

ULTRAVIOLET LIGHT ABSORBERS

CROSS-REFERENCE TO RELATED APPLICATIONS

This application is the United States national phase of International Application No. PCT/US2015/051201 filed Sep. 21, 2015, and claims priority to U.S. Provisional Patent Application No. 62/057,305 filed Sep. 30, 2014, the disclosures of which are hereby incorporated in their entirety by reference.

FIELD

The present invention relates to compounds that have ultraviolet light absorbing properties, and which can also have mesogenic properties.

BACKGROUND

The molecules of a liquid crystal can align with one another in substantially one direction, which results in a fluid material having one or more anisotropic properties, such as anisotropic optical, electromagnetic, and/or mechanical properties. A mesogen is typically described as the primary or fundamental unit (or segment or group) of a liquid crystal material that induces, and/or is induced into, structural order amongst and between liquid crystals (e.g., other liquid crystal materials that are present).

Liquid crystal polymers are polymers capable of forming regions of highly ordered structure while in a liquid phase. Liquid crystal polymers have a wide range of uses, including engineering plastics, and gels for LC displays. The structure of liquid crystal polymers is typically composed of densely packed fibrous polymer chains that provide self-reinforcement almost to the melting point of the polymer.

Dichroism can occur in liquid crystals due to the optical anisotropy of the molecular structure, or the presence of impurities, or the presence of dichroic dyes. Dichroic materials typically have the ability to absorb one of two orthogonal plane polarized components of radiation (e.g., transmitted and/or reflected radiation) more strongly than the other orthogonal plane polarized component.

Linearly polarizing elements, such as linearly polarizing lenses for sunglasses and linearly polarizing filters, are typically formed from orientated, such as unilaterally orientated, polymer sheets containing a dichroic material, such as a static dichroic dye. Consequently, conventional linearly polarizing elements are static elements having a single, linearly polarizing state. Accordingly, when a conventional linearly polarizing element is exposed to either randomly polarized radiation or reflected radiation of the appropriate wavelength, some percentage of the radiation transmitted through the element is linearly polarized. Linearly polarized electromagnetic radiation, such as visible light, have the vibrations of the electromagnetic vector of light waves thereof confined or effectively limited to one direction or plane.

In addition, conventional linearly polarizing elements are often tinted. For example, conventional linearly polarizing elements can contain a coloring agent, such as a static dichroic dye, and correspondingly have an absorption spectrum that does not vary in response to actinic radiation. The color of conventional linearly polarizing elements typically depends upon the coloring agent present in the element, and is often a neutral color (e.g., brown or gray). As such, while conventional linearly polarizing elements are useful in reducing glare associated with reflected light, they are not, however, well suited for use under certain low-light conditions, because of the static coloring agent. In addition, because conventional linearly polarizing elements have only a single, tinted linearly polarizing state, they are limited in their ability to store or display information.

As discussed above, conventional linearly polarizing elements are typically formed using sheets of orientated polymer films containing a dichroic material. Thus, while dichroic materials are capable of selectively absorbing one of two orthogonal plane polarized components of transmitted radiation, if the molecules of the dichroic material are not suitably positioned or aligned, no net linear polarization of transmitted radiation will be achieved. Due to the random positioning of the molecules of the dichroic material, selective absorption by the individual molecules will cancel each other such that no net or overall linear polarizing effect is achieved. As such, suitable positioning of the molecules of the dichroic material is typically achieved by alignment thereof with another material, which results in a net linear polarization.

In contrast to the dichroic elements discussed above, conventional photochromic elements, such as photochromic lenses that are formed using conventional thermally reversible photochromic materials, are generally capable of converting from a first state, for example, a "clear state," to a second state, for example, a "colored state," in response to exposure to actinic radiation, and then reverting back to the first state in response to, actinic radiation, such as the absence or reduction of exposure to actinic radiation, and/or thermal energy. As such, conventional photochromic elements are generally well suited for use in both low-light conditions and bright conditions. Conventional photochromic elements, however, that do not include linearly polarizing filters are generally not adapted to linearly polarize radiation. That is, the absorption ratio of conventional photochromic elements, in either state (e.g., clear state and/or colored state), is generally less than two. Therefore, conventional photochromic elements are not capable of reducing glare associated with reflected light to the same extent as conventional linearly polarizing elements. To address this deficiency, photochromic-dichroic materials have been developed. Photochromic-dichroic materials provide both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

Photochromic materials and photochromic-dichroic materials can be incorporated into a substrate or an organic material, for example a polymer substrate, including liquid crystal polymer substrates. When photochromic materials and photochromic-dichroic materials undergo a change from one state to another (e.g., from a clear state to a colored state), the molecule(s) of the photochromic compound or photochromic-dichroic compound typically undergo a conformational change from a first conformational state to a second conformational state. This conformational change can result in a change in the amount of physical space that the compound occupies. For certain photochromic materials and certain photochromic-dichroic materials, however, to effectively transition from one state to another state (e.g., to transition from a clear state to a colored state, or to transition from a colored state to a clear state, and/or to transition from a non-polarized state to a polarized state, or to transition from a polarized state to a non-polarized state) the photochromic compound or photochromic-dichroic compound typically requires a chemical environment that is sufficiently flexible to allow the compound to transition from a first conformational state to a second conformational state at a rate that is at least sufficient to provide the desired response on over an acceptable time frame. Liquid crystal polymers can provide such a sufficiently flexible environment.

Organic materials, such as polymers and/or liquid crystal polymers, typically include stabilizers, such as thermal stabilizers and/or ultraviolet light stabilizers, to limit and/or delay degradation of the organic material due to exposure to elevated temperatures and/or ultraviolet light. The presence of stabilizers in organic materials containing dichroic materials, such as photochromic-dichroic materials, can disrupt alignment of the dichroic materials, resulting in an undesirable reduction in absorption ratio values. Alternatively or additionally, when the organic material is composed of or contains liquid crystal materials, such as liquid crystal polymers, the presence of stabilizers can undesirably disrupt alignment of the liquid crystal materials. Still further alternatively or additionally, to disrupting liquid crystal alignment, the stabilizers may not be sufficiently soluble in the liquid crystal material, such as a liquid crystal polymer matrix, resulting in an undesirable reduction in clarity (e.g., an increase in haze) of the material.

It would be desirable to develop new stabilizers that can be used in compositions containing liquid crystal materials. In addition, it would be desirable that such newly developed stabilizers minimize or result in no disruption of liquid crystal alignment and/or have improved solubility in compositions containing liquid crystal materials. It would be further desirable that such newly developed stabilizers enhance liquid crystal alignment in compositions containing liquid crystal materials.

SUMMARY

In accordance with the present invention, there is provided a compound represented by at least one of the following Formulas (I), (II), (III), (IV), (V), (VI), (VII), (VIII), and (IX),

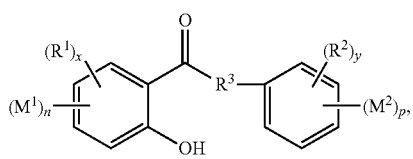
(I)

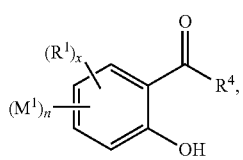
(II)

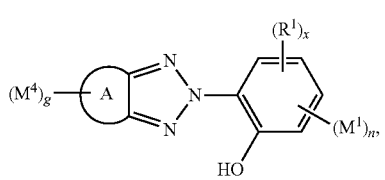
(III)

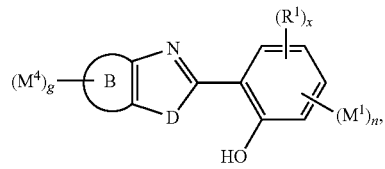
(IV)

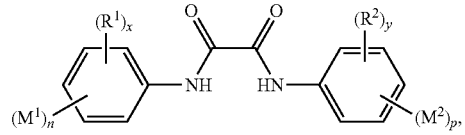
(V)

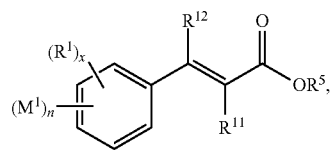
(VI)

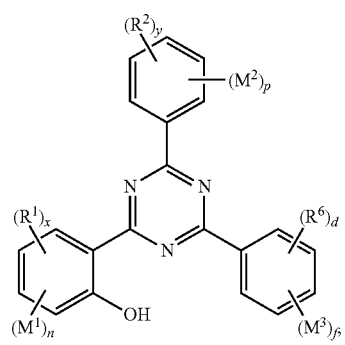
(VII)

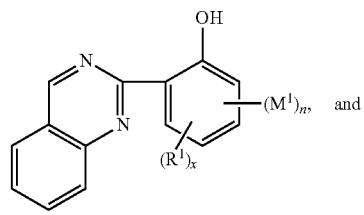
(VIII) and

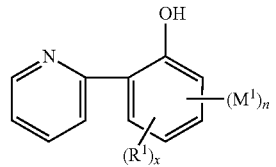
(IX)

Independently for each of Formulas (I), (II), (III), (IV), (V), (VI), (VII), (VIII), and (IX), $R^1$ independently for each x, $R^2$ independently for each y, and $R^6$ independently for each d, are in each case independently selected from the group consisting of hydrogen, hydrocarbyl, substituted hydrocarbyl, and —$OR^7$, where each $R^7$ is independently selected from the group consisting of hydrogen, hydrocarbyl, and substituted hydrocarbyl, wherein the hydrocarbyl and substituted hydrocarbyl of $R^1$, $R^2$, $R^6$, and $R^7$ are in each case independently and optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from the group consisting of hydrogen, hydrocarbyl and substituted hydrocarbyl.

Further independently for each of Formulas (I), (II), (III), (IV), (V), (VI), (VII), (VIII), and (IX), $M^1$ independently for each n, $M^2$ independently for each p, $M^3$ independently for each f, and $M^4$ independently for each g, are in each case independently represented by the following Formula (X),

 (X)

Independently for each Formula (X), $L^1$ in each case is independently selected from the group consisting of at least one of: a single bond; —O—; —S—; —C(O)—; —S(O)—; —SO$_2$—; —N=N—; —N($R_{11}$')— where $R_{11}$' is selected from hydrogen, hydrocarbyl or substituted hydrocarbyl; —Si(O$R_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl; hydrocarbyl, and substituted hydrocarbyl, each optionally and independently interrupted with at least one of —O—, —S—, —C(O)—, —C(O)O—, —S(O)—, —SO$_2$—, —N=N—, —N($R_{11}$')— where $R_{11}$' is selected from the group consisting of hydrogen, hydrocarbyl or substituted hydrocarbyl, —Si(O$R_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl, and combinations of two or more thereof.

With further reference to Formula (X), and independently for each Formula (X), t is 1 to 4, and m is, independently for each t, from 0 to 8.

With further reference to Formula (X), and independently for each Formula (X), $L^2$ is independently for each m selected from the group consisting of divalent linear or branched $C_1$-$C_{25}$ alkyl, divalent linear or branched $C_1$-$C_{25}$ perhaloalkyl, and divalent linear or branched $C_2$-$C_{25}$ alkenyl, in each case optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from the group consisting of hydrogen, hydrocarbyl and substituted hydrocarbyl.

With continued reference to Formula (X), and independently for each Formula (X), q is, independently for each t, from 0 to 8, provided that the sum of m and q is at least one for each t, and provided that q is at least 1 for at least one t.

With additional reference to Formula (X), and independently for each Formula (X), $L^3$ independently for each q is represented by the following Formula (XI-1),

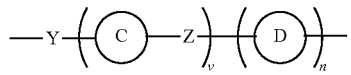 Formula (XI-1)

With reference to Formula (XI-1), Y is, independently for each q, a divalent linking group selected from the group consisting of a single bond, —O—, —S—, —C(O)—, —C(O)O—, —OC(O)O—, —S(O)—, —SO$_2$—, —N($R^9$)—, —N($R^9$)—C(O)—O—, —C(O)—N($R^9$)—, and —Si($R^9$)($R^{10}$)— wherein $R^9$ and $R^{10}$ are each independently selected from the group consisting of hydrogen, hydrocarbyl and substituted hydrocarbyl.

With further reference to Formula (XI-1), v and u are each independently, for each q, selected from 0 to 5, provided that the sum of v and u is at least 2 for each q that is greater than zero.

With additional reference to Formula (XI-1), Z is, independently for each v, a divalent linking group selected from the group consisting of a single bond, —O—, —S—, —C(O)—, —C(O)O—, —OC(O)O—, —S(O)—, —SO$_2$—, —N($R^9$)—, —N($R^9$)—C(O)—O—, —C(O)—N($R^9$)—, and —Si($R^9$)($R^{10}$)— wherein $R^9$ and $R^{10}$ are each independently selected from the group consisting of hydrogen, hydrocarbyl and substituted hydrocarbyl.

With continued reference to Formula (XI-1), the divalent rings,

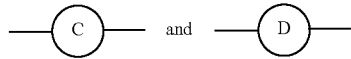

are each independently selected, for each v and each u, from the group consisting of divalent aryl, substituted divalent aryl, divalent heteroaryl, substituted divalent heteroaryl, divalent cycloalkyl, substituted divalent cycloalkyl, divalent heterocycloalkyl, and substituted divalent heterocycloalkyl.

With reference to Formula (X), $E^1$ is selected from the group consisting of: hydrogen; hydrocarbyl; substituted hydrocarbyl, where the hydrocarbyl and substituted hydrocarbyl are each optionally and independently interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from the group consisting of hydrogen, hydrocarbyl and substituted hydrocarbyl; and (meth)acryloyl.

With further reference to Formula (X), there are the following provisos: a direct $L^1$-$L^2$ link between $L^1$ and $L^2$ is free of two heteroatoms linked together; a direct $L^1$-$L^3$ link between $L^1$ and $L^3$ is free of two heteroatoms linked together; and each direct $L^2$-$L^3$ link between each directly linked $L^2$ and $L^3$ is free of two heteroatoms linked together.

With reference to Formula (I): $R^3$ is a single bond or —CH$_2$—; x is from 0 to 4; n is from 0 to 4, provided that the sum of x and n is 4; y is from 0 to 5; and p is from 0 to 5, provided that the sum of y and p is 5. With further reference to Formula (I), there are the following provisos: the sum of n and p is at least 1; $M^1$ and $M^2$ are each free of a terminal -$L^3$-$E^1$ group in which $L^3$ and/or $E^1$ comprise a hydroxyl substituted aryl group; and $M^1$ and $M^2$ are each free of a terminal -$L^2$-$E^1$ group in which $E^1$ comprises a hydroxyl substituted aryl group.

With reference to Formula (II): x is from 0 to 3; n is from 1 to 4, provided that the sum of x and n is 4; and $R^4$ is selected from the group consisting of hydrogen, hydrocarbyl, substituted hydrocarbyl, heteroaryl, substituted heteroaryl, —O$R^8$, and $M^2$, where $R^8$ is selected from the group consisting of hydrogen, hydrocarbyl, and substituted hydrocarbyl.

With reference to Formula (III): x is from 0 to 4; n is from 0 to 4, provided that the sum of x and n is 4; g is from 0 to 6, provided that the sum of n and g is at least 1; and Ring-A is selected from the group consisting of aryl, substituted aryl, heteroaryl, and substituted heteroaryl.

With reference to Formula (IV): x is from 0 to 4; n is from 1 to 4, provided that the sum of x and n is 4; g is from 0 to 6, provided that the sum of n and g is at least 1; Ring-B is selected from the group consisting of aryl, substituted aryl, heteroaryl, and substituted heteroaryl; and D is selected from the group consisting of O, S, and N—$R_2$', wherein $R_2$' is selected from the group consisting of hydrogen, hydrocarbyl, and substituted hydrocarbyl, each optionally and independently interrupted with at least one of —O—, —S—, —C(O)—, —C(O)O—, —S(O)—, —SO$_2$—, —N=N—, —N(R$_{11}$')— where R$_{11}$' is selected from the group consisting of hydrogen, hydrocarbyl or substituted hydrocarbyl, —Si(OR$_8$')$_w$(R$_8$')$_e$—, where w and e are each independently 0 to 2, provided that the sum of w and e is 2, and each R$_8$' is independently selected from the group consisting of hydrogen, hydrocarbyl and substituted hydrocarbyl, and combinations of two or more thereof.

With reference to Formula (V): x is from 0 to 5; n is from 0 to 5, provided the sum of x and n is 5; y is from 0 to 5; and p is from 0 to 5, provided the sum of y and p is 5. With further reference to Formula (V), there is the proviso that the sum of n and p is at least 1.

With reference to Formula (VI): x is from 0 to 5; n is from 0 to 5, provided the sum of x and n is 5; R$^5$ is selected from the group consisting of hydrogen, hydrocarbyl, substituted hydrocarbyl, and M$^2$; and R$^{11}$ and R$^{12}$ are each independently selected from the group consisting of hydrogen, —CN, —C(O)OR$^{13}$, hydrocarbyl, and substituted hydrocarbyl, where R$^{13}$ is selected from the group consisting of hydrogen, hydrocarbyl, and substituted hydrocarbyl. With further reference to Formula (VI), there is the proviso that, n is at least 1 and/or R$^5$ is M$^2$.

With reference to Formula (VII): x is from 0 to 4; n is from 0 to 4, provided that the sum of x and n is 4; y is from 0 to 5; p is from 0 to 5, provided that the sum of y and p is 5; d is from 0 to 5; and f is from 0 to 5, provided that the sum of d and f is 5. With further reference to Formula (VII), there is the proviso that the sum of n, p, and f is at least 1.

With reference to Formula (VII): x is from 0 to 3; and n is from 1 to 4, provided that the sum of x and n is 4.

With reference to Formula (IX): x is from 0 to 3; and n is from 1 to 4, provided that the sum of x and n is 4.

In accordance with the present invention, there is further provided a composition that comprises one or more to the compounds described above.

In accordance with the present invention, there is additionally provided an article of manufacture that comprises one or more to the compounds described above.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

DETAILED DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

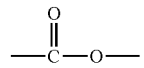

or equivalently —C(O)O—, is inclusive of the right-to-left representation thereof,

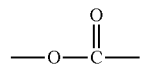

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth) acrylic acid" means methacrylic acid and/or acrylic acid. As used herein, the term "(meth)acryloyl" means acryloyl and/or methacryloyl.

The compounds of the present invention, as described herein, including, but not limited to, compounds represented by Formulas (I), (II), (III), (IV), (V), (VI), (VII), (VIII), and (IX), in each case can optionally and independently further include one or more coproducts, resulting from the synthesis of such compounds.

As used herein, the term "mesogen" and related terms, such as "mesogenic," such as used in conjunction with the compounds of the present invention represented by Formulas (I), (II), (III), (IV), (V), (VI), (VII), (VIII), and (IX), means a compound and/or group that induces, and/or is induced into, structural order amongst and between: (i) other such compounds and/or groups; and/or (ii) other liquid crystal materials that are present therewith.

As used herein, the term "dichroic," and similar terms, such as "dichroism," means the ability to absorb one of two orthogonal plane polarized components of radiation, such as transmitted and/or reflected radiation, more strongly than the other orthogonal plane polarized component.

As used herein, the term "linearly polarized" and similar terms, such as "linear polarization" and "plane polarization," means to confine, or effectively limit, the electric field vector or magnetic field vector of electromagnetic radiation to a given plane along the direction of propagation.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, photochromic compounds can have a different absorption spectrum in each of the first and second state. For example, while not limiting herein, a photochromic compound can be clear in the first state and colored in the second state. Alternatively, a photochromic compound can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R_{11}$')($R_{12}$') where $R_{11}$' and $R_{12}$' are each independently selected, with some embodiments, from hydrogen, linear or branched $C_1$-$C_{20}$ alkyl, $C_3$-$C_{12}$ cycloalkyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F.

The compounds of the present invention, such as represented by Formulas (I), (II), (III), (IV), (V), (VI), (VII), (VIII), and/or (IX), include, with some embodiments, groups and sub-groups that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —$N(R_{11}')(R_{12}')$ where $R_{11}'$ and $R_{12}'$ are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and/or iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, with some embodiments, can in each case be independently and optionally interrupted with at least one of —O—, —S—, —C(O)—, —C(O)O—, —S(O)—, —$SO_2$—, —N═N—, —$N(R_{11}')$— where $R_{11}'$ is selected from hydrogen, hydrocarbyl or substituted hydrocarbyl, —$Si(OR_8')_w(R_8')_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof. As used herein, by interrupted with at least one of —O—, —S—, —C(O)—, —C(O)O—, —OC(O)O—, —S(O)—, —$SO_2$—, —N═N—, —$N(R_{11}')$—, and —$Si(OR_8')_w(R^8)_t$—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —$N(R_{11}')$— can provide a divalent amide linking or interrupting group, —C(O)—$N(R_{11}')$—. For purposes of further non-limiting illustration, a combination of adjacent —$N(R_{11}')$—, —C(O)— and —O— can provide a divalent carbamate (or urethane) linking or interrupting group, —$N(R_{11}')$—C(O)—O—, where $R_{11}'$ is hydrogen. A combination of —O—, —C(O)— and —O— can provide a divalent carbonate linking or interrupting group, —O—C(O)—O—, with some embodiments. A combination of —O— and —C(O)— can provide a divalent carboxylic acid ester linking or interrupting group, —O—C(O)—, with some embodiments. A combination of —$N(R_{11}')$—, —C(O)—, and —$N(R_{11}')$— can provide a divalent urea linking or interrupting group, —$N(R_{11}')$—C(O)—$N(R_{11}')$—, with some embodiments.

The term "optionally interrupted with" as used with regard to the various groups described herein, such as but not limited to hydrocarbyl and substituted hydrocarbyl groups, also includes interruption at one or more terminal linking positions of the group, where the group is linked to another group. The term "terminal linking position" includes an initial linking position where the group is linked to the compound or core compound structure with at least one of —O—, —S—, —C(O)—, —C(O)O—, —S(O)—, —$SO_2$—, —N═N—, —C(O)—$N(R_{11}')$—, —$N(R_{11}')$— where $R_{11}'$ is selected from hydrogen, hydrocarbyl or substituted hydrocarbyl, —$Si(OR_8')_w(R_8')_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof. For purposes of nonlimiting illustration, and with reference to Formula (I), when subscript x is at least 1 and an $R^1$ of Formula (I) is hydrocarbyl, the $R^1$ hydrocarbyl group can be interrupted with one or more of the above recited divalent interrupting groups, such as but not limited to —O—: (i) along the hydrocarbyl chain thereof; and/or (ii) at the point (i.e., at the initial linking position) where $R^1$ is bonded to the hydroxyl substituted and optionally $M^1$ substituted phenyl ring of the compound represented by Formula (I). For purposes of further non-limiting illustration with regard to terminal linking positions that can include one or more divalent linking groups as described above (such as —O—, —S—, etc.), and with reference to Formula (X) which is described further herein: a terminal linking position of $L_2$, where $L_2$ is linked to $L_3$, can be optionally interrupted with one or more of the divalent linking groups described above; a terminal linking position of $L_3$, where $L_3$ is linked to $L_2$, can be optionally interrupted with one or more of the divalent linking groups described above; a terminal linking position of $L_2$, where $L_2$ is linked to $E_1$, can be optionally interrupted with one or more of the divalent linking groups described above; and/or a terminal linking position of $L_3$, where $L_3$ is linked to $E_1$, can be optionally interrupted with one or more of the divalent linking groups described above.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH═CH— groups and/or one or more —C≡C— groups. With some embodiments, the alkyl groups are free of two or more conjugated unsaturated linkages. With some further embodiments, the alkyl groups are free of unsaturated linkages, such as —CH═CH— groups and —C≡C— groups.

The term "cycloalkyl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo [2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo [2.2.1]heptanyl; and fused ring polycyclic heterocycloalkyl groups, such as but not limited to, octahydrocyclopenta[b] pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The compounds according to the present invention, such as, but not limited to those represented by Formulas (I), (II), (III), (IV), (V), (VI), (VII), (VIII), and (IX), and the various groups thereof are described in further detail herein as follows.

In accordance with some embodiments, independently for each of Formulas (I), (II), (III), (IV), (V), (VI), (VII), (VIII), and (IX), $R^1$ independently for each x, $R^2$ independently for each y, and $R^6$ independently for each d, are in each case independently selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, heteroaryl, and —$OR^7$, where each $R^7$ is independently selected from the group consisting of hydrogen, $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

Independently for each Formula (X), and in accordance with some embodiments, and independently for each $M^1$, independently for each $M^2$, independently for each $M^3$, and independently for each $M^4$: m is at least 1 for at least one t; and $L^2$, independently for each m, is selected from the group consisting of divalent linear or branched $C_1$-$C_{25}$ alkyl and divalent linear or branched $C_1$-$C_{25}$ perhaloalkyl, in each case optionally interrupted with at least one of —O—, —C(O) O—, and —OC(O)O—.

With further reference to Formula (X), and in accordance with some embodiments, independently for each $M^1$, independently for each $M^2$, independently for each $M^3$, and independently for each $M^4$: $L^3$, independently for each q, is represented by the following Formula (XI-2), Formula (XI-2)

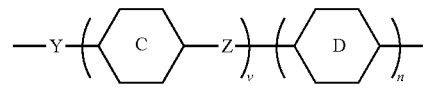

With reference to Formula (XI-2), the divalent rings,

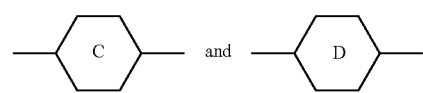

are each independently selected, for each v and each u, from the group consisting of phenylen-1,4-diyl, substituted phenylen-1,4-diyl, cyclohexan-1,4-diyl, substituted cyclohexan-1,4-diyl, pyrimidin-2,5-diyl, substituted pyrimidin-2,5-diyl, pyridine-2,5-diyl, substituted pyridine-2,5-diyl, naphthalene-2,6-diyl, naphthalene-1,4-diyl, substituted naphthalene-2,6-diyl, 1,2,3,4-tetrahydronaphthalene-2,6-diyl, 1,2,3,4-tetrahydronaphthalene-2,6-diyl in which the aromatic ring is substituted, decahydronaphthalene-2,6-diyl, indane-2,5(6)-diyl, fluorene-2,-7-diyl, phenanthrene-2,7-diyl, 9,10-dihydrophenanthrene-2,7-diyl, (1,3,4)thiadiazol-2,5-diyl, (1,3)thiazol-2,5-diyl, (1,3)thiazol-2,4-diyl, thiophen-2,4-diyl, thiophen-2,5-diyl, (1,3)dioxan-2,5-diyl, piperidin-1,4-diyl, and piperazin-1,4-diyl.

With further reference to Formula (X), and in accordance with some embodiments, independently for each $M^1$, independently for each $M^2$, independently for each $M^3$, and independently for each $M^4$: $E^1$ is in each case independently selected from the group consisting of hydrogen, linear or branched $C_1$-$C_{25}$ alkyl, linear or branched $C_2$-$C_{25}$ alkenyl, each optionally interrupted with at least one of —O— and —C(O)O—.

With reference to Formula (II), and in accordance with some embodiments, $R^4$ is selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$—$C_{12}$ heterocycloalkyl, aryl, heteroaryl, —OR$^8$, and $M^2$, where $R^8$ is selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

With reference to Formula (III), and in accordance with some embodiments, Ring-A is aryl or substituted aryl.

With reference to Formula (IV), and in accordance with some embodiments: Ring-B is aryl or substituted aryl; and $R_2'$ of D (where D is N—$R_2'$) is selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

With reference to Formula (VI), and in accordance with some embodiments: $R^5$ is selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, heteroaryl, and $M^2$; $R^{11}$ is selected from the group consisting of hydrogen, —CN, —C(O)OR$^{13}$, linear or branched $C_1$-$C_{25}$ alkyl, linear or branched $C_2$-$C_{25}$ alkenyl, and $C_3$-$C_{12}$ cycloalkyl, where $R^{13}$ is selected from the group consisting of hydrogen, linear or branched $C_1$-$C_{25}$ alkyl, linear or branched $C_2$-$C_{25}$ alkenyl, and $C_3$-$C_{12}$ cycloalkyl; and $R^{12}$ is selected from the group consisting of hydrogen, linear or branched $C_1$-$C_{25}$ alkyl, linear or branched $C_2$-$C_{25}$ alkenyl, and $C_3$-$C_{12}$ cycloalkyl.

Independently for each of Formulas (I), (II), (III), (IV), (V), (VI), (VII), (VIII), and (IX), and in accordance with some embodiments, $R^1$ independently for each x, $R^2$ independently for each y, and $R^6$ independently for each d, are in each case independently selected from the group consisting of hydrogen, linear or branched $C_1$-$C_{10}$ alkyl, and —OR$^7$, where each $R^7$ is independently selected from the group consisting of hydrogen, and linear or branched $C_1$-$C_{10}$ alkyl.

Independently for each Formula (X), and in accordance with some embodiments, independently for each $M^1$, independently for each $M^2$, independently for each $M^3$, and independently for each $M^4$: $L^2$, independently for each m, is selected from the group consisting of divalent linear or branched $C_1$-$C_{10}$ alkyl and divalent linear or branched $C_1$-$C_{10}$ perfluoroalkyl, in each case optionally interrupted with at least one of —O—, —C(O)O—, and —OC(O)O—.

With further reference to Formula (X), and in accordance with some embodiments, independently for each $M^1$, independently for each $M^2$, independently for each $M^3$, and independently for each $M^4$, independently for each $L^3$: (i) Z is, independently for each v, selected from the group consisting of a single bond, —O—, and —C(O)O—; and (ii) the divalent rings,

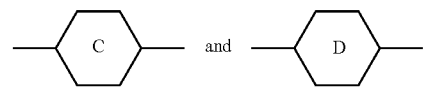

are each independently selected, for each v and each u, from the group consisting of phenylen-1,4-diyl, substituted phenylen-1,4-diyl, cyclohexan-1,4-diyl, and substituted cyclohexan-1,4-diyl.

With further reference to Formula (X), and in accordance with some embodiments, independently for each $M^1$, independently for each $M^2$, independently for each $M^3$, and independently for each $M^4$: $E^1$ is in each case independently selected from the group consisting of hydrogen and linear or branched $C_1$-$C_{10}$ alkyl optionally interrupted with at least one of —O— and —C(O)O—.

In accordance with some embodiments, and with further reference to Formula (X), at least one $E^1$ is, or is substituted with, (meth)acryloyl.

With reference to Formula (II), and in accordance with some embodiments, $R^4$ is selected from the group consisting of hydrogen, linear or branched $C_1$-$C_{10}$ alkyl, —OR$^8$, and $M^2$, where $R^8$ is selected from the group consisting of hydrogen and linear or branched $C_1$-$C_{10}$ alkyl.

With reference to Formula (III), and in accordance with some embodiments: Ring-A is phenyl; and g is from 0 to 4, provided that the sum of n and g is at least 1. When Ring-A is phenyl, the compound represented to Formula (III) is represented by the following Formula (III-1),

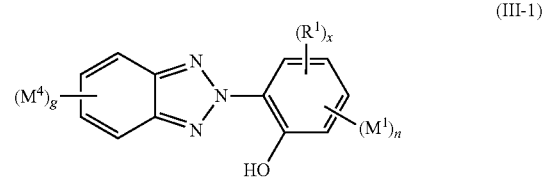

With reference to Formula (III-1), g, n, x, $M^4$, and $R^1$ are each independently as described previously and further herein.

With reference to Formula (IV), and in accordance with some embodiments: Ring B is phenyl; $R_2'$ of D is selected from the group consisting of hydrogen and linear or branched $C_1$-$C_{10}$ alkyl; and g is from 0 to 4, provided that the sum of n and g is at least 1. When Ring-B is phenyl, the compound represented by Formula (IV) is represented by the following Formula (IV-1),

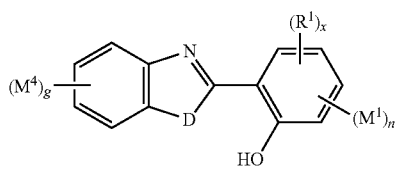
(IV-1)

With reference to Formula (IV-1), g, n, x, $M^4$, D, and $R^1$ are each independently as described previously and further herein.

With reference to Formula (VI), and in accordance with some embodiments: $R^5$ is selected from the group consisting of hydrogen, linear or branched $C_1$-$C_{10}$ alkyl, and $M^2$; $R^{11}$ is selected from the group consisting of hydrogen, —CN, —C(O)O$R^{13}$, and linear or branched $C_1$-$C_{10}$ alkyl, where $R^{13}$ is selected from the group consisting of hydrogen and linear or branched $C_1$-$C_{10}$ alkyl; and $R^{12}$ is selected from the group consisting of hydrogen and linear or branched $C_1$-$C_{10}$ alkyl.

With reference to Formula (XI-1), and in accordance with some embodiments, divalent Ring-(C),

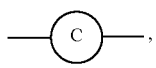

independently from each v, and divalent Ring-(D),

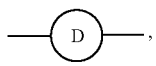

independently for each u, are each independently selected from the group consisting of divalent aryl, substituted divalent aryl, divalent heteroaryl, and substituted divalent heteroaryl.

With reference to Formula (XI-2), and in accordance with some embodiments, divalent Ring-(C),

independently for each v, and divalent Ring-(D),

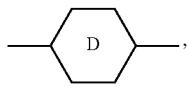

independently for each u, are each independently selected from the group consisting of phenylen-1,4-diyl, substituted phenylen-1,4-diyl, pyrimidin-2,5-diyl, substituted pyrimidin-2,5-diyl, pyridine-2,5-diyl, substituted pyridine-2,5-diyl, naphthalene-2,6-diyl, substituted naphthalene-2,6-diyl, and phenanthrene-2,7-diyl.

With further reference to Formula (XI-2), and in accordance with some embodiments, divalent Ring-(C),

independently for each v, and divalent Ring-(D),

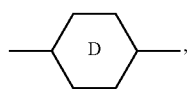

independently for each u, are each independently selected from the group consisting of phenylen-1,4-diyl and substituted phenylen-1,4-diyl.

With reference to Formula (I), and in accordance with some embodiments, the sum of n and p is 1.

With reference to Formula (II), and in accordance with some embodiments: n is 1; and $R^4$ is selected from the group consisting of hydrogen, linear or branched $C_1$-$C_{10}$ alkyl, and —O$R^8$, where $R^8$ is selected from the group consisting of hydrogen and linear or branched $C_1$-$C_{10}$ alkyl.

With reference to Formula (III), and in accordance with some embodiments, the sum of n and g is 1.

With reference to Formula (IV), and in accordance with some embodiments, the sum of n and g is 1.

With reference to Formula (V), and in accordance with some embodiments, the sum of n and p is 1.

With reference to Formula (VI), and in accordance with some embodiments: n is 1; and $R^5$ is selected from the group consisting of hydrogen and linear or branched $C_1$-$C_{10}$ alkyl.

With reference to Formula (VII), and in accordance with some embodiments, the sum of n, p, and f is 1.

With reference to Formula (VIII), and in accordance with some embodiments, n is 1.

With reference to Formula (IX), and in accordance with some embodiments, n is 1.

Independently for each Formula (X), and in accordance with some embodiments, independently for each $M^1$, independently for each $M^2$, independently for each $M^3$, and independently for each $M^4$, each $L^3$ is independently selected from the group consisting of the following formulas:

Formula XI(A)
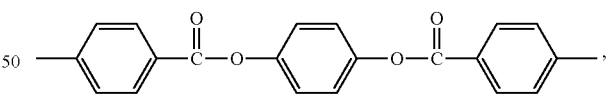

Formula XI(B)
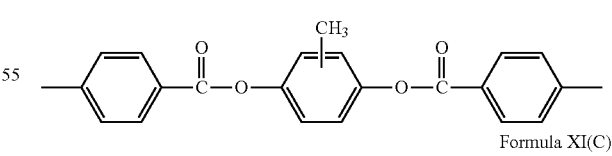

Formula XI(C)
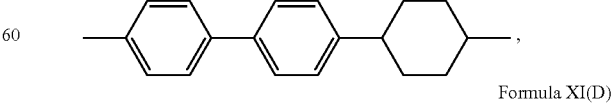

Formula XI(D)
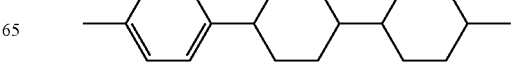

-continued

Formula XI(E)
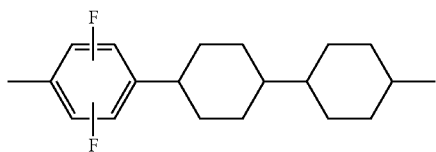

Formula XI(F)
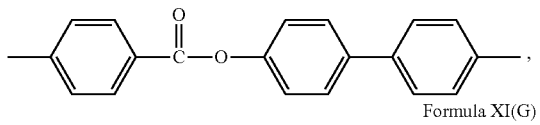

Formula XI(G)
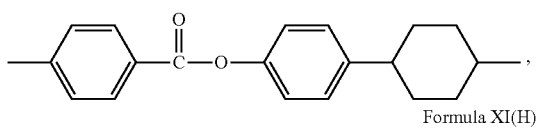

Formula XI(H)
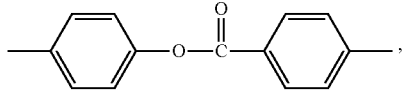

Formula XI(I)
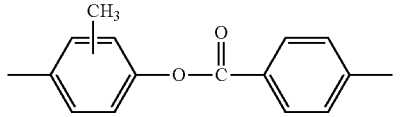

Formula XI(J)
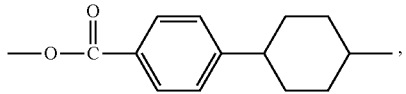

Formula XI(K)
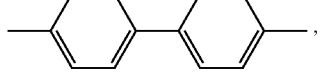

Formula XI(L)
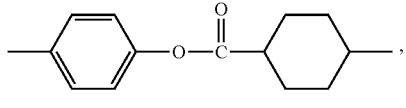

Formula XI(M)
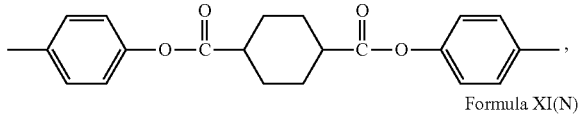

Formula XI(N)
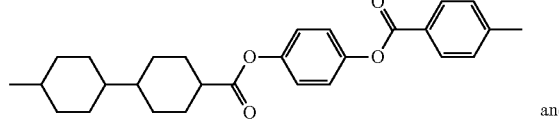

and

Formula XI(O)
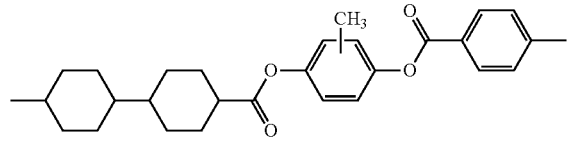

Independently for each compound of the present invention, such as represented by Formulas (I), (II), (III), (IV), (V), (VI), (VII), (VIII), and (IX), and in accordance with some embodiments, at least one $L^3$ of Formula (X) is a mesogenic group, and each compound of the present invention independently is a mesogenic compound.

In accordance with some embodiments, each compound of the present invention independently is an ultraviolet light absorbing compound. In accordance with some further embodiments, each compound of the present invention independently is a mesogenic ultraviolet light absorbing compound.

In accordance with some embodiments, the present invention relates to a composition that includes at least one compound of the present invention. For purposes of non-limiting illustration, the composition of the present invention can be, with some embodiments, a curable composition, a thermoplastic composition, a coating composition, a molding composition, an extrudable composition, an imbibing composition (i.e., a composition that can be imbibed into an article, such as an organic polymeric article), and a liquid-crystal composition.

With some embodiments, the composition of the present invention further includes at least one of, (i) a photochromic compound, (ii) a dichroic compound, (iii) a photochromic-dichroic compound, and (iv) a fixed tint.

Classes of photochromic compounds that can be included in the compositions of the present invention include, but are not limited to, thermally reversible pyrans, non-thermally reversible pyrans, thermally reversible oxazines, non-thermally reversible oxazines, thermally reversible fulgides, and/or non-thermally reversible fulgides.

Examples of thermally reversible photochromic pyrans from which photochromic compound(s) can be chosen and that can be used with various embodiments of the present invention, include, but are not limited to: benzopyrans; naphthopyrans, e.g., naphtho[1,2-b]pyrans, naphtho[2,1-b]pyrans; indeno-fused naphthopyrans, such as those disclosed in U.S. Pat. No. 5,645,767 at col. 2, line 16 to col. 12, line 57; heterocyclic-fused naphthopyrans, such as those disclosed in U.S. Pat. No. 5,723,072 at col. 2, line 27 to col. 15, line 55, U.S. Pat. No. 5,698,141 at col. 2, line 11 to col. 19, line 45, U.S. Pat. No. 6,153,126 at col. 2, line 26 to col. 8, line 60, and U.S. Pat. No. 6,022,497 at col. 2, line 21 to col. 11, line 46; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Additional examples of naphthopyrans and related organic photochromic substances are described, for example, in U.S. Pat. No. 5,658,501 at col. 1, line 64 to col. 13, line 17. The pertinent cited portions of the preceding U.S. patents are incorporated herein by reference. Spiro(indoline)pyrans are also described in the text, Techniques in Chemistry, Volume III, "Photochromism", Chapter 3, Glenn H. Brown, Editor, John Wiley and Sons, Inc., New York, 1971.

Examples of thermally reversible photochromic oxazines from which photochromic compound(s) can be chosen and that can be used with various embodiments of the present invention, include, but are not limited to, benzoxazines, naphthoxazines, and spiro-oxazines, e.g., spiro(indoline) naphthoxazines, spiro(indoline)pyridobenzoxazines, spiro (benzindoline) pyridobenzoxazines, spiro(benzindoline) naphthoxazines, spiro(indoline)benzoxazines, spiro (indoline)fluoranthenoxazine, and spiro(indoline) quinoxazine.

Examples of thermally reversible photochromic fulgides from which photochromic compound(s) can be chosen and that can be used with various embodiments of the present invention, include, but are not limited to: fulgimides, such as, 3-furyl and 3-thienyl fulgimides; fulgides, such as 3-furyl and 3-thienyl fulgides, which are disclosed in U.S. Pat. No.

4,931,220 at column 2, line 51 to column 10, line 7, and mixtures of any of the aforementioned photochromic materials/compounds. Examples of further non-thermally reversible photochromic compounds that can be used with various embodiments of the present invention, such as the liquid crystal compositions of the present invention include, but are not limited to the photochromic compounds disclosed in US Patent Application Publication 2005/0004361 at paragraphs [0314] to [0317].

With some embodiments, the photochromic compounds that can be used with various embodiments of the present invention can be selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, mixtures thereof, and combinations thereof.

Examples of dichroic compounds that can be included in the compositions of the present invention include, but are not limited to, the dichroic compounds described in U.S. Pat. No. 7,097,303 at column 7, lines 6 to 60. Further examples of dichroic compounds that can be used with various embodiments of the present invention include, but are not limited to, azomethines, indigoids, thioindigoids, merocyanines, indans, quinophthalonic dyes, perylenes, phthaloperines, triphenodioxazines, indoloquinoxalines, imidazotriazines, tetrazines, azo and (poly)azo dyes, benzoquinones, naphthoquinones, anthroquinone and (poly)anthroquinones, anthropyrimidinones, iodine and iodates. The dichroic compounds can be in some embodiments selected from polymerizable dichroic compounds, that include at least one group that is capable of being polymerized. Non-limiting examples of polymerizable groups of the polymerizable dichroic compounds include, but are not limited to, ethylenically unsaturated groups that are radically polymerizable, such as (meth) acrylate groups, allyl groups, and/or vinyl groups.

With some embodiments, the composition of the present invention includes a dichroic compound, and a layer is formed from the composition. To ensure that a net linear polarization is obtained, the dichroic compounds of the layer are typically aligned in accordance with art-recognized methods. A non-limiting example of an alignment facility that can be used for purposes of aligning dichroic compounds is described in U.S. Pat. No. 7,632,540 at column 2, line 6 through column 28, line 24 thereof.

Photochromic-dichroic compounds that can be included in the compositions of the present invention include, with some embodiments: (a) at least one photochromic group (PC), which can be chosen from known photochromic compounds such as, but not limited to, pyrans, oxazines, fulgides, and other examples described previously herein; and (b) at least one lengthening agent or group attached to the photochromic group. The lengthening agent (L), with some embodiments, can be represented by the following Formula A:

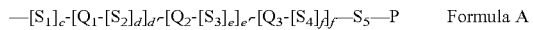

—[S$_1$]$_c$-[Q$_1$-[S$_2$]$_d$]$_{d'}$-[Q$_2$-[S$_3$]$_e$]$_{e'}$-[Q$_3$-[S$_4$]$_f$]$_{f'}$—S$_5$—P    Formula A As used herein, the term "attached" with regard to the photochromic group of the photochromic-dichroic compound means directly bonded to or indirectly bonded through another group. Thus, for example, according to various non-limiting embodiments disclosed herein, L can be directly bonded to PC as a substituent on PC, or L can be a substituent on another group (such as a group represented by R$^1$, which is discussed below) that is directly bonded to PC (i.e., L is indirectly bonded to PC). Although not limiting herein, according to various non-limiting embodiments, L can be attached to PC so as to extend or lengthen PC in an activated state such that the absorption ratio of the extended PC (i.e., the photochromic compound) is enhanced as compared to PC alone. Although not limiting herein, according to various non-limiting embodiments, the location of attachment of L on PC can be chosen such that L lengthens PC in at least one of a direction parallel to and a direction perpendicular to a theoretical transitional dipole moment of the activated form of PC. As used herein the term "theoretical transitional dipole moment" refers to transient dipolar polarization created by interaction of electromagnetic radiation with the molecule. See, for example, IUPAC Compendium of Chemical Technology, 2$^{nd}$ Ed., International Union of Pure and Applied Chemistry (1997).

With reference to Formula A above, each Q$_1$, Q$_2$, and Q$_3$ can be independently chosen for each occurrence from: a divalent group chosen from an unsubstituted or a substituted aromatic group, an unsubstituted or a substituted alicyclic group, an unsubstituted or a substituted heterocyclic group, and mixtures thereof, wherein substituents are chosen from: a group represented by P (as set forth below), aryl, thiol, amide, liquid crystal mesogens, halogen, C$_1$-C$_{18}$ alkoxy, poly(C$_1$-C$_{18}$ alkoxy), amino, amino(C$_1$-C$_{18}$)alkylene, C$_1$-C$_{18}$alkylamino, di-(C$_1$-C$_{18}$)alkylamino, C$_1$-C$_{18}$ alkyl, C$_2$-C$_{18}$ alkene, C$_2$-C$_{18}$ alkyne, C$_1$-C$_{18}$ alkyl(C$_1$-C$_{18}$)alkoxy, C$_1$-C$_{18}$ alkoxycarbonyl, C$_1$-C$_{18}$ alkylcarbonyl, C$_1$-C$_{18}$ alkyl carbonate, aryl carbonate, C$_1$-C$_{18}$ acetyl, C$_3$-C$_{10}$ cycloalkyl, C$_3$-C$_{10}$ cycloalkoxy, isocyanato, amido, cyano, nitro, a straight-chain or branched C$_1$-C$_{18}$ alkyl group that is mono-substituted with cyano, halo, or C$_1$-C$_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

With reference to Formula A above, each Q$_1$, Q$_2$, and Q$_3$ can be independently chosen for each occurrence from: a divalent group chosen from an unsubstituted or a substituted aromatic group, an unsubstituted or a substituted alicyclic group, an unsubstituted or a substituted heterocyclic group, and mixtures thereof, wherein substituents are chosen from: a group represented by P (as set forth below), aryl, thiol, amide, liquid crystal mesogens, halogen, C$_1$-C$_8$ alkoxy, poly(C$_1$-C$_{18}$ alkoxy), amino, amino(C$_1$-C$_{18}$)alkylene, C$_1$-C$_{18}$alkylamino, di-(C$_1$-C$_{18}$)alkylamino, C$_1$-C$_{18}$ alkyl, C$_2$-C$_{18}$ alkene, C$_2$-C$_{18}$ alkyne, C$_1$-C$_{18}$ alkyl(C$_1$-C$_{18}$)alkoxy, C$_1$-C$_{18}$ alkoxycarbonyl, C$_1$-C$_{18}$ alkylcarbonyl, C$_1$-C$_{18}$ alkyl carbonate, aryl carbonate, C$_1$-C$_{18}$ acetyl, C$_3$-C$_{10}$ cycloalkyl, C$_3$-C$_{10}$ cycloalkoxy, isocyanato, amido, cyano, nitro, a straight-chain or branched C$_1$-C$_{18}$ alkyl group that is mono-substituted with cyano, halo, or C$_1$-C$_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

As discussed above, $Q_1$, $Q_2$, and $Q_3$ can be independently chosen for each occurrence from a divalent group, such as an unsubstituted or a substituted aromatic group, unsubstituted or substituted heterocyclic group, and an unsubstituted or substituted alicylic group. Non-limiting examples of useful aromatic groups include: benzo, naphtho, phenanthro, biphenyl, tetrahydro naphtho, terphenyl, and anthraceno.

As used herein the term "heterocyclic group" means a compound having a ring of atoms, wherein at least one atom forming the ring is different than the other atoms forming the ring. Further, as used herein, the term heterocyclic group specifically excludes fused heterocyclic groups. Non-limiting examples of suitable heterocyclic groups from which $Q_1$, $Q_2$, and $Q_3$ can be chosen include: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

As discussed above, $Q_1$, $Q_2$, and $Q_3$ can be chosen from mono- or di-substituted $C_4$-$C_{18}$ spirobicyclic amine and $C_4$-$C_{18}$ spirotricyclic amine. Non-limiting examples of suitable substituents include aryl, $C_1$-$C_6$ alkyl, $C_1$-$C_6$ alkoxy or phenyl ($C_1$-$C_6$)alkyl. Specific non-limiting examples of mono- or di-substituted spirobicyclic amines include: 2-azabicyclo[2.2.1]hept-2-yl; 3-azabicyclo[3.2.1]oct-3-yl; 2-azabicyclo[2.2.2]oct-2-yl; and 6-azabicyclo[3.2.2]nonan-6-yl. Specific non-limiting examples of mono- or di-substituted tricyclic amines include: 2-azatricyclo[3.3.1.1(3,7)]decan-2-yl; 4-benzyl-2-azatricyclo[3.3.1.1(3,7)]decan-2-yl; 4-methoxy-6-methyl-2-azatricyclo[3.3.1.1(3,7)]decan-2-yl; 4-azatricyclo[4.3.1.1 (3,8)]undecan-4-yl; and 7-methyl-4-azatricyclo[4.3.1.1(3,8)]undecan-4-yl. Examples of alicylic groups from which $Q_1$, $Q_2$, and $Q_3$ can be chosen include, without limitation, cyclohexyl, cyclopropyl, norbornenyl, decalinyl, adamantanyl, bicycloctane, per-hydrofluorene, and cubanyl.

With continued reference to Formula A, each $S_1$, $S_2$, $S_3$, $S_4$, and $S_5$ is independently chosen for each occurrence from a spacer unit chosen from:
  (1) —$(CH_2)_g$—, —$(CF_2)_h$—, —$Si(CH_2)_g$—, —$(Si[(CH_3)_2]O)_h$—, wherein g is independently chosen for each occurrence from 1 to 20; h is chosen from 1 to 16;
  (2) —N(Z)—, —C(Z)=C(Z)—, —C(Z)=N—, —C(Z')—C(Z')—, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and
  (3) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;

The selection of $S_1$, $S_2$, $S_3$, $S_4$, and $S_5$ is subject, however, to the proviso, that when two spacer units including heteroatoms are linked together, the spacer units are linked so that heteroatoms are not directly linked to each other, and when $S_1$ and $S_5$ are linked to PC and P, respectively, they are linked so that two heteroatoms are not directly linked to each other. As used herein the term "heteroatom" means atoms other than carbon or hydrogen.

Further, in Formula A, according to various non-limiting embodiments, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Further, in Formula A, P can be chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$) alkyl($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, a liquid crystal mesogen, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from an alkyl, an alkoxy, amino, cycloalkyl, alkylalkoxy, a fluoroalkyl, a cyanoalkyl, a cyanoalkoxy and mixtures thereof.

Further, although not limiting herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

In accordance with some embodiments, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls. According to another specific, non-limiting embodiment, P can be chosen from a steroid, for example and without limitation, a cholesterolic compound.

With some embodiments, the lengthening group L of the photochromic-dichroic compound is selected from Formulas XI(A) through XI(O), in which one end thereof is bonded to: a linear or branched $C_1$-$C_{10}$ alkyl group; or a linear or branched $C_1$-$C_{10}$ fluoroalkyl group; or a linear or branched $C_1$-$C_{10}$ perfluoroalkyl group. Further examples of lengthening groups L of the photochromic-dichroic compound include, but are not limited to, those disclosed in column 34, line 5 through column 45, line 51 of U.S. Pat. No. 8,582,192 B2, which disclosure is incorporated herein by reference.

Classes of photochromic groups (PC) of the photochromic-dichroic compound include, but are not limited to, those classes of photochromic compounds described previously herein, such as thermally reversible pyrans, non-thermally reversible pyrans, thermally reversible oxazines, non-thermally reversible oxazines, thermally reversible fulgides, and/or non-thermally reversible fulgides.

With some embodiments, the photochromic-dichroic compounds used with various embodiments of the present invention include a residue of a photochromic compound, in which the photochromic compound is selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds.

Further examples of photochromic-dichroic compounds that can be used with various embodiments of the present invention include, but are not limited to, those disclosed in: U.S. Pat. No. 7,256,921 at paragraphs [0089] to [0339]; U.S. Patent Application Publication No. US 2009/0309076 at paragraphs [0029] to [0137]; U.S. Patent Application Publication No. 2011/0140056 A1; U.S. Pat. Nos. 8,518,546; and 8,545,984. In addition, a general structure for photochromic-dichroic compounds is presented in U.S. Pat. No. 7,342,112 at column 5, line 35 to column 31, line 3 and Table V spanning columns 97-102.

Examples of static dyes or fixed tints (i.e., dyes or tints that are not photochromic) that can be present in the compositions of and used with the various embodiments of the present invention include, but are not limited to, art-recognized static organic dyes that are capable of imparting a desired color or other optical property to the photochromic coating layer. Examples of static dyes that can be present in the in the compositions of and used with the various embodiments of the present invention include, but are not limited to, azo dyes, anthraquinone dyes, xanthene dyes, azime dyes, iodine, iodide salts, polyazo dyes, stilbene dyes, pyrazolone dyes, triphenylmethane dyes, quinoline dyes, oxazine dyes, thiazine dyes, polyene dyes, and mixtures and/or combinations thereof. Examples of anthraquinone dyes from which the fixed dye can be selected, with some embodiments, include but are not limited to, 1,4-dihydroxy-9,10-antracenedione (CAS registry No. 81-64-1), 1,4-bis(4-methylphenyl)amino-9,10-anthracendione (CAS registry No. 128-80-3), 1,4-bis((2-bromo-4,6-dimethylphenyl)amino)-9,10-anthracenedione (CAS registry No. 18038-98-8), and mixtures thereof.

The compositions and articles according to various embodiments of the present invention can include any amount of the photochromic compound, dichroic compound, photochromic-dichroic compound, and/or fixed tint necessary to achieve the desired optical properties, such as photochromic properties, dichroic properties, and/or static tint properties.

In accordance with some embodiments, the compositions of the present invention further include a liquid crystal material.

Liquid crystal materials that can be present in the compositions of the present invention, can be chosen from liquid crystal polymers, liquid crystal pre-polymers, and liquid crystal monomers, with some embodiments. As used herein the term "pre-polymer" means partially polymerized materials that are capable of undergoing further polymerization or polymer chain extension.

Liquid crystal monomers that can be included in the compositions of the present invention include mono-functional and multi-functional liquid crystal monomers, with some embodiments. With some embodiments, the liquid crystal monomer can be a cross-linkable liquid crystal monomer, and can further be a photocross-linkable liquid crystal monomer. As used herein the term "photocross-linkable" means a material, such as a monomer, a pre-polymer or a polymer, that undergoes crosslinking after exposure to actinic radiation.

Examples of cross-linkable liquid crystal monomers include, but are not limited to, liquid crystal monomers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers and blends thereof. Examples of photocross-linkable liquid crystal monomers include, but are not limited to, liquid crystal monomers having functional groups chosen from acrylates, methacrylates, alkynes, allyls, epoxides, thiols, and blends thereof.

Liquid crystal polymers and pre-polymers that can be included in the compositions of the present invention include thermotropic liquid crystal polymers and pre-polymers, and lyotropic liquid crystal polymers and pre-polymers. Further, the liquid crystal polymers and pre-polymers can be main-chain polymers and pre-polymers or side-chain polymers and pre-polymers. Additionally, according to various embodiments of the present invention, the liquid crystal polymer or pre-polymer can be cross-linkable, and further can be photocross-linkable.

Examples of liquid crystal polymers and pre-polymers that can be included in the compositions of the present invention, include main-chain and side-chain polymers and pre-polymers having functional groups chosen from acrylates, methacrylates, allyl, allyl ethers, alkynes, amino, metal anhydrides, epoxides, hydroxides, isocyanates, blocked isocyanates, siloxanes, thiocyanates, thiols, urea, vinyl, vinyl ethers, and blends thereof. Examples of photocross-linkable liquid crystal polymers and pre-polymers that can be included in the compositions of the present invention include polymers and pre-polymers having functional groups chosen from acrylates, methacrylates, alkynes, epoxides, thiols, and blends thereof. The liquid crystal polymers and prepolymers can be selected from art-recognized polymers and prepolyers, such as, polyethers, polyesters, polyurethanes, polyacrylates, and combinations of two or more thereof.

The compositions of the present invention, can further include an additive selected from a liquid crystal property control agent, a non-linear optical material, an alignment promoter, a kinetic enhancer, a photoinitiator, a thermal initiator, a surfactant, a polymerization inhibitor, a solvent, a conventional light stabilizer (e.g., ultraviolet light absorbers and light stabilizers including hindered amine groups), a conventional thermal stabilizer, a mold release agent, a rheology control agent, a gelator, a leveling agent (e.g., a surfactant), a free radical scavenger, and/or an adhesion promoter/coupling agent (e.g., hexane diol diacrylate). The conventional light stabilizers are optionally used in addition to the compounds of the present invention, such as represented by Formulas (I) through (IX).

Surfactants that can be included in the compositions of the present invention, include materials also referred to as wetting agents, anti-foaming agents, emulsifiers, dispersing agents, leveling agents etc. The surfactant can be selected from anionic surfactants, cationic surfactants, nonionic surfactants, and combinations thereof. Surfactants that can be included in the compositions and articles of the present invention, include art-recognized and commercially available surfactants. Examples of nonionic surfactants include, but are not limited to, ethoxylated alkyl phenols, such as the IGEPAL® DM surfactants or octyl-phenoxypolyethoxyethanol sold as TRITON® X-100, acetylenic diols such as 2,4,7,9-tetramethyl-5-decyne-4,7-diol sold as SURFYNOL® 104, ethoxylated acetylenic diols, such as the SURFYNOL®400 surfactant series, fluoro-surfactants, such as the FLUORAD® fluorochemical surfactant series, and capped nonionics such as the benzyl capped octyl phenol ethoxylates sold as TRITON® CF87, the propylene oxide capped alkyl ethoxylates, which are available as the PLURAFAC® RA series of surfactants, octylphenoxyhexadecylethoxy benzyl ether, polyether modified dimethylpolysiloxane copolymer in solvent sold as BYK®-306 additive by Byk Chemie and mixtures of such surfactants.

The compositions and articles of the present invention can optionally further include non-linear optical (NLO) materials. Non-linear optical materials include, but are not limited to, organic materials that exhibit non-linear optical properties and form crystals. Examples of non-linear optical materials include, but are not limited to: N-(4-nitrophenyl)-(L)-prolinol (NPP); 4-N,N-dimethylamino-4'-N'-methylstilbazolium tosylate (DAST); 2-methyl-4-nitroaniline (MNA); 2-amino-5-nitropyridine (2A5NP); p-chlorophenylurea (PCPU); and 4-(N,N-dimethylamino)-3-acetamidonitrobenzene (DAN). Further examples of non-linear optical materials include those disclosed in U.S. Pat. No. 6,941,051 at column 4, lines 4-37.

Examples of thermal stabilizers that can be included in the compositions and articles of the present invention include basic nitrogen-containing compounds, such as, biurea, allantoin or a metal salt thereof, a carboxylic acid hydrazide (e.g., an aliphatic or aromatic carboxylic acid hydrazide), a metal salt of an organic carboxylic acid, an alkali or alkaline earth metal compound, a hydrotalcite, a zeolite and an acidic compound (e.g., a boric acid compound, a nitrogen-containing cyclic compound having a hydroxyl group, a carboxyl group-containing compound, a (poly)phenol, butylated hydroxytoluene, and an aminocarboxylic acid) or mixtures thereof.

Examples of mold release agents that can be included or used in conjunction with the compositions and articles of the present invention include, but are not limited to, esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

Rheology control agents that can be used with the compositions of the present invention can also be referred to as thickeners, and include, but are not limited to powders (or particulate materials), such as inorganic particulate materials (e.g., silica), and organic particulate materials, such as microcrystalline cellulose or particulate polymeric materials.

Gelators (or gelling agents) that can be included in the compositions of the present invention, include, but are not limited to, organic materials that can also affect the thixotropy of the composition into which they are incorporate. Examples of gelators include, but are not limited to, natural gums, starches, pectins, agar-agar, and gelatins. Gelators that can be used in the present invention include materials based on polysaccharides or proteins.

The compositions of the present invention can include free radical scavengers, examples of which include, but are not limited to: synthetic pseudopeptides resistant to hydrolysis, such as Carcinine hydrochloride; lipoamino acids, such as L-lysine lauroylmethionine; plant extracts containing multi-enzymes; natural tocopherol and related compounds, as well as compounds containing an active hydrogen such as —OH, —SH, or —NRH group, where R is a hydocarbyl group. Further examples of free radical scavengers include, but are not limited to, sterically hindered amines.

Adhesion promoters that can be included in the compositions and articles of the present invention include organosilane compounds, such as aminoorganosilane materials, silane coupling agents, organic titanate coupling agents and organic zirconate coupling agents described in U.S. Pat. No. 7,410,691 at paragraphs [0033] to [0042]. Further examples of adhesion promoters include zirco-aluminate adhesion promoting compounds that are commercially available from Rhone-Poulenc. Preparation of aluminum-zirconium complexes is described in the U.S. Pat. Nos. 4,539,048 and 4,539,049. These patents describe zirco-aluminate complex reaction products represented by the empirical Formula (B):

$$(Al_2(OR_1O)_aA_bB_c)_X(OC(R_2)O)_Y(ZrA_dB_e)_Z \qquad (B)$$

With reference to Formula (B), X, Y, and Z are at least 1, $R^2$ is an alkyl, alkenyl, aminoalkyl, carboxyalkyl, mercaptoalkyl, or epoxyalkyl group, having from 2 to 17 carbon atoms, and the ratio of X:Z is from about 2:1 to about 5:1. Additional zirco-aluminate complexes are described in U.S. Pat. No. 4,650,526.

The compositions of the present invention can optionally include one or more alignment promoters. Alignment promoters include materials that are capable of facilitating the rate of alignment and/or uniformity of alignment, of a material to which it is added. Examples of alignment promoters include, but are not limited to, those described in U.S. Pat. Nos. 6,338,808 and 6,875,483.

Kinetic enhancing additives can also optionally be included in the compositions of the present invention. Examples of kinetic enhancing additives include, but are not limited to, epoxy-containing compounds, organic polyols, and/or plasticizers. More specific examples of kinetic enhancing additives are disclosed in U.S. Pat. Nos. 6,433,043 and 6,713,536.

Examples of photoinitiators that can be present in the compositions of the present invention include, but are not limited to, cleavage-type photoinitiators and abstraction-type photoinitiators. Examples of cleavage-type photoinitiators include, but are not limited to, acetophenones, α-aminoalkylphenones, benzoin ethers, benzoyl oximes, acylphosphine oxides and bisacylphosphine oxides or mixtures of such initiators. A commercial example of a cleavage-type photoinitiator is DAROCURE® 4265 photoinitiator, which is available from Ciba Chemicals, Inc. Examples of abstraction-type photoinitiators include, but are not limited to, benzophenone, Michler's ketone, thioxanthone, anthraquinone, camphorquinone, fluorone, ketocoumarin or mixtures of such photoinitiators.

Photoinitiators that can be present in the compositions of the present invention, also include visible light photoinitiators. Examples of suitable visible light photoinitiators are described at column 12, line 11 to column 13, line 21 of U.S. Pat. No. 6,602,603.

The compositions of the present invention can optionally include one or more thermal initiators. Examples of thermal initiators include, but are not limited to, organic peroxy compounds and azobis(organonitrile) compounds. Examples of organic peroxy compounds include, but are not limited to, peroxymonocarbonate esters, such as tertiarybutylperoxy isopropyl carbonate; peroxydicarbonate esters, such as di(2-ethylhexyl) peroxydicarbonate, di(secondary butyl) peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide and p-chlorobenzoyl peroxide; peroxyesters such as t-butylperoxy pivalate, t-butylperoxy octylate and t-butylperoxyisobutyrate; methylethylketone peroxide, and acetylcyclohexane sulfonyl peroxide. With some embodiments, the thermal initiators used include those that do not discolor the resulting polymerizate. Examples of azobis(organonitrile) compounds include, but are not limited to, azobis(isobutyronitrile), azobis(2,4-dimethylvaleronitrile) and mixtures thereof.

The compositions of the present invention can optionally include one or more polymerization inhibitors. Examples of polymerization inhibitors include, but are not limited to: nitrobenzene, 1,3,5,-trinitrobenzene, p-benzoquinone, chloranil, DPPH, $FeCl_3$, $CuCl_2$, oxygen, sulfur, aniline, phenol, p-dihydroxybenzene, 1,2,3-trihydroxybenzene, and 2,4,6-trimethylphenol.

The compositions of the present invention can optionally include one or more solvents. Solvents that can be present in the compositions of the present invention include solvents: that are capable of dissolving solid components of the compositions; that are compatible with the compositions, optical elements and/or substrates; and/or that can ensure uniform coverage of surfaces to which the composition is applied. Examples of solvents include, but are not limited to: propylene glycol monomethyl ether acetate and their derivates (sold as DOWANOL® industrial solvents), acetone, amyl propionate, anisole, benzene, butyl acetate, cyclohexane, dialkyl ethers of ethylene glycol, e.g., diethylene glycol dimethyl ether and their derivates (sold as CELLOSOLVE® industrial solvents), diethylene glycol dibenzoate, dimethyl sulfoxide, dimethyl formamide, dimethoxybenzene, ethyl acetate, isopropyl alcohol, methyl cyclohexanone, cyclopentanone, methyl ethyl ketone, methyl isobutyl ketone, methyl propionate, propylene carbonate, tetrahydrofuran, toluene, xylene, 2-methoxyethyl ether, 3-propylene glycol methyl ether, and mixtures thereof.

The compounds and compositions of the present invention can be incorporated into an organic host material. Examples of organic host materials include synthetic and natural polymer materials. Organic host materials into which the compounds and compositions of the present invention can be incorporated include, but are not limited to, those materials described further herein with regard to the substrates of the articles of the present invention.

The present invention also relates to an article of manufacture that includes one or more compounds according to the present invention, such as represented by Formulas (I) through (IX). Articles of manufacture according to the present invention can have one or more compounds of the present invention, such as represented by Formulas (I) through (IX): incorporated directly therein, for example, prior to forming the article by molding; or applied to at least a portion of a surface of the article in the form of, one or more coatings that can optionally be cured and/or imbibed into the surface of the article, and/or a film, such as one or more laminated films.

With some embodiments of the present invention, the article of manufacture is an optical element that includes: (i) a substrate, such as an optical substrate; and (ii) a layer on at least a portion of a surface of the substrate (or optical substrate), in which the layer includes at least one compound of the present invention, such as represented by Formulas (I) through (IX). The layer can be formed, with some embodiments, from: one or more coating compositions; one or more films (such as laminated films); and combinations thereof.

The substrate, such as the optical substrate, of the optical elements of the present invention can, with some embodiments, be formed from and correspondingly include organic materials, inorganic materials, or combinations thereof (for example, composite materials).

Examples of organic materials that can be used as optical substrates of the optical elements of the present invention, include polymeric materials, such as homopolymers and copolymers, prepared from the monomers and mixtures of monomers disclosed in U.S. Pat. No. 5,962,617 and in U.S. Pat. No. 5,658,501 from column 15, line 28 to column 16, line 17. For example, such polymeric materials can be thermoplastic or thermoset polymeric materials, can be transparent or optically clear, and can have any refractive index required. Examples of such monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth) acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol) bismethacrylate monomers; urethane acrylate monomers; poly (ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

With some embodiments of the present invention, the optical substrate can be an ophthalmic substrate. As used herein the term "ophthalmic substrate" means lenses, partially formed lenses, and lens blanks. Examples of organic materials suitable for use in forming ophthalmic substrates include art-recognized polymers that are useful as ophthalmic substrates, such as organic optical resins that are used to prepare optically clear castings for optical applications, such as ophthalmic lenses.

Examples of inorganic materials that can be used as optical substrates with some embodiments of the present invention include glasses, minerals, ceramics, and metals. With some embodiments, the optical substrate can include glass. In other embodiments, the optical substrate can have a reflective surface, for example, a polished ceramic substrate, metal substrate, or mineral substrate. In other embodiments, a reflective coating or layer (e.g., a metal layer, such as a silver layer) can be deposited or otherwise applied to a surface of an inorganic or an organic substrate to make it reflective or to enhance its reflectivity.

In accordance with some embodiments of the present invention, the optical substrate can have a protective coating, for example, an abrasion-resistant coating, such as a "hard coat," on an exterior surface thereof. For purposes of non-limiting illustration, commercially available thermoplastic polycarbonate ophthalmic lens substrates are often sold with an abrasion-resistant coating already applied to its exterior surfaces because these surfaces tend to be readily scratched, abraded or scuffed. Correspondingly, as used herein, and in accordance with some embodiments, the term "optical substrate" includes an optical substrate having a protective coating, such as an abrasion-resistant coating, on one or more of surfaces thereof.

Optical substrates that can be used with optical elements according to some embodiments of the present invention can also include untinted, tinted, linearly polarizing, circularly polarizing, elliptically polarizing, photochromic, or tinted-photochromic substrates. As used herein with reference to optical substrates, the term "untinted" means optical substrates that are essentially free of coloring agent additions (such as conventional dyes) and have an absorption spectrum for visible radiation that does not vary significantly in response to actinic radiation. Further, with reference to optical substrates the term "tinted" means substrates that have a coloring agent addition (such as conventional dyes) and an absorption spectrum for visible radiation that does not vary significantly in response to actinic radiation.

As used herein, the term "circularly polarizing" with reference to optical substrates refers to optical substrates that are adapted to circularly polarize electromagnetic radiation. As used herein, the term "elliptically polarizing" with reference to optical substrates refers to optical substrates that are adapted to elliptically polarize electromagnetic radiation. Further, as used herein, with reference to optical substrates, the term "tinted-photochromic" means optical substrates containing a coloring agent addition as well as a photochromic material, and having an absorption spectrum for visible radiation that varies in response to at least actinic radiation. Thus, for example, a tinted-photochromic substrate can have a first color characteristic of the coloring agent and a second color characteristic of the combination of the coloring agent and the photochromic material when exposed to actinic radiation.

With some embodiments of the present invention, the layer of the articles and optical elements of the present invention is at least partially aligned by exposing at least a portion of said layer to at least one of a magnetic field, an electric field, linearly polarized radiation, and shear force. As used herein the term "aligned" means to bring into suitable arrangement or position by interaction with another material, compound and/or structure. With some embodiments, at least partial alignment of the layer results in a net linear polarization of transmitted radiation relative to the layer. Additional methods of aligning the layer include, but are not limited to, exposing the layer to plane-polarized ultraviolet radiation, exposing the layer to infrared radiation, etching the layer, rubbing the layer, and aligning the layer with another structure or material, such as an at least partially ordered alignment medium. Examples of alignment methods for layers are described in greater detail in U.S. Pat. No. 7,097,303, at column 27, line 17 to column 28, line 45.

With some embodiments of the present invention, the layer of the articles and optical elements of the present invention includes a liquid crystal phase having at least one of a nematic phase, a smectic phase, or a chiral nematic phase.

The layer including the compound of the present invention, that is present on at least a portion of a surface of the substrate (such as the optical substrate), can be selected from or formed from those compositions according to the present invention as described previously herein. The layer can be in the form of (or formed from) a curable coating, a thermoplastic coating, a laminated thermoset film, and/or a laminated thermoplastic film. The layer can be applied by art-recognized methods, such as, but not limited to, spin coating, spray coating, spray and spin coating, curtain coating, flow coating, dip coating, injection molding, casting, roll coating, wire coating, and overmolding. The layer or composition (such as a coating composition) including the compound of the present invention can be applied to an interior surface of a mold and the substrate can be formed on (e.g., on top of) the coating, in accordance with art-recognized overmolding methods.

Non-limiting examples of coating compositions of film forming polymers that can include the compounds of the present invention are as follows: those described in U.S. Pat. No. 7,256,921 at column 2, line 60 to column 94, line 23; polyurethane coatings, such as those described in U.S. Pat. No. 6,187,444 at column 3, line 4 to column 12, line 15; aminoplast resin coatings, such as those described in U.S. Pat. No. 6,432,544 at column 2, line 52 to column 14, line 5 and U.S. Pat. No. 6,506,488 at column 2, line 43 to column 12, line 23; polysiloxane coatings, such as those described in U.S. Pat. No. 4,556,605 at column 2, line 15 to column 7, line 27; poly(meth)acrylate coatings, such as those described in U.S. Pat. No. 6,602,603 at column 3, line 15 to column 7, line 50, U.S. Pat. No. 6,150,430 at column 8, lines 15-38, and U.S. Pat. No. 6,025,026 at column 8, line 66 to column 10, line 32; polyanhydride coatings, such as those described in U.S. Pat. No. 6,436,525 at column 2, line 52 to column 11, line 60; polyacrylamide coatings such as those described in U.S. Pat. No. 6,060,001 at column 2, line 6 to column 5, line 40; epoxy resin coatings, such as those described in U.S. Pat. No. 6,268,055 at column 2, line 63 to column 15, line 12; and poly(urea-urethane) coatings, such as those described in U.S. Pat. No. 6,531,076 at column 2, line 60 to column 10, line 49. The disclosures in the aforementioned U.S. patents that relate to the film-forming polymers are hereby incorporated herein by reference.

Non-limiting methods of applying films and sheets including the compounds of the present invention to a substrate (such as an optical substrate) include, for example, at least one of: laminating, fusing, in-mold casting, and adhesively bonding the polymeric sheet to the at least a portion of the substrate. As used herein, in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet.

The polymeric film or sheet can include a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly(urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric film or sheet also can include functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation e.g., acrylate groups), vinyl groups, and combinations thereof. Appropriate mixtures of film-forming resins can also be used in the preparation of the coating compositions. If the polymer composition from which the polymeric sheet is formed includes functional group-containing polymers (such as any of the previously mentioned functional group-containing polymers), the polymer composition can further include a material having functional groups reactive with those of said polymer. Reaction can be facilitated, for example, by thermal, photoinitiated, oxidative, and/or radiative curing techniques. Also contemplated are mixtures of any of the foregoing polymers.

Further non-limiting examples of polymers suitable for use in forming a polymeric film or sheet that includes the compound(s) of the present invention include thermoplastic block copolymers of polyalkyl(meth)acrylate and polyamide described in Published U.S. Pat. No. 7,282,551 at paragraphs [0020]-[0042], the specified portions of which is incorporated by reference herein; and U.S. Pat. No. 6,096, 375 at column 18, line 8 to column 19, line 5, the specified portions of which are incorporated by reference herein.

In accordance with some embodiments of the present invention, the polymeric film or sheet includes an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement; and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer."

The elastomeric polymer can include any of wide variety of art recognized elastomers including but not limited to copolymers of any of the previously mentioned polymers. In an embodiment of the present invention, the elastomeric polymer can include a block copolymer having ether and/or ester linkages in the polymer backbone. Examples of suitable block copolymers can include, but are not limited to, poly(amide-ether) block copolymers, poly(ester-ether) block copolymers, poly(ether-urethane) block copolymers, poly(ester-urethane) block copolymers, and/or poly(ether-urea) block copolymers. Suitable specific examples of such elastomeric polymers can include, but are not limited to, those commercially available under the tradenames DESMOPAN® and TEXIN® from Bayer Material Science; ARNITEL® from Royal DSM; and PEBAX® from Atofina Chemicals or Cordis Corporation.

Curing the compositions and/or layers that include the compound of the present invention can include at least partially polymerizing the composition or layer. Methods for at least partially polymerizing the composition/layer include exposing at least a portion of the composition/layer to at least one of thermal energy (for example to activate a thermal initiator), infrared radiation, ultraviolet radiation, visible radiation, gamma radiation, microwave radiation, electron radiation or combinations thereof so as to initiate the polymerization reaction of the polymerizable components or cross-linking with or without a catalyst or initiator. If desired or required, this can be followed by a heating step. According to some embodiments, the composition/layer can be cured to a specific or target surface hardness. For example, with some embodiments, the composition/layer can be cured to have a Fischer microhardness ranging from 0 to 150 Newtons/mm$^2$ that also exhibits good photochromic and/or dichroic response characteristics. With other embodiments, the composition/layer can be cured to a Fischer microhardness of less than 60 Newtons/mm$^2$, e.g. from 0 to 59.9 Newtons/mm$^2$, or alternatively from 5 to 25 N/mm$^2$. With additional embodiments, the composition/layer can be cured to have a Fischer microhardness ranging from 150 N/mm$^2$ to 250 N/mm$^2$ or alternatively from 150 N/mm$^2$ to 200 N/mm$^2$.

In accordance with further embodiments of the present invention, the optical element of the present invention is selected from an ophthalmic element, a display element, a window, a mirror, and a liquid crystal cell element. The optical element or device can also be chosen from ophthalmic elements and devices, display elements and devices, windows, mirrors, packaging material such as shrinkwrap, and active and passive liquid crystal cell elements and devices.

Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors. Non-limiting examples of display elements and devices include screens, monitors, and security elements, including without limitation, security marks and authentication marks. Non-limiting examples of windows include automotive and aircraft transparencies, filters, shutters, and optical switches.

With some embodiments, the optical element can be a security element. Examples of security elements include, but are not limited to, security marks and authentication marks that are connected to at least a portion of a substrate, such as: access cards and passes, e.g., tickets, badges, identification or membership cards, debit cards, etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

With further embodiments, the security element can be connected to at least a portion of a substrate chosen from a transparent substrate and a reflective substrate. Alternatively, according to further embodiments in which a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Additionally or alternatively, the security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, security elements according to the aforementioned embodiments can further include one or more other coatings or films or sheets to form a multi-layer reflective security element with viewing angle dependent characteristics, such as described in U.S. Pat. No. 6,641,874.

With some embodiments, the article of manufacture according to the present invention is a liquid crystal cell that includes: (i) a first substrate having a first surface; (ii) a second substrate having a second surface, the first surface of the first substrate and the second surface of the second substrate being in spaced opposition from each other, and together defining a space there-between; and (iii) a liquid crystal composition residing within at least a portion of the space, the liquid crystal composition includes the compound(s) of the present invention, such as represented by Formulas (I) through (IX). The first and second substrates of the liquid crystal cell can each be independently selected from those classes and examples of substrates as described previously herein with regard to the optical element of the present invention.

Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. A non-limiting example of an active liquid crystal cell element or device is a liquid crystal display.

The present invention also relates to a method of forming an ophthalmic element, that includes: (i) forming a liquid crystal composition comprising the compound(s) of the present invention, such as represented by Formulas (I) through (IX); (ii) applying the liquid crystal composition to at least a portion of a substrate; (iii) at least partially aligning at least a portion of the liquid crystal composition applied to the substrate, thereby forming an at least partially aligned liquid crystal composition; and (iv) curing, at least partially, the aligned liquid crystal composition.

The liquid crystal composition can be selected from those liquid crystal compositions as described previously herein. The substrate can be selected from those substrates as described previously herein. Application of the liquid crystal composition to the substrate can be conducted in accordance with those application methods described previously herein. Aligning the liquid crystal composition can be achieved in accordance with those methods as described previously herein. The aligned liquid crystal composition can be cured in accordance with those methods as described previously herein, such as by exposure to actinic radiation, high energy particles (e.g., electron beam) and/or elevated temperature. The term "at least partially cured" means the curable or crosslinkable components of the liquid crystal composition are at least partially cured, crosslinked and/or reacted. In alternate non-limiting embodiments, the degree of reacted components, can vary widely, e.g., from 5% to 100% of all the possible curable, crosslinkable and/or reactable components.

The layer of the optical elements of the present invention can include a single layer or multiple layers each including at least one compound of the present invention, that can be the same or different. The layer typically includes an organic matrix, such as a thermoplastic organic matrix and/or a crosslinked organic matrix. Additionally or alternatively to an organic matrix, the layer can include an inorganic matrix, including, for example, silane linkages, siloxane linkages and/or titanate linkages. The organic matrix can include, for example: acrylate residues (or monomer units) and/or methacrylate residues; vinyl residues; ether linkages; sulfide linkages, including monosulfide linkages and/or polysulfide linkages; carboxylic ester linkages; carbonate linkages (e.g., —O—C(O)—O—) urethane linkages (e.g., —N(H)—C(O)—O—); and/or thiourethane linkages (e.g., —N(H)—C(O)—S—).

The layer containing the compound(s) of the present invention can be formed by art-recognized methods including those methods as discussed previously herein. With some embodiments, the layer containing the compound(s) of the present invention can be formed by methods including, but not limited to: lamination, such as of one or more plastic sheets or films; in-mold formation, such as in-mold coating; film casting; and coating methods. With some embodiments, the layer containing the compound(s) of the present invention is formed from a coating composition, that is curable by exposure to, for example: ambient temperatures, such as in the case of two component coating compositions; elevated temperatures (e.g., 150° C. to 190° C. for 5 to 60 minutes), such as in the case of thermally cured coating compositions; or actinic radiation, such as in the case of ultraviolet light curable coating compositions.

The layer containing the compound(s) of the present invention can have any suitable thickness. With some embodiments, the layer has a thickness of from 0.05 microns to 20 microns, such as from 1 to 10 microns, or from 2 to 8 microns, or from 3 to 5 microns, inclusive of the recited values.

With some embodiments, the layer containing the compound(s) of the present invention includes an organic matrix that includes urethane linkages. In accordance with some embodiments, the layer containing urethane linkages is formed from a curable coating composition that includes: a (meth)acrylate copolymer having active hydrogen functionality selected from hydroxyl, thiol, primary amine, secondary amine, and combinations thereof; blocked isocyanate, such as diisocyanate and/or triisocyanate blocked with a suitable blocking or leaving group, such as, 3,5-dimethyl pyrazole; and one or more additives, including, but not limited to those classes and examples as described previously herein with regard to the compositions of the present invention, such as adhesion promoters, coupling agents, ultraviolet light absorbers, thermal stabilizers, catalysts, free radical scavengers, plasticizers, flow additives, and/or static tints or static dyes (i.e., tints or dyes that are not photochromic).

Examples of (meth)acrylate monomers from which the active hydrogen functional (meth)acrylate copolymer can be prepared include, but are not limited to, $C_1$-$C_{20}$ (meth)acrylates, $C_1$-$C_{20}$ (meth)acrylates having at least one active hydrogen group selected from hydroxyl, thiol, primary amine, and secondary amine. The $C_1$-$C_{20}$ groups of the (meth)acrylates can be selected from, for example, $C_1$-$C_{20}$ linear alkyl, $C_3$-$C_{20}$ branched alkyl, $C_3$-$C_{20}$ cycloalkyl, $C_3$-$C_{20}$ fused ring polycycloalkyl, $C_5$-$C_{20}$ aryl, and $C_{10}$-$C_{20}$ fused ring aryl.

Additional polyols that can be used in the compositions of the present invention from which the layer including compound(s) of the present invention is prepared include, but are not limited to, art-recognized materials, such as described in U.S. Pat. No. 7,465,414 at column 15, line 22 through column 16, line 62, which disclosure is incorporated herein by reference. Isocyanates that can be used in the compositions of the present invention from which the layer containing compound(s) of the present invention is prepared include, but are not limited to, art-recognized materials, such as described in U.S. Pat. No. 7,465,414 at column 16, line 63 through column 17, line 38, which disclosure is incorporated herein by reference. Catalysts that can be used in the compositions of the present invention from which the layer containing compounds of the present invention is prepared include, but are not limited to, art-recognized materials, such as described in U.S. Pat. No. 7,465,414 at column 17, lines 39-62, which disclosure is incorporated herein by reference.

The layer containing compound(s) of the present invention, of the optical elements of the present invention, can, with some embodiments, be selected from a primer layer, a protective layer, a photochromic layer, an alignment layer, an antireflective layer, and combinations thereof. A photochromic layer including the compound(s) of the present invention also includes one or more photochromic compounds, which can be selected from those classes and examples of photochromic compounds described previously herein.

With some further embodiments, the optical elements of the present invention include at least one further layer (in addition to the layer that includes compound(s) of the present invention), in which each further layer is selected from a primer layer, a protective layer, a photochromic layer, an alignment layer, and an antireflective layer.

Primer layers, photochromic layers, and protective layers of the optical elements of the present invention can each independently include organic matrices and/or inorganic matrices, including those as described previously herein, and can be formed in accordance with art-recognized methods including those methods described previously herein.

The protective layer(s) of the optical elements of the present invention, with some embodiments, can be selected from an abrasion-resistant layer, such as a "hard coat." Each protective layer can include a single layer or multiple layers, each having the same or a different composition. The protective layer can be formed from a coating selected from abrasion-resistant coatings including organo silanes, abrasion-resistant coatings including radiation-cured acrylate-based thin films, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof. With some embodiments, the protective layer is a hard coat layer that includes a first coating of a radiation-cured acrylate-based thin film and a second coating including an organo-silane. Non-limiting examples of commercially available hard coating products include SILVUE® 124 coatings, commercially available from SDC Coatings, Inc., and HI-GARD® coatings, commercially available from PPG Industries, Inc.

The protective layer can be selected from art-recognized hard coat materials, such as organo-silane abrasion-resistant coatings. Organo-silane abrasion-resistant coatings, often referred to as hard coats or silicone-based hard coatings, are well known in the art, and are commercially available from various manufacturers, such as SDC Coatings, Inc. and PPG Industries, Inc. Reference is made to U.S. Pat. No. 4,756,973 at column 5, lines 1-45; and to U.S. Pat. No. 5,462,806 at column 1, lines 58 through column 2, line 8, and column 3, line 52 through column 5, line 50, which disclosures describe organo-silane hard coatings and which disclosures are incorporated herein by reference. Reference is also made to U.S. Pat. Nos. 4,731,264, 5,134,191, 5,231,156 and International Patent Publication WO 94/20581 for disclosures of organo-silane hard coatings, which disclosures are also incorporated herein by reference. The hard coat layer can be applied by those coating methods as described previously herein with regard to the layer containing the compound(s) of the present invention, such as spin coating.

Other coatings that can be used to form the protective layer, include, but are not limited to, polyfunctional acrylic hard coatings, melamine-based hard coatings, urethane-based hard coatings, alkyd-based coatings, silica sol-based hard coatings or other organic or inorganic/organic hybrid hard coatings.

The protective layer, with some embodiments, is selected from art-recognized organo-silane type hard coatings. Organo-silane type hard coatings from which the protective layer can be selected include, but are not limited to, those disclosed at column 24, line 46 through column 28, line 11 of U.S. Pat. No. 7,465,414 B2, which disclosure is incorporated herein by reference.

Further examples of coating compositions from which the protective layer can be formed, with some embodiments, include but are not limited to: (meth)acrylate based protective coating compositions, such as described in U.S. Pat. No. 7,410,691; radiation curable acrylate based protective coating compositions, such as described in U.S. Pat. No. 7,452,611 B2; thermally cured protective coating compositions, such as described in U.S. Pat. No. 7,261,843; maleimide based protective coating compositions, such as described in U.S. Pat. No. 7,811,480; and dendritic polyester (meth) acrylate based protective coating compositions, such as described in U.S. Pat. No. 7,189,456.

The anti-reflective layer(s) of the optical elements of the present invention can be selected from art-recognized anti-reflective layers, and typically include at least two layers each having a different refractive index. With some embodiments, the anti-reflective layer includes a first layer having a refractive index of from 1.6 to 2.5, or from 1.95 to 2.4, and a second layer having a refractive index of from 1.30 to 1.48, or from 1.38 to 1.48. The anti-reflective layer includes, with some embodiments, a plurality of such alternating first and second layers. With some embodiments, the first layer of the anti-reflective layer includes at least one of, $TiO_2$, $Ti_2O_3$, $Ti_3O_5$, $Pr_6O_{11}+xTiO_2$, $CeO_2$, $HfO_2$, $Ta_2O_5$, $ZrO_2$, and $SnO_2$. With some embodiments, the second layer of the anti-reflective layer includes at least one of, $SiO_2$, $MgF_2$, $AlF_3$, $BaF_2$, $Na_5Al_3F_{14}$, $Na_3AlF_6$, and $YF_3$. Examples of anti-reflective layers from which the anti-reflective layer can be selected are described in U.S. Pat. No. 6,175,450 B1 at column 1, line 56 through column 2, line 7; column 2, lines 50-65; and column 5, lines 22-58, which disclosure is incorporated herein by reference.

The alignment layer of the optical elements of the present invention can also be referred to herein as an orientation facility. With some embodiments, another layer that abuts the alignment layer (such as a dichroic layer or a photochromic-dichroic layer) can be at least partially aligned by interaction with the alignment layer, which with some embodiments is an underlying alignment layer.

As used herein the term "alignment layer" means a layer that can facilitate the positioning of one or more other structures that are exposed, directly and/or indirectly, to at least a portion thereof. As used herein the term "order" means bring into a suitable arrangement or position, such as aligning with another structure or material, or by some other force or effect. Thus, as used herein the term "order" encompasses both contact methods of ordering a material, such as by aligning with another structure or material, and non-contact methods of ordering a material, such as by exposure to an external force or effect. The term order also encompasses combinations of contact and non-contact methods.

For example, the dichroic compound and/or photochromic-dichroic compound that is at least partially aligned by interaction with the alignment layer can be at least partially aligned such that the long-axis of the dichroic compound/photochromic-dichroic compound in the activated state is essentially parallel to at least the first general direction of the alignment layer. With some embodiments, the dichroic compound and/or photochromic-dichroic compound that is at least partially aligned by interaction with the alignment layer is bound to or reacted with the alignment layer. As used herein with reference to order or alignment of a material or structure, the term "general direction" refers to the predominant arrangement or orientation of the material, compound or structure. Further, it will be appreciated by those skilled in the art that a material, compound or structure can have a general direction even though there is some variation within the arrangement of the material, compound or structure, provided that the material, compound or structure has at least one predominate arrangement.

The alignment layer can, with some embodiments, have at least a first general direction. For example, the alignment layer can include a first ordered region having a first general direction and at least one second ordered region adjacent the first ordered region having a second general direction that is different from the first general direction. Further, the alignment layer can have a plurality of regions, each of which has a general direction that is the same or different from the remaining regions so as to form a desired pattern or design. The alignment layer can include, for example, a coating including an at least partially ordered alignment medium, an at least partially ordered polymer sheet, an at least partially treated surface, Langmuir-Blodgett films, and combinations thereof.

The alignment layer can include, with some embodiments, a coating that includes an at least partially ordered alignment medium. Examples of suitable alignment media that can be used in conjunction with the alignment layer include, but are not limited to, photo-orientation materials, rubbed-orientation materials, and liquid crystal materials. Methods of ordering at least a portion of the alignment medium are described herein below in further detail.

The alignment medium of the alignment layer can be a liquid crystal material, and the alignment layer can be referred to as a liquid crystal alignment layer. Liquid crystal materials, because of their structure, are generally capable of being ordered or aligned so as to take on a general direction. More specifically, because liquid crystal molecules have rod- or disc-like structures, a rigid long axis, and strong dipoles, liquid crystal molecules can be ordered or aligned by interaction with an external force or another structure such that the long axis of the molecules takes on an orientation that is generally parallel to a common axis. For example, it is possible to align the molecules of a liquid crystal material with a magnetic field, an electric field, linearly polarized infrared radiation, linearly polarized ultraviolet radiation, linearly polarized visible radiation, or shear forces. It is also possible to align liquid crystal molecules with an oriented surface. For example, liquid crystal molecules can be applied to a surface that has been oriented, for example by rubbing, grooving, or photoalignment methods, and subsequently aligned such that the long axis of each of the liquid crystal molecules takes on an orientation that is generally parallel to the general direction of orientation of the surface. Examples of liquid crystal materials suitable for use as alignment media include, but are not limited to, liquid crystal polymers, liquid crystal pre-polymers, liquid crystal monomers, and liquid crystal mesogens. As used herein the term "pre-polymer" means partially polymerized materials.

Classes of liquid crystal monomers that are suitable for use in conjunction with the alignment layer include, but are not limited to, mono- as well as multi-functional liquid crystal monomers. The liquid crystal monomers can, with some embodiments, be selected from cross-linkable liquid crystal monomers, such as photocross-linkable liquid crystal monomers. As used herein the term "photocross-linkable" means a material, such as a monomer, a pre-polymer or a polymer, that can be cross-linked on exposure to actinic radiation. For example, photocross-linkable liquid crystal monomers include, but are not limited to, those liquid crystal monomers that are cross-linkable on exposure to ultraviolet radiation and/or visible radiation, either with or without the use of polymerization initiators.

Examples of cross-linkable liquid crystal monomers, that can be included in the alignment layer, include, but are not limited to, liquid crystal monomers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers and blends thereof. Examples of photocross-linkable liquid crystal monomers, that can be included in the alignment layer, include, but are not limited to, liquid crystal monomers having functional groups chosen from acrylates, methacrylates, alkynes, epoxides, thiols, and blends thereof.

Liquid crystal polymers and pre-polymers, that can be included in the alignment layer, include, but are not limited to, main-chain liquid crystal polymers and pre-polymers and side-chain liquid crystal polymers and pre-polymers. With main-chain liquid crystal polymers and pre-polymers, rod- or disc-like liquid crystal mesogens are primarily located within the polymer backbone. With side-chain liquid crystal polymers and pre-polymers, the rod- or disc-like liquid crystal mesogens primarily are located within the side chains of the polymer. Additionally, the liquid crystal polymer or pre-polymer can be cross-linkable, and further can be photocross-linkable.

Examples of liquid crystal polymers and pre-polymers, that can be included in the alignment layer, include, but are not limited to, main-chain and side-chain polymers and pre-polymers having functional groups chosen from acrylates, methacrylates, allyl, allyl ethers, alkynes, amino, anhydrides, epoxides, hydroxides, isocyanates, blocked isocyanates, siloxanes, thiocyanates, thiols, urea, vinyl, vinyl ethers, and blends thereof. Examples of photocross-linkable liquid crystal polymers and pre-polymers, that can be included in the alignment layer, include, but are not limited to, those polymers and pre-polymers having functional groups chosen from acrylates, methacrylates, alkynes, epoxides, thiols, and blends thereof.

Liquid crystal mesogens, that can be included in the alignment layer, include, but are not limited to, thermotropic liquid crystal mesogens and lyotropic liquid crystal mesogens. Additional classes of liquid crystal mesogens, that can be included in the alignment layer, include, but are not limited to, columatic (or rod-like) liquid crystal mesogens and discotic (or disc-like) liquid crystal mesogens.

Examples of photo-orientation materials, that can be included in the alignment layer, include, but are not limited to, photo-orientable polymer networks. More specific examples of photo-orientable polymer networks include, but are not limited to, azobenzene derivatives, cinnamic acid derivatives, coumarine derivatives, ferulic acid derivatives, and polyimides. With some embodiments, the alignment layer can include an at least partially ordered photo-orientable polymer network chosen from azobenzene derivatives, cinnamic acid derivatives, coumarine derivatives, ferulic acid derivatives, and/or polyimides. Examples of cinnamic acid derivatives, that can be included in the alignment layer, include, but are not limited to, polyvinyl cinnamate and polyvinyl esters of paramethoxycinnamic acid.

As used herein the term "rubbed-orientation material" means a material that can be at least partially ordered by rubbing at least a portion of a surface of the material with another suitably textured material. For example, the rubbed-orientation material can be rubbed with a suitably textured cloth or a velvet brush. Examples of rubbed-orientation materials, that can be included in the alignment layer, include, but are not limited to, (poly)imides, (poly)siloxanes, (poly)acrylates, and (poly)coumarines. With some embodiments, the alignment layer can include a polyimide, and the alignment layer can be rubbed with a velvet or a cotton cloth so as to at least partially order at least a portion of the surface of the alignment layer.

With some embodiments, the alignment layer can include an at least partially ordered polymer sheet. For example, a sheet of polyvinyl alcohol can be at least partially ordered by stretching (e.g., uniaxially stretching) the sheet, and thereafter the stretched sheet can be bonded to the at least a portion a surface of the optical substrate to form the orientation facility. Alternatively, the ordered polymer sheet can be made by a method that at least partially orders the polymer chains during fabrication, for example, by extrusion. Further, the at least partially ordered polymer sheet can be formed by casting or otherwise forming a sheet of a liquid crystal material and thereafter at least partially ordering the sheet for example, but exposing the sheet to a magnetic field, an electric field, and/or a shear force. Still further, the at least partially ordered polymer sheet can be made using photo-orientation methods. For example, a sheet of a photo-orientation material can be formed, for example by casting, and thereafter at least partially ordered by exposure to linearly polarized ultraviolet radiation.

The alignment layer of the photochromic articles of the present invention can include an at least partially treated surface. As used herein, the term "treated surface" refers to at least a portion of a surface that has been physically altered to create at least one ordered region on least a portion of the surface. Examples of treated surfaces include, but are not limited to, rubbed surfaces, etched surfaces, and embossed surfaces. Further, the treated surfaces can be patterned, for example using a photolithographic or an interferographic process. With some embodiments, the surface of the alignment layer can be a treated surface selected from, for example, chemically etched surfaces, plasma etched surfaces, nanoetched surfaces (such as surfaces etched using a scanning tunneling microscope or an atomic force microscope), laser etched surfaces, and/or electron-beam etched surfaces.

In accordance with some embodiments, when the alignment layer includes a treated surface, the treated surface can be formed by depositing a metal salt (such as a metal oxide or metal fluoride) onto at least a portion of a surface (e.g., a surface of the alignment layer itself, or a surface of the primer layer), and thereafter etching the deposit to form the treated surface. Art-recognized methods of depositing a metal salt include, but are not limited to, plasma vapor deposition, chemical vapor deposition, and sputtering. Etching can be undertaken in accordance with art-recognized methods, such as those described previously herein.

As used herein the term "Langmuir-Blodgett films" means one or more at least partially ordered molecular films on a surface. Langmuir-Blodgett films can be formed, for example, by dipping a substrate into a liquid one or more times so that it is at least partially covered by a molecular film and then removing the substrate from the liquid such that, due to the relative surface tensions of the liquid and the substrate, the molecules of the molecular film are at least partially ordered in substantially one (or a single) general direction. As used herein, the term molecular film refers to monomolecular films (i.e., monolayers) as well as films comprising more than one monolayer.

The articles and optical elements of the present invention can, with some embodiments, further include an alignment transfer material interposed between the alignment layer and the layer it is meant to align, such as a dichroic layer or a photochromic-dichroic layer. The alignment transfer material can be aligned by interaction with the alignment layer, and correspondingly the dichroic compound and/or photochromic-dichroic compound can be aligned by interaction with the alignment transfer material. The alignment transfer material can, with some embodiments, facilitate the propagation or transfer of a suitable arrangement or position from the alignment layer to the dichroic compound and/or photochromic-dichroic compound of the adjacent layer.

Examples of alignment transfer materials include, but are not limited to, those liquid crystal materials described above in connection with the alignment media disclosed herein. It is possible to align the molecules of a liquid crystal material with an oriented surface. For example, a liquid crystal material can be applied to a surface that has been oriented and subsequently aligned such that the long axis of the liquid crystal molecules adopts an orientation that is generally parallel to the same general direction of orientation of the surface. The liquid crystal material of the alignment transfer material can be at least partially ordered by alignment with the alignment layer, such that the long axis of the molecules of the liquid crystal material are generally parallel to, for example, a first general direction of the orientation facility. In this manner, the general direction of the alignment layer can be transferred to the liquid crystal material, which in turn can transfer the general direction to another structure or material. Further, if the alignment layer includes a plurality of regions having general directions that together form a design or pattern, that design or pattern can be transferred to the liquid crystal material by aligning the liquid crystal material with the various regions of the alignment layer. Additionally, although not required, according to various non-limiting embodiments disclosed herein, at least a portion of the liquid crystal material of the alignment transfer material can be exposed to at least one of, a magnetic field, an electric field, linearly polarized infrared radiation, linearly polarized ultraviolet radiation, and linearly polarized visible radiation while being at least partially aligned with at least a portion of the alignment layer.

With some embodiments of the present invention, the layer of the optical element which includes a compound(s) of the present invention, further includes at least one photochromic-dichroic compound and optionally at least one photochromic compound (that is not dichroic), and the layer is a photochromic layer or a photochromic-dichroic layer. Classes and examples of photochromic-dichroic compound(s) that can be included in the layer include, but are not limited to, those classes and examples of photochromic-dichroic compounds described previously herein.

The photochromic-dichroic compound and optional photochromic compound can be present in the layer of the optical element of the present invention in amounts or ratios such that the optical element exhibits a desired color or colors, either in an activated state (e.g., colored state) or a non-activated state (e.g., a bleached state). Thus the amount of the photochromic-dichroic and optional photochromic compounds used is not critical provided that a sufficient amount is present to produce a desired photochromic effect and dichroic effect. As used herein, the term "photochromic amount" refers to the amount of photochromic compound (whether a photochromic-dichroic compound and/or a photochromic compound that is not dichroic) necessary to produce the desired photochromic effect. With some embodiments the photochromic-dichroic compound and optional photochromic compound is/are present in the layer of the optical element in an amount of from 0.1 to 40 percent by weight, based on the total weight of the layer.

In accordance with some further embodiments of the optical elements of the present invention, the layer that includes a compound(s) of the present invention further includes a fixed tint, and the layer is a dichroic layer. The layer containing the compound(s) of the present invention and a fixed tint can, with some embodiments, further include one or more dichroic compounds. Classes and examples of fixed tints and optional dichroic compounds that can be included in the layer of the optical elements of the present invention include, but are not limited to those classes and examples of fixed tints and dichroic compounds described previously herein.

The optical element with some embodiments of the present invention includes in the following sequence: an optical substrate; a primer layer; an alignment layer; a photochromic-dichroic layer; a top-coat layer; and a protective layer, which can be a hard-coat layer, in which at least one layer thereof includes one or more compounds of the present invention.

The optical element with some embodiments of the present invention includes in the following sequence: an optical substrate; a primer layer; an alignment layer; a fixed tint layer that optionally further includes a dichroic compound; a top-coat layer; and a protective layer, which can be a hard-coat layer, in which at least one layer thereof includes one or more compounds of the present invention.

The present invention is more particularly described in the following examples, which are intended as illustrative only, since numerous modifications and variations therein will be apparent to those skilled in the art.

EXAMPLES

In PART-A of the Examples, the synthesis of compounds according to the present invention is described in Examples 1-30.

In PART-B of the Examples, the evaluation of compounds according to the present invention is described in coating compositions and coated articles.

Part-A

Example 1

Step 1

4-((tetrahydro-2H-pyran-2-yl)oxy)phenol was synthesized by the method published in Macromolecules 1995, 28, 3313-3327 except following neutralization with acetic acid, the suspension was stored overnight at −18° C. and then allowed to warm to 0° C. to obtain a light brown solid.

Step 2

To a reaction flask containing a suspension of the product of Step 1 (242.4 g, 1285.4 mmol), trans,trans-4-pentyl-[1,1'-bi(cyclohexane)]-4-carboxylic acid (360.4 g, 1248 mmol), and N,N-dimethylamino pyridine (15.2 g, 124.8 mmol) in 2.5 L of dichloromethane was added N,N'-dicyclohexylcarbodiimide (282.8 g, 1372.8 mmol) while stirring under nitrogen. The reaction was followed by HPLC, which indicated the reaction was complete within 2-3 hours. The reaction was stirred overnight then diluted with additional dichloromethane (1 L), whereafter the byproduct N,N'-dicyclohexylurea was removed by filtration. The filtrate was passed through a short pad of silica gel using dichloromethane as eluent. The resultant solution was washed 3 times with 300 mL 10% HCl then dried over anhydrous $MgSO_4$. After subsequent filtration, removal of the solvent of the filtrate gave a light brown solid that was used directly for the next step without further purification.

Step 3

To a reaction flask containing a suspension of the product from Step 2 in 700 mL of THF and 100 mL of ethanol was added 10 mL of concentrated (36%) HCl drop-wise. The reaction mixture was gently stirred in a 35° C. water bath for 10 minutes. The resultant solution was quickly added to an excess of ice-cold water. The precipitate was collected by filtration and rinsed with deionized water. The crude product was crystallized from THF/ethanol (1:1, v/v). The solid thus obtained was dried under vacuum for 3 h at 60° C. to yield 410 g of a white crystalline powder. NMR showed that the product had a structure consistent with 4-hydroxyphenyl trans, trans-4'-pentyl-[1,1'-bi(cyclohexane)]-4-carboxylate.

Step 4

A suspension of methyl 4-hydroxy benzoate (6.40 Kg, 42.08 mol), 8-chloro-1-octanol (7.60 Kg, 46.08 mol), sodium iodide hydrate (780.8 g, 4.22 mol) and anhydrous sodium carbonate (17.42 Kg, 126.24 mol) in 32 L of Dimethylacetamide was stirred and heated to about 110° C. for 10 hours. The solution was cooled to room temperature and filtered. The solid was washed with 3 L of dimethylacetamide. The filtrate was poured into 200 L of water under stirring. A white solid was obtained upon filtration, rinsed with distilled water, and used in the next step without further purification.

Step 5

To a reaction flask containing the product from Step 4 was added sodium hydroxide (4.03 Kg, 100.96 mol) and 40 L of ethanol. The mixture was heated to reflux for 4 hours. The solution was cooled to room temperature and acidified by 30 L of 3 N HCl solution to pH 6-7. A large amount of white solid was formed. The solid was filtered and washed with distilled water and dried to give 9.60 Kg of product in a form of white solids. NMR showed that the product had a structure consistent with 4-(8-hydroxyoctyloxy)benzoic acid.

Step 6

To a reaction flask containing a suspension of the product of Step 5 (6650 g, 25.00 mol), p-toluenesulfonic acid (47.5 g, 0.25 mol) and 27.5 L of THF was added dihydropyran (2.750 L, 30.00 mol) over 1 hour with stirring. The reaction mixture was stirred for 24 hours at room temperature. The solution was filtrated through a diatomaceous earth pad. The filtrate was concentrated and then poured into 10 L of petroleum ether. The precipitates were collected by filtration and dried in vacuum to yield a white solid (5.5 Kg). NMR showed that the product had a structure consistent with 4-(8-(tetrahydro-2H-pyran-2-yloxy)octyloxy)-benzoic acid.

Step 7

To a reaction flask containing 4-hydroxyphenyl trans, trans-4'-pentyl-[1,1'-bi(cyclohexane)]-4-carboxylate (175 g, 469.74 mmol), the product of Step 6 (164.6 g, 469.74 mmol) and 4-dimethylaminopyridine (5.73 g, 46.97 mmol) in 1.5 L of dichloromethane was added N,N'-dicyclohexylcarbodiimide (101.8 g, 493.23 mmol) while stirring under argon. The reaction was stirred overnight then diluted with 0.5 L of dichloromethane. The N,N'-dicyclohexylurea byproduct was removed by filtration and washed with 0.5 L of dichloromethane. The solution was passed through a short pad of silica gel. The resultant solution was washed with 10% HCl (2×250 mL) and brine (2×250 mL) and dried over anhydrous magnesium sulfate. After filtration, the removal of the solvent offered a product which was used directly for the next step without further purification.

Step 8

To a reaction flask containing the product from Step 7 above (331.2 g) in 500 mL of ethanol and 1000 mL of THF, was added 8.94 g of p-toluenesulfonic acid. The resulting mixture was heated to 65° C. and stirred for 4 hrs under a nitrogen atmosphere, followed by addition of 500 mL of acetonitrile. The reaction mixture was heated to 70° C. and filtered to remove insolubles (~1-2 grams). Some extra THF (about 200 mL) was used to rinse the filter paper. The solution was heated to 70° C., cooled to room temperature for 4 hours and then refrigerated overnight. The formed precipitate was collected by filtration. Recrystallization from THF/acetonitrile (1/1, v/v) twice yielded a white crystalline solid (216.8 g). NMR showed that the product had a structure consistent with 4-((4-((8-hydroxyoctyl)oxy)benzoyl) oxy)phenyl trans, trans-4'-pentyl-[1,1'-bi(cyclohexane)]-4-carboxylate.

Step 9

To a reaction flask containing a solution of the product of step 8 (30.00 g, 48.32 mmol) and tosyl chloride (9.21 g, 48.32 mmol) in 300 mL of dichloromethane was added triethylamine (9.78 g, 96.64 mmol) and pyridine (7.64 g, 96.64 mmol). The resulting mixture was stirred at room temperature under nitrogen atmosphere overnight. The precipitates that formed during the reaction were discarded by filtration. The filtrate was washed with 1N HCl (100 mL×3) and brine (50 mL×2) and dried over anhydrous magnesium sulfate. After filtration, the removal of the solvent offered a crude product which was run through a silica plug eluting with dichloromethane to afford the product, which was purified by recrystallization from acetonitrile/THF (2/1, v/v) to yield a white solid (33.0 g). NMR showed that the product had a structure consistent with 4-((4-((8-(tosyloxy)octyl) oxy)benzoyl)oxy)phenyl trans, trans-4'-pentyl-[1,1'-bi(cyclohexane)]-4-carboxylate.

Step 10

To a reaction flask containing the product of Step 9 above (8.00 g, 10.32 mmol), 2,4-dihydroxybenzophenone (3.32 g, 15.48 mmol) and potassium carbonate (4.31 g, 30.97 mmol) was added 200 mL of DMF. The resulting mixture was heated in a 70° C. oil bath and stirred for two hours under nitrogen. When the reaction was complete as indicated by HPLC, the reaction mixture was poured into 500 mL of water. The formed precipitate was collected by filtration and dried in air overnight. The crude product was purified by recrystallization from acetonitrile/THF (1/1, v/v) to afford a white solid (5.1 g). NMR showed that the product had a structure consistent with 4-((4-((8-(4-benzoyl-3-hydroxyphenoxy)octyl)oxy)benzoyl)oxy)phenyl 4'-pentyl-[trans, trans-1,1'-bi(cyclohexane)]-4-carboxylate, as represented by the following formula.

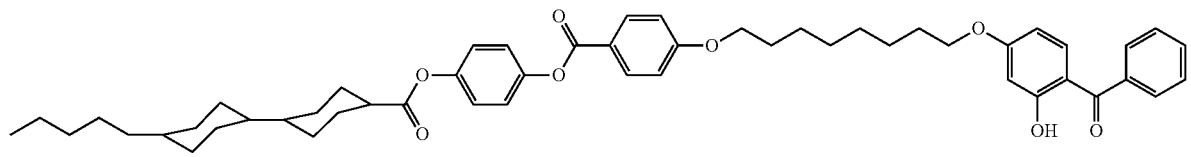 [SMILES: CCCCCC1CCC(C2CCC(C(=O)Oc3ccc(OC(=O)c4ccc(OCCCCCCCCOc5ccc(C(=O)c6ccccc6)c(O)c5)cc4)cc3)CC2)CC1]

Example 2

Step 1

To a reaction flask containing 2-methylhydroquinone (189 g) and ferric sulfate hydrate (12.18 g) was added 1 L of diethyl ether. Dihydropyran (160.08 g) was added dropwise. The resulting solution was stirred overnight at room temperature under nitrogen. After filtration, sodium hydroxide (67.5 g) in water (750 mL) was added to the filtrate and the aqueous phase was acidified by addition of dry ice cubes over two days. The formed precipitate was collected by filtration, washed with deionized water and dried in a vacuum oven to yield a brown solid (160 g). NMR showed that the product had a structure consistent with 2,3-methyl-4-((tetrahydro-2H-pyran-2-yl)oxy)phenol.

Step 2

The procedures of Example 1 were followed, with the exception that an equimolar amount of 2,3-methyl-4-((tetrahydro-2H-pyran-2-yl)oxy)phenol was used in place of 4-((tetrahydro-2H-pyran-2-yl)oxy)phenol in step 7. The crude product was recrystallized in dichloromethane to yield a pale brown solid. NMR showed that the product had a structure consistent with 4-((4-((8-(4-benzoyl-3-hydroxyphenoxy)octyl)oxy)benzoyl)oxy)-2-methylphenyl 4'-pentyl-[trans,trans-1,1'-bi(cyclohexane)]-4-carboxylate, as represented by the following formula.

iodide (5.1 g, 31.0 mmol) in Dimethylacetamide (500 mL) was added potassium carbonate (128.5 g, 930.0 mmol). The reaction was stirred at 90° C. overnight under nitrogen. Chlorohexanol (10 g) was added and the reaction stirred an additional 40 hours at 90° C. The resultant suspension was added to cold water (2.5 L). The precipitate was filtered off and washed with water. The solid residue was dissolved in dichloromethane (0.5 L) and washed with brine (200 mL×1), HCl (200 mL×2) then again with brine (200 mL×1) and dried over anhydrous magnesium sulfate. The solution was passed through a short pad of silica gel using dichloromethane/ethyl acetate (80/20, v/v) as eluent to give a product which was further purified by recrystallization from a mixture of acetonitrile and THF (2/1; v/v) to yield slightly tinted crystals (95 g). NMR showed that the product had a structure consistent with 6-((4'-(trans-4-pentylcyclohexyl)-[1,1'-biphenyl]-4-yl)oxy)hexane-1-ol.

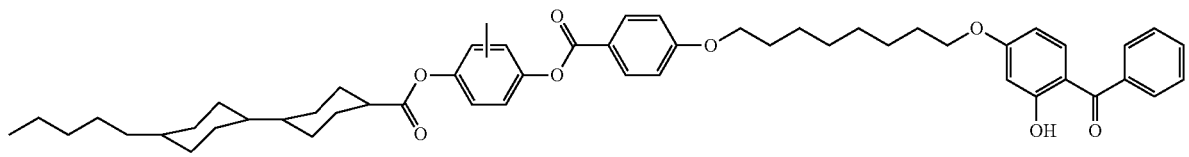

Example 3

Step 1

Under nitrogen in an appropriate reaction flask, a mixture of 1-bromo-4-(trans-4-pentylcyclohexyl)benzene (43.31 g, 0.285 mol), 4-methoxyphenylboronic acid (88.1 g, 0.285 mol), dimethyl ethylene glycol (500 mL), tetrakistriphenylphosphine palladium (0) (1.64 g, 1.4 mmol), sodium carbonate (121 g, 1.14 mol) and water (570 mL) was degassed and then refluxed for 4 hours. After cooling to room temperature, dichloromethane (1 L) and water (500 mL) were added. The organic layer was separated, dried over anhydrous MgSO₄, filtered and concentrated. Recrystallization from ethyl acetate (EtOAc) yielded white crystals (82 g). NMR showed that the product had a structure consistent with 4-methoxy-4'-(trans-4-pentylcyclohexyl)biphenyl.

Step 2

The product of Step 1, (80 g), and pyridine hydrochloride (300 g) were added to a reaction flask and heated to 200° C. for one hour. The resulting mixture was poured into water while hot. The product separated out as an oil. The water was decanted and the product was dissolved in methylene chloride, washed with water and a saturated sodium bicarbonate water solution several times, dried over anhydrous MgSO₄ and then concentrated. The concentrated product was recrystallized using ethanol yielding white crystals (75 g). NMR showed that the product had a structure consistent with 4-hydroxy-4'-(trans-4-pentylcyclohexyl)biphenyl.

Step 3

To a reaction flask containing a mixture of 6-chlorohexan-1-ol (63.5 g, 465.12 mmol), 4'-(trans-4-pentylcyclohexyl)-[1,1'-biphenyl]-4-ol (100 g, 310.08 mmol) and potassium Step 4

Pyridine (37 g, 473 mmol) was added to a solution of the product of step 3 above (50 g, 118.3 mmol) and p-toluenesulfonyl chloride (34 g, 177 mmol) in 250 ml of dichloromethane in a round-bottomed flask at room temperature. After stirring 24 h, the reaction mixture was poured into a saturated ammonium chloride solution (500 mL). The aqueous phase was extracted with dichloromethane (150 mL×2). The combined organic phase was washed with brine solution (100 mL×2) and dried over anhydrous magnesium sulfate. After filtration, the filtrate was concentrated to about 150 mL and purified using a short pad of silica gel and diatomaceous earth on top eluted with dichloromethane/ethyl acetate (9/1, v/v) to give a product which was further purified by precipitation from ethyl acetate and ethanol (1/8, v/v) at −10° C. Yield: 60 g. NMR showed that the product had a structure consistent with 6-((4'-(4-pentylcyclohexyl)-[1,1'-biphenyl]-4-yl)oxy)hexyl 4-methylbenzenesulfonate.

Step 5

The procedure of Step 10 of Example 1 was followed except an equimolar amount of the product of step 4 above was used in place of trans, trans-4-((4-((8-(tosyloxy)octyl)oxy)benzoyl)oxy)phenyl 4'-pentyl-[1,1'-bi(cyclohexane)]-4-carboxylate and acetone was used as solvent. A catalytic amount of KI was added to expedite the reaction which took roughly two days. Recrystallization from ethyl acetate yielded light yellow needles. NMR showed that the product had a structure consistent with (2-hydroxy-4-((6-((4'-(trans-4-pentylcyclohexyl)-[1,1'-biphenyl]-4-yl)oxy)phenyl)(phenyl)methanone, as represented by the following formula.

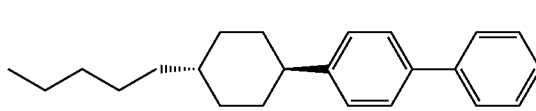

Example 4

To reaction flask containing a mixture of 6-((4'-(4-pentylcyclohexyl)-[1,1'-biphenyl]-4-yl)oxy)hexyl 4-methylbenzene sulfonate (8 g, 13.86 mmol), bis(2,4-dihydroxyphenyl)methanone (5.1 g, 20.86 mmol) and a catalytic amount of tetrabutylammonium iodide (0.5 g) in 2-butanone (100 mL) was added potassium carbonate (4 g, 28.0 mmol). The reaction was stirred overnight at 70° C. under nitrogen. The resultant suspension was added to water (about 200 mL), extracted twice with EtOAc/THF (4/1, v/v) (200 mL×2). The combined organic phases were washed with water (100 mL×2), brine (100 mL×2) and dried over anhydrous magnesium sulfate. After filtration, the removal of the solvent gave a product which was purified with a CombiFlash® purifier on silica gel eluting with gradient dichloromethane/ethyl acetate, followed by recrystallization from ethyl acetate to yield a light yellow solid (4.8 g). NMR showed that the product had a structure consistent with (2,4-dihydroxyphenyl)(2-hydroxy-4-((6-((4'-(4-pentylcyclohexyl)-[1,1'-biphenyl]-4-yl)oxy)hexyl)oxy)phenyl)methanone, as represented by the following formula.

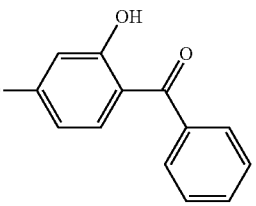

(50 g, 163.77 mmol) (50 g in 100 mL of dichloromethane) dropwise over a period of 30 min at −78° C. The resultant solution was slowly warmed to room temperature and stirring continued overnight. Saturated aqueous NaCl (150 mL) solution was carefully added to the reaction mixture while stirring. After phases were separated, the organic phase was retained and the aqueous layer was extracted with dichloromethane (2×200 mL). The organic extracts were combined, washed twice with brine (100 mL) and dried over anhydrous magnesium sulfate. After removal of the solids and evaporation of the solvent, the filtrate offered a product which was purified by combiflash on silica gel eluting with dichloromethane/ethyl acetate (EtOAc) (90/10, v/v). The product thus obtained was a light yellow solid, used directly for the next step. NMR showed that the product had a structure consistent with (2,4-dihydroxyphenyl)(2-hydroxyphenyl)methanone.

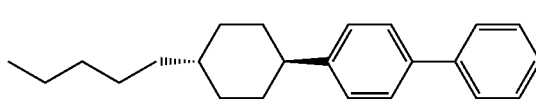

Example 5

Step 1

To reaction flask charged with a suspension of (2-hydroxy-4-methoxyphenyl)(2-hydroxyphenyl)methanone (24 g, 81.88 mmol) in 50 mL dichloromethane, was added $BBr_3$

Step 2

The procedure of example 4 was followed except an equimolar amount of (2,4-dihydroxyphenyl)(2-hydroxyphenyl)methanone was used in place of bis(2,4-dihydroxyphenyl)methanone. The product was obtained in a form of light yellow solids. NMR showed that the product had a structure consistent with (2-hydroxy-4-((6-((4'-(4-pentylcyclohexyl)-[1,1'-biphenyl]-4-yl)oxy)hexyl)oxy)phenyl)(2-hydroxyphenyl)methanone, as represented by the following formula.

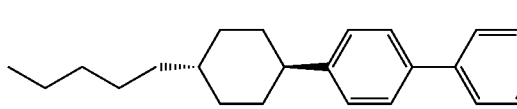
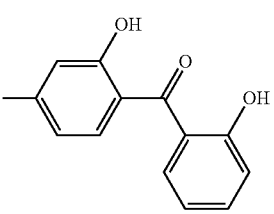
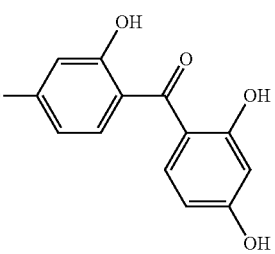

Example 6

Step 1
In a reaction flask charged with a suspension of bis(2,4-dihydroxyphenyl)methanone (15 g, 60.92 mmol), Iodomethane (8.65 g, 60.92 mmol) in butan-2-one (100 mL) at room temperature, was added $Cs_2CO_3$ (23.8 g, 73.1 mmol). The reaction was stirred for 48 hours, after which time HPLC indicated incomplete reaction with some impurities. 200 mL of water was added to the flask and the resulting mixture was extracted twice with ethyl acetate (100 mL). The combined organic extracts were washed twice with brine (100 mL). Evaporation of solvent gave a product which was purified via combiflash on silica gel eluting with dichloromethane/ethyl acetate (90/10, v/v) to give the final product in a form of light yellow solid. NMR showed that the product had a structure consistent with (2,4-dihydroxyphenyl)(2-hydroxy-4-methoxyphenyl)methanone.

Step 2
The procedure of example 4 was followed except an equimolar amount of (2,4-dihydroxyphenyl)(2-hydroxy-4-methoxyphenyl)methanone was used in place of bis(2,4-dihydroxyphenyl)methanone. The product was obtained in a form of light yellow solids. NMR showed that the product had a structure consistent with (2-hydroxy-4-((6-((4'-(4-pentylcyclohexyl)-[1,1'-biphenyl]-4-yl)oxy)hexyl)oxy)phenyl)(2-hydroxy-4-methoxyphenyl)methanone, as represented by the following formula, as represented by the following formula.

phase was recovered and cooled to room temperature. The resulting precipitate was filtered and dried at 50° C. to yield a white solid (650 g). NMR showed that the product had a structure consistent with 4-hydroxyphenyl 4-methylbenzoate.

Step 2
The procedures of Steps 7 to 8 of Example 1 were followed except the product of step 1 above was used in place of 4-hydroxyphenyl trans, trans-4'-pentyl-[1,1'-bi(cyclohexane)]-4-carboxylate in Step 7. A white solid was recovered as the product. NMR showed that the product had a structure consistent with 4-((4-((8-hydroxyoctyl)oxy)benzoyl)oxy)phenyl 4-methylbenzoate.

Step 3
The procedure of Step 4 of Example 3 was followed except an equimolar amount of the product of step 2 above was used in place of 4-(6-hydroxyhexyloxy)-4'-(trans-4-pentylcyclohexyl)biphenyl. The product was obtained in a form of white solids. NMR showed that the product had a structure consistent with 4-((4-methylbenzoyl)oxy)phenyl 4-((8-tosyloxy)octyl)oxy)benzoate.

Step 4
To a reaction flask containing a mixture of the product of step 3 above (10 g, 15.85 mmol), 2,4-dihydroxybenzophenone (3.73 g, 17.44 mmol) and a catalytic amount of tetrabutylammonium iodide (0.25 g) in 2-butanone (100 ml) was added potassium carbonate (4.4 g, 32 mmol). The reaction was stirred at 70° C. overnight under nitrogen. The resultant suspension was added to cold water (200 mL). The precipitated product was filtered and washed it with water.

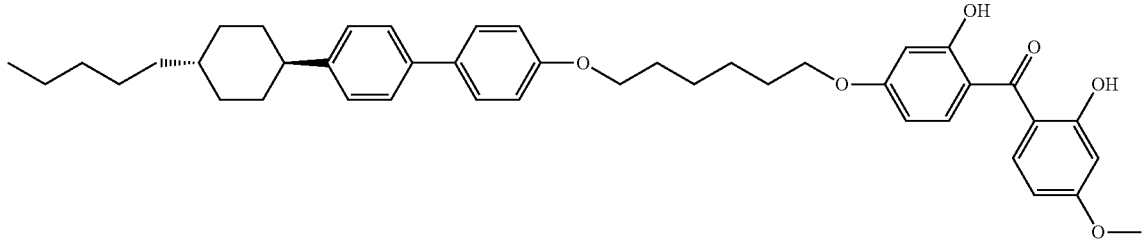 [SMILES: CCCCC[C@H]1CC[C@H](c2ccc(-c3ccc(OCCCCCCOc4ccc(C(=O)c5ccc(OC)cc5O)c(O)c4)cc3)cc2)CC1]

Example 7

Step 1
To a 10 L reaction flask containing 6 L of distilled water at room temperature was added hydroquinone (660 g, 6 mol) and sodium carbonate (636 g, 6 mol). To the resulting mixture was added 4-methylbenzoic chloride (773 g, 5 mol) dropwise under nitrogen. The resulting suspension was stirred for 4 hours at room temperature. The precipitate that formed was filtered, washed with distilled water (6 L), dissolved in a mixture of chloroform (6 L) and distilled water (1 L), and heated to 50° C. with stirring. The organic The aqueous layer was extracted twice with ethyl acetate/THF (411, v/v) (150 mL×2), and the collected solids were dissolved in the combined organic phases that were washed with water (100 mL×2) and brine (100 mL×2), dried over anhydrous magnesium sulfate. The removal of the solvent gave a residue which was passed through a short pad of silica gel using dichloromethane as eluent. The crude product was crystallized once from ethyl acetate to yield a light yellow solid. Yield: 5.0 g. NMR showed that the product had a structure consistent with 4-((4-((8-(4-benzoyl-3-hydroxyphenoxy)octyl)oxy)benzoyl)oxy)phenyl 4-methylbenzoate, as represented by the following formula.

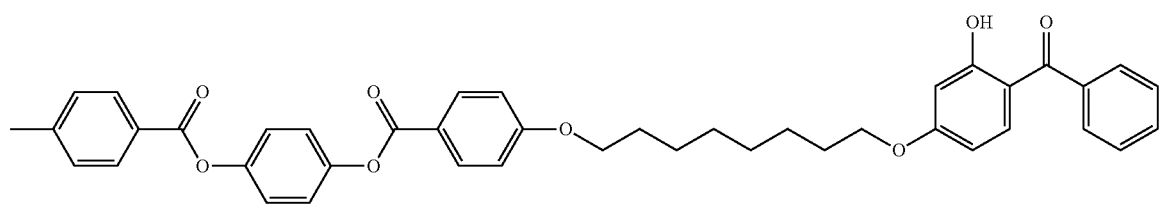 [SMILES: Cc1ccc(C(=O)Oc2ccc(OC(=O)c3ccc(OCCCCCCCCOc4ccc(C(=O)c5ccccc5)c(O)c4)cc3)cc2)cc1]

Example 8

Step 1

The procedure of Step 4 of Example 3 was followed except an equimolar amount of 4-((4-((6-(acryloylxy)hexyl)oxy)benzoyl)oxy)phenyl 4-((8-hydroxyoctyl)oxy)benzoate, made in accordance with example 3 in U.S. Pat. No. 8,349,210, was used in place of 4-(6-hydroxyhexyloxy)-4'-(trans-4-pentylcyclohexyl)biphenyl. The product was obtained in a form of white solids. NMR showed that the product had a structure consistent with 4-((4-((6-(acryloyloxy)hexyl)oxy)benzoyl)oxy)phenyl 4-((8-(tosyloxy)octyl)oxy)benzoate.

Step 2

To reaction flask containing a mixture of the product of step 1 above (10 g, 12.7 mmol), 2,4-dihydroxybenzophenone (3.0 g, 13.97 mmol) and a catalytic amount of tetrabutylammonium iodide (0.25 g) in 2-butanone (100 ml) was added potassium carbonate (3.6 g, 26 mmol). The reaction was stirred at 70° C. overnight under nitrogen protection. The resultant suspension was added to cold water (200 mL). The precipitated product was filtered and washed it with water. The aqueous layer was extracted twice with ethyl acetate (200 mL×2), and the collected solids were dissolved in the combined organic phases that were washed with water (100 mL×2) and brine (100 mL×2), dried over anhydrous magnesium sulfate. The removal of the solvent gave a product which was purified by a short pad of silica gel using dichloromethane as eluent and recrystallization one time from ethyl acetate to give the final product in a form of slightly yellow solids. Yield: 5.0 g. NMR showed that the product had a structure consistent with 4-((4-((6-(acryloyloxy)hexyl)oxy)benzoyl)oxy)phenyl-4-((8-(4-benzoyl-3-hydroxyphenoxy)octyl)oxy)benzoate, as represented by the following formula.

Example 9

The procedure of example 4 was followed except an equimolar amount of 1-(2,4-dihydroxyphenyl)ethane-1-one was used in place of bis(2,4-dihydroxyphenyl)methanone. The product was obtained in a form of white crystals. NMR showed that the product had a structure consistent with 1-(2-hydroxy-4-((6-((4'-(trans-4-pentylcyclohexyl)-[1,1'-biphenyl]-4-yl)oxy)hexyl)oxy)phenyl)ethane-1-one, as represented by the following formula.

Example 10

Step 1

In a reaction flask, 4-((6-(Acryloyloxy)hexyl)oxy)benzoic acid (150.02 g, 513.19 mmol), methyl-4-((tetrahydro-2H-pyran-2-yl)oxy)phenol (107.93 g, 518.26 mmol), BHT (1.13 g, 5.13 mmol), and 4-dimethylaminopyridine (6.27 g, 51.32 mmol) were dissolved in dichloromethane (700 mL) and cooled on ice before N,N'-dicyclohexylcarbodiimide (118.24 g, 573.07 mmol) was added in one portion. After stirring overnight at room temperature under nitrogen, the N,N'-dicyclohexylurea was filtered off and the filtrate was filtered through a plug of silica using dichloromethane as the eluent. The removal of the solvent offered a product in a form of brown oil which was used directly for the next step without further purification.

Step 2

A solution of the product from Step 1 (1800 g, 3.73 mol), AlCl$_3$-6H$_2$O (80 g, 0.33 mol) and methanol (5 L) was heated to reflux for 24 hours. Water (1.5 L) was added to the reaction mixture which was then cooled and at 0° C. for 5 h. Filtration yielded a gray solid (1005 g). NMR showed that the product had a structure consistent with 4-hydroxy-2/3-methylphenyl 4-((6-(acryloyloxy)hexyl)oxy)benzoate.

Step 3

To a reaction flask containing 6500 mL of tetrahydrofuran (THF) was added TsOH (17.13 g, 0.09 mol) and 4-((6-hydroxyhexyl)oxy)benzoic acid. The resulting suspension was stirred at room temperature and dihydropyran (984 ml, 10.80 mol) was added drop-wise over one hour, then heated to 50° C. After stirring for 24 hours at this temperature, dihydropyran (654 ml, 7.17 mol) was added dropwise over one hour and the reaction mixture was stirred at 50° C. for 24 hours.

The solution was cooled to room temperature, filtered through diatomaceous earth then concentrated. The recovered product was dissolved in 9000 ml of methylene chloride, again filtered through diatomaceous earth, then concentrated and poured into 9000 ml of petroleum ether. The precipitate thus formed was collected by filtration and purified by recrystallization in petroleum ether and dried in vacuum to yield a white solid (1.70 Kg). NMR showed that the product had a structure consistent with 4-((6-((tetrahydro-2H-pyran-2-yl)oxy)hexyl)oxy)benzoic acid.

Step 4

The procedure of Step 2 of Example 1 was followed except the product of step 2 above and the product of step 3 were used in place of 4-((tetrahydro-2H-pyran-2-yl)oxy)phenol and trans,trans-4-pentyl-[1,1'-bi(cyclohexane)]-4-

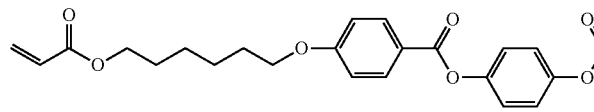

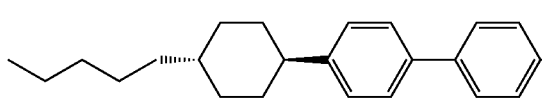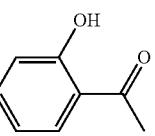

carboxylic acid. The crude product was used directly for the next step without further purification.

Step 5

The procedure of Step 8 of Example 1 was followed except the product of step 4 was used in place of 4-((4-((8-((tetrahydro-2H-pyran-2-yl)oxy)octyl)oxy)benzoyl)oxy)phenyl trans, trans-4'-pentyl-[1,1'-bi(cyclohexane)]-4-carboxylate. Recrystallization from ethyl acetate yielded a white solid. NMR showed that the product had a structure consistent with 4-((4-((6-(acryloyloxy)hexyl)oxy)benzoyl)oxy)-2/3-methylphenyl 4-((6-hydroxyhexyl)oxy)benzoate.

Step 6

The procedure of Step 4 of Example 3 was followed except an equimolar amount of the product of step 5 above was used in place of 4-(6-hydroxyhexyloxy)-4'-(trans-4-pentylcyclohexyl)biphenyl. NMR showed that the product had a structure consistent with 4-((4-((6-(acryloyloxy)hexyl)oxy)benzoyl)oxy)-2/3-methylphenyl 4-((6-(tosyloxy)hexyl)oxy)benzoate.

Step 7

The procedure of Step 10 of Example 1 was followed except an equimolar amount of the product of step 6 above was used in place of 4-((4-((8-(tosyloxy)octyl)oxy)benzoyl)oxy)phenyl trans, trans-4'-pentyl-[1,1'-bi(cyclohexane)]-4-carboxylate. Recrystallization from ethyl acetate yielded a light yellow solid. NMR showed that the produce had a structure consistent with 4-((4-((6-(acryloyloxy)hexyl)oxy)benzoyl)oxy)-2/3-methylphenyl 4-((6-(4-benzoyl-3-hydroxyphenoxy)hexyl)oxy)benzoate, as represented by the following formula.

structure consistent with 2-(2,4-dimethoxyphenyl)benzoxazole.

Step 2

To a suspension of the product of step 1 above (25 g, 97.93 mmol) in 100 mL of dichloromethane, was added BBr$_3$ (73.6 g, 293.8 mmol, 1 M in dichloromethane) dropwise over a period of 30 min at −78° C. The resultant solution was warmed to room temperature over a period of 2 hours and stirred overnight. Saturated aqueous NaCl solution (100 mL) was carefully added to the reaction mixture. The resultant mixture was extracted with dichloromethane (2×200 mL). The combined organic extract was washed with brine (200 mL×2) and dried over anhydrous magnesium sulfate. After filtration, the removal of the solvent of the filtrate gave a crude product which was passed through a short pad of silica gel using dichloromethane-10% ethyl acetate as eluent to yield a dark brown solid (10 g). NMR showed that the product had a structure consistent with 4-(benzoxazole-2-yl)benzene-1,3-diol.

Step 3

The procedure of example 4 was followed except an equimolar amount of the product of step 3 above was used in place of bis(2,4-dihydroxyphenyl)methanone. The crude product was purified by recrystallization from toluene to give light yellow crystals. NMR showed that the product had

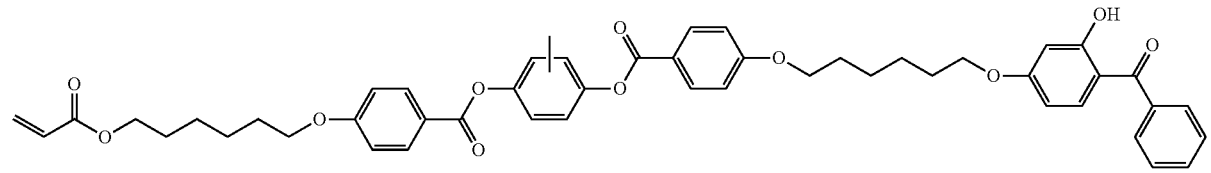

a structure consistent with 2-(benzoxazole-2-yl)-5-((6-((4'-(4-pentylcyclohexyl)-[1,1'-biphenyl]-4-yl)oxy)hexyl)oxy)phenol, as represented by the following formula.

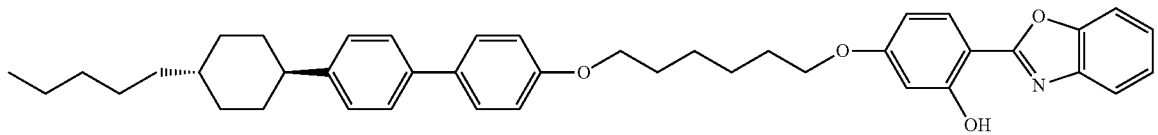 [SMILES: CCCCC[C@H]1CC[C@H](c2ccc(-c3ccc(OCCCCCCOc4ccc(-c5nc6ccccc6o5)c(O)c4)cc3)cc2)CC1]

Example 11

Step 1

In a reaction flask, a suspension of benzoxazole (10 g, 83.94 mmol), 1-bromo-2,4-dimethoxybenzene (22 g, 100.73 mmol), Cs$_2$CO$_3$ (27.3 g, 83.94 mmol), CuBr 2.4 g, 16.78 mmol), Pd(OAc)$_2$ (1 g, 4.2 mmol) and P(t-Bu)$_3$ (1.7 g, 8.39 mmol) in 100 mL of DMF was heated under nitrogen with stirring at 120° C. for three hours. After cooling to room temperature, the reaction mixture was diluted with EtOAc, washed with water (100 mL×3), and dried over MgSO$_4$, then filtered. Evaporation of the solvent from the filtrate gave a crude product which was purified by passing through a short pad of silica gel using dichloromethane/EtOAc (9/1, v/v) as eluent. Yield: 20 g. NMR showed that the product had a Example 12

Step 1

To a reaction flask containing a mixture of 6-chlorohexan-1-ol (25 g, 182.6 mmol), 4-(trans, trans-4'-pentyl-[1,1'-bi(cyclohexane)]-4-yl)phenol (50 g, 152.2 mmol), and a catalytic amount of tetrabutylammonium iodide (0.5 g) in DMF (200 mL) was added potassium carbonate (42 g, 304.4 mmol). The reaction was stirred at 80° C. overnight under nitrogen. Additional 6-chlorohexan-1-ol (10 g) and THF (100 ml) were added and the mixture was stirred an additional two days at 90° C. The suspension was poured into water (2 L) and the precipitated product was filtered and washed with water, re-dissolved in dichloromethane (500 mL) and washed with brine (200 ml×2) before drying over anhydrous magnesium sulfate. After filtration, the filtrate was passed through a short pad of silicagel. The removal of the solvent and recrystallization from ethyl acetate yielded a white crystalline solid (45 g). NMR showed that the product had a structure consistent with 6-(4-(trans, trans-4'-pentyl-[1,1'-bi(cyclohexane)]-4-yl)phenoxy)hexan-1-ol.

Step 2

In a reaction flask, pyridine (15 g, 186.6 mmol) was added to a solution of 6-(4-(trans, trans-4'-pentyl-[1,1'-bi(cyclohexane)]-4-yl)phenoxy)hexan-1-ol (20 g, 46.65 mmol) and 4-toluenesulfonyl chloride (17.8 g, 93.3 mmol) in 200 mL of dichloromethane at room temperature. After stirring overnight, the reaction mixture was added to saturated ammonium chloride (~200 mL). The organic phase was retained. The aqueous phase was extracted by dichloromethane (100 mL×2). The combined organic phase was washed with brine (200 ml×2) and dried over anhydrous magnesium sulfate. After filtration, the filtrate was passed through a short pad of silica gel using 10% EtOAc in dichloromethane (v/v) as eluent. The removal of the solvent offered a product which was purified by recrystallization from EtOAc. Yield: 25 g. NMR showed that the product had a structure consistent with 6-(4-(trans, trans-4'-pentyl-[1,1'-bi(cyclohexane)]-4-yl)phenoxy)hexyl 4-methylbenzenesulfonate.

Step 3

To a mixture of 6-(4-(trans, trans-4'-pentyl-[1,1'-bi(cyclohexane)]-4-yl)phenoxy)hexyl 4-methylbenzenesulfonate (10 g, 17.15 mmol), 2,4-dihydroxybenzophenone (4.4 g, 20.58 mmol) and a catalytic amount of tetrabutylammonium iodide (0.25 g) in THF (100 mL) was added potassium carbonate (4.74 g, 34.3 mmol) followed by stirring for 48 h at 70° C. The removal of THF offered a sticky residue to which 200 ml of water was added. The mixture was extracted with dichloromethane (100 mL×3). The combined organic extracts were washed with brine (100 mL×2) and dried over anhydrous magnesium sulfate. After filtration, evaporation of solvent offered a product which was purified by using a short pad of silica gel using dichloromethane as eluent followed by recrystallization from EtOAc. Yield: 6.6 g. NMR showed that the product had a structure consistent with (2-hydroxy-4-((6-(4-(4'-pentyl-[1,1'-bi(cyclohexan)]-4-yl)phenoxy)hexyl)oxyphenyl)methanone, as represented by the following formula.

Example 13

Step 1

The procedure of Step 1 of Example 12 was followed except 2,6-difluoro-4-(trans, trans-4'-pentyl-[1,1'-bi(cyclohexan)]-4-yl)phenol was used in place of 4-(trans, trans-4'-pentyl-[1,1'-bi(cyclohexane)]-4-yl)phenol yielding white crystals. NMR showed that the product had a structure consistent with 6-(2,6-difluoro-4-(4'-pentyl-[1,1'-bi(cyclohexane)]-4-yl)phenoxy)hexan-1-ol.

Step 2

The procedure of Step 2 of Example 12 was followed except the product of step 1 above was used in place of 6-(4-(trans, trans-4-pentyl-[1,1'-bi(cyclohexane)]-4-yl)phenoxy)hexan-1-ol to yield white crystals. NMR showed that the product had a structure consistent with trans, trans-6-(2,6-difluoro-(4-(4'-pentyl-[1,1'-bi(cyclohaxane)]-4-yl)phenoxy)hexyl 4-methylbenzenesulfonate.

Step 3

The procedure Step 3 of Example 12 was followed except the product of step 2 above, 2,4-dihydroxybenzophenone and THF were used in place of 6-(4-(trans, trans-4'-pentyl-[1,1'-bi(cyclohexane)]-4-yl)phenoxy)hexyl 4-methylbenzenesulfonate and bis(2,4-dihydroxyphenyl)methanone and 2-Butanone, respectively. The crude product was purified by recrystallization from hexane to yield light yellow crystals. NMR showed that the product had a structure consistent with 4-((6-(2,6-difluoro-4-(trans, trans-4'-pentyl-[1,1'-bi(cyclohexan)]-4-yl)phenoxy)hexyl)oxy)-2-hydroxyphenyl)(phenyl)methanone, as represented by the following formula.

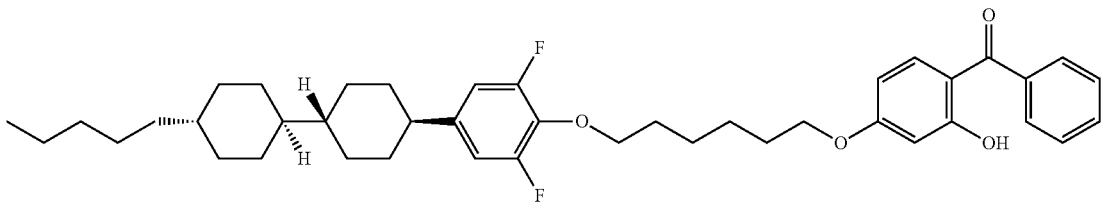

Example 14

A mixture of 4-((4-((8-hydroxyoctyl)oxy)benzoyl)oxy)phenyl 4-methylbenzoate (10 g, 20.98 mmol) (custom synthesized by CIAC, China), alpha-cyanocinnamic acid (4.0 g, 23.08 mmol), dicyclohexylcarbodiimide (5.18 g, 25.17 mmol), and 4-dimethylaminopyridine (0.385 g, 3.15 mmol) in dichloromethane (100 mL) was stirred at room temperature under nitrogen overnight. The white precipitate that formed was discarded. The resulting solution was partially concentrated, purified using a short pad of silicagel eluting with dichloromethane then crystallized from a mixture of THF and ethyl acetate to yield a white solid (10 g). NMR

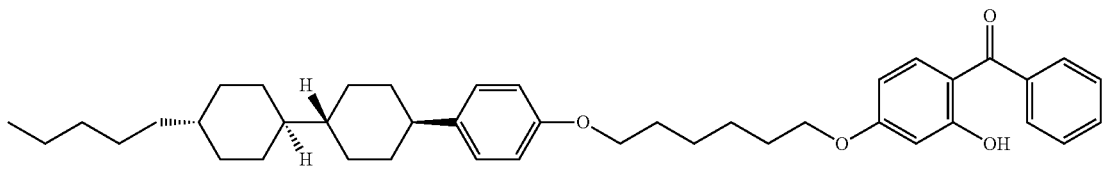 [SMILES: CCCCC[C@H]1CC[C@H]([C@H]2CC[C@H](c3ccc(OCCCCCCOc4ccc(C(=O)c5ccccc5)c(O)c4)cc3)CC2)CC1]

showed that the product had a structure consistent with (E)-4-((4-((8-((2-cyano-3-phenylacryloyl)oxy)octyl)oxy)benzoyl)oxy)phenyl 4-methylbenzoate, as represented by the following formula.

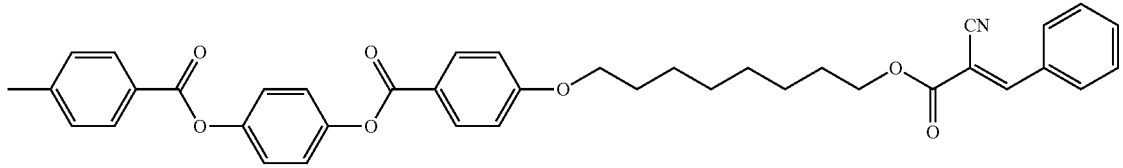 [SMILES: Cc1ccc(C(=O)Oc2ccc(OC(=O)c3ccc(OCCCCCCCCOC(=O)/C(C#N)=C/c4ccccc4)cc3)cc2)cc1]

Example 15

Step 1

A suspension of methyl-2-cyano-3,3-diphenylacrylate (20.5 g, 73.9 mmol) in ethanol (100 mL), water (100 mL) and NaOH (7.12 g, 184.75 mmol) was stirred overnight at room temperature and then acidified with 10.2 g of 36% HCl. The precipitate was filtered off, washed with water and dried to yield 17 g of yellowish powder. NMR showed that the product had a structure consistent with 2-cyano-3,3-diphenylacrylic acid.

Step 2

The procedure of Example 14 was followed except the product of step 1 above was used in place of alpha-cyanocinnamic acid to yield a white solid. NMR showed that the product had a structure consistent with 4-((4-((8-((2-cyano-3,3-diphenylacryloyl)oxy)octyl)oxy)benzoyl)oxy)phenyl 4-methylbenzoate, as represented by the following formula.

Step 2

To the product of step 2 of example 7 (20 g, 41.97 mmol), and succinic anhydride (5.04 g, 50.4 mmol, 1.2 equiv) was added 400 mL of toluene and a catalytic amount of 4-dimethylaminopyridine. The reaction was heated at reflux overnight then cooled to room temperature. The formed precipitate was collected by filtration and dried in air to yield a quantitative amount of white powder.

Step 3

A solution of the product of Step 2 above (4 g, 1.73 mmol), the product of Step 1 above (1.76 g, 1.73 mmol), N,N'-dicyclohexylcarbodiimide (1.6 g, 1.9 mmol) and 4-N,N-dimethylaminopyridine (0.1 g, 0.17 mmol) and 200 mL of dichloromethane in a 500 mL single-necked, round-bottomed flask was stirred at room temperature under nitrogen atmosphere overnight. The white precipitate that formed during the reaction was discarded by filtration through a Buchner funnel. The resulting solution was passed through a short pad of silica gel eluted using dichloromethane. The removal of the solvent offered a product which was purified

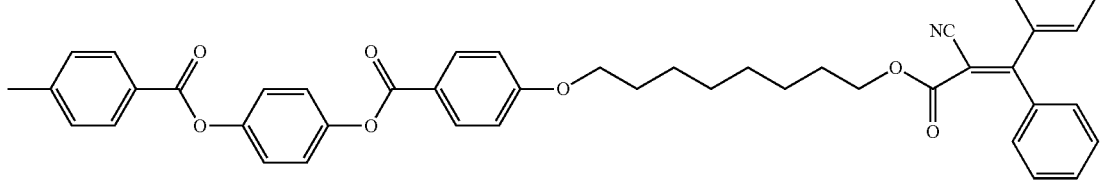

Example 16

Step 1

A suspension of ethyloxanilate (10 g, 51.76 mmol) and 4-aminophenol (5.65 g, 51.76 mmol) in 50 mL of ethylene glycol was heated to 90° C. for 5 hours. The resulting suspension was added to water (200 mL) to yield a precipitate which was collected and dried at 60° C. The crude product was precipitated from dichloromethane and methanol at −10° C. to yield of off-white crystals (7 g). NMR showed that the product had a structure consistent with $N^1$-(4-hydroxyphenyl)-$N^2$-phenyloxalamide.

by recrystallization from a mixture of THF and EtOAc (1/2, v/v) to give the final product as a white solid. Yield: 5.5 g. NMR showed that the product had a structure consistent with 8-(4-((4-((4-methylbenzoyl)oxy)phenoxy)carbonyl)phenoxy)octyl (4-(2-oxo-2-(phenylamino)acetamido)phenyl)succinate, as represented by the following formula, as represented by the following formula.

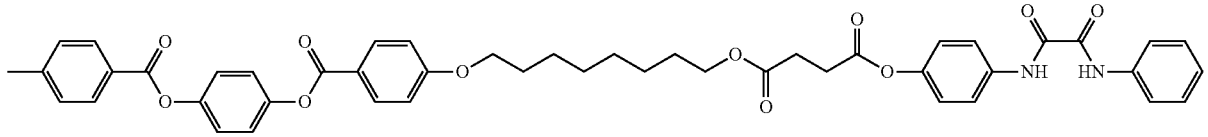 [SMILES: Cc1ccc(C(=O)Oc2ccc(OC(=O)c3ccc(OCCCCCCCCOC(=O)CCC(=O)Oc4ccc(NC(=O)C(=O)Nc5ccccc5)cc4)cc3)cc2)cc1]

Example 17

To a solution of 2,4-dihydroxybenzophenone (4.60 g, 21.5 mmol), 4-(4-pentylcyclohexyl)benzoic acid (5.89 g, 24.5 mmol), and 4-dimethylaminopyridine (0.2600 g, 2.130 mmol) in dichloromethane (150 mL) was added N,N'- dicyclohexylcarbodiimide (4.95 g, 24.0 mmol). After stirring for 4 hours at room temperature, additional 4-(4-pentylcyclohexyl)benzoic acid (0.24 g, 0.87 mmol), N,N'-dicyclohexylcarbodiimide (0.26 g, 1.3 mmol), and 4-dimethylaminopyridine (0.0124 g, 0.101 mmol) was added and the solution stirred overnight. The N,N'-dicyclohexylurea byproduct was removed and the filtrate was concentrated onto silica gel before being chromatographed (120 g column, eluent was 2.5% vol/vol EtOAc in hexanes). The resulting off-white material was recrystallized from a mixture of EtOH/acetonitrile/EtOAc (60/20/20, v/v/v) to give light yellow crystals (8.36 g). NMR analysis showed that the product had a structure consistent with 4-benzoyl-3-hydroxyphenyl 4-(4-pentylcyclohexyl)benzoate, as represented by the following formula.

end, another addition of the 4-(4-pentylcyclohexyl)benzoic acid (0.42 g, 1.8 mmol), N,N'-dicyclohexylcarbodiimide (0.38 g, 1.8 mmol), and 4-dimethylaminopyridine (0.0179 g, 0.147 mmol) was made. After stirring overnight, the N,N'-dicyclohexylurea byproduct was removed and the filtrate was partially concentrated under reduced pressure before being filtered through a silica plug (eluent was 80% v/v dichloromethane in hexanes) to give a light yellow solid which was recrystallized from EtOAc to afford a light yellow material (8.51 g). NMR showed that the product had a structure consistent with 4-(2-hydroxy-4-((4-(4-pentylcyclohexyl)benzoyl)oxy)benzoyl)phenyl 4-(4-pentylcyclohexyl)benzoate, as represented by the following formula.

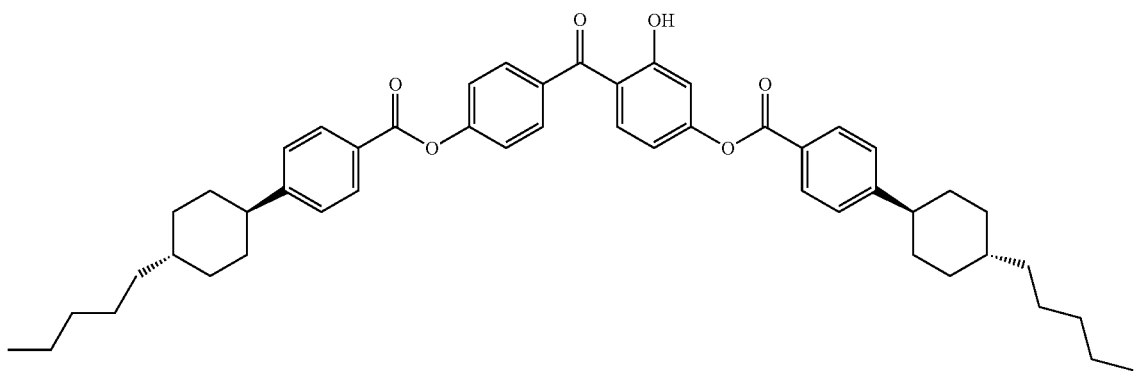

Example 19

Step 1

To a solution of 2,2',4,4'-tetrahydroxybenzophenone (3.10 g, 12.6 mmol), 4-(4-pentylcyclohexyl)benzoic acid (3.46 g, 12.60 mmol) and 4-dimethylaminopyridine (0.1540 g, 1.260 mmol) in dichloromethane/EtOAc (100 mL, 95/5 vol %) was added N,N'-dicyclohexylcarbodiimide (2.84 g, 13.76 mmol). After stirring at room temperature under nitrogen for 30 minutes, a second addition of 4-(4-pentylcyclohexyl)benzoic acid (3.46 g, 12.60 mmol), 4-dimethylaminopyridine (0.1540 g, 1.260 mmol), and N,N'-dicyclohexylcarbodiimide (2.84 g, 13.76 mmol) was made. After stirring for 5 hours, another addition of 4-(4-pentylcyclohexyl)benzoic acid (1.05 g, 4.26 mmol), 4-dimethylaminopyridine (0.0941 g, 0.770 mmol), and N,N'-dicyclohexylcarbodiimide (0.90 g, 4.36 mmol) was made and the mixture stirred overnight. The N,N'-dicyclohexylurea byproduct was removed and the filtrate was concentrated to yield an off white solid, which was recrystallized from EtOAc to give the desired product (1.94 g). NMR showed that the product had a structure consistent with carbonylbis(3-hydroxy-4,1-phenylene) bis(4-(4-pentylcyclohexyl)benzoate), as represented by the following formula.

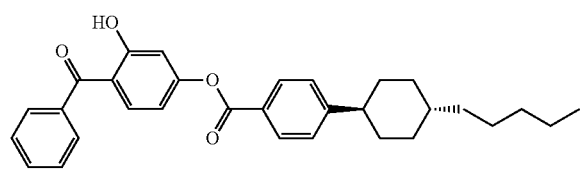 [SMILES: CCCCC[C@H]1CC[C@H](c2ccc(C(=O)Oc3ccc(C(=O)c4ccccc4)c(O)c3)cc2)CC1]

Example 18

To a solution of 2,4,4'-trihydroxybenzophenone (3.10 g, 13.47 mmol), 4-(4-pentylcyclohexyl)benzoic acid (3.71 g, 13.5 mmol), and 4-dimethylaminopyridine (0.1650 g, 1.350 mmol) in dichloromethane (100 mL) and EtOAc (5 mL) was added N,N'-dicyclohexylcarbodiimide (3.25 g, 15.7 mmol). After stirring for 30 minutes at room temperature, another addition of 4-(4-pentylcyclohexyl)benzoic acid (3.71 g, 13.5 mmol), 4-dimethylaminopyridine (0.1650 g, 1.350 mmol), and N,N'-dicyclohexylcarbodiimide (3.25 g, 15.7 mmol) was made. After stirring at room temperature over a week-

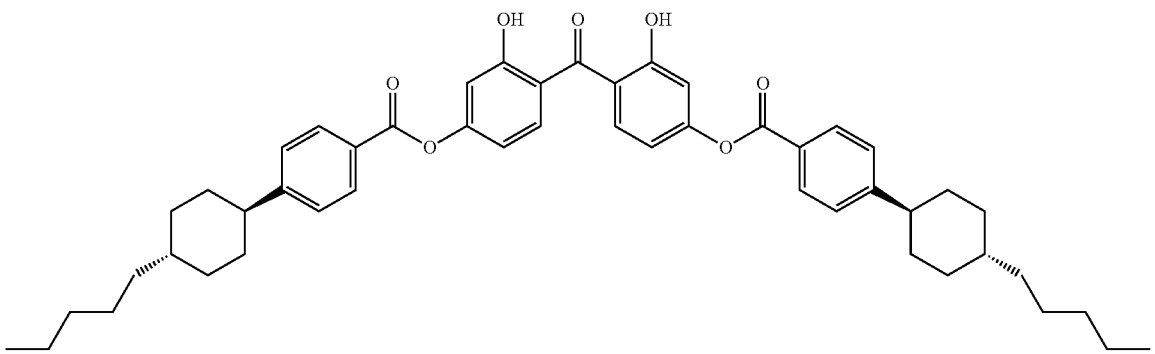 [SMILES: CCCCC[C@H]1CC[C@H](c2ccc(C(=O)Oc3ccc(C(=O)c4ccc(OC(=O)c5ccc([C@H]6CC[C@H](CCCCC)CC6)cc5)cc4O)c(O)c3)cc2)CC1]

Example 20

To a solution of 2,4-dihydroxybenzophenone (4.00 g, 18.7 mmol), 4'-(4-pentylcyclohexyl)-[1,1'-biphenyl]-4-carboxylic acid (6.54 g, 18.7 mmol), and 4-dimethylaminopyridine (0.23 g, 1.9 mmol) in dichloromethane/EtOAc (95/5 vol %) was added N,N'-dicyclohexylcarbodiimide (4.36 g, 21.1 mmol). After stirring under nitrogen at room temperature for 6 hours, additional 4'-(4-pentylcyclohexyl)-[1,1'-biphenyl]-4-carboxylic acid (0.39 g, 1.1 mmol), N,N'-dicyclohexylcarbodiimide (0.36 g, 1.7 mmol), and 4-dimethylaminopyridine (0.0131 g, 0.107 mmol) were added an the solution stirred over a weekend. The N,N'-dicyclohexylurea byproduct was removed and the filtrate partially concentrated before being run through a silica plug (eluent was 100% dichloromethane). The resulting material was recrystallized from EtOAc to give the desired product (8.32 g). NMR showed that the product had a structure consistent with 4-benzoyl-3-hydroxyphenyl 4'-(4-pentylcyclohexyl)-[1,1'-biphenyl]-4-carboxylate, as represented by the following formula.

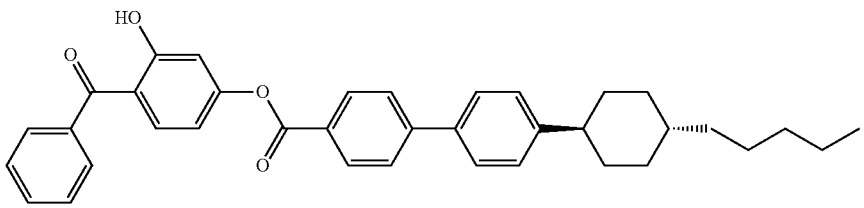 [SMILES: CCCCC[C@H]1CC[C@H](c2ccc(-c3ccc(C(=O)Oc4ccc(C(=O)c5ccccc5)c(O)c4)cc3)cc2)CC1]

Example 21

To a solution of 2,2',4,4'-tetrahydroxybenzophenone (5.00 g, 20.3 mmol), 4-(4-pentylcyclohexyl)benzoic acid (5.30 g, 19.3 mmol) and 4-dimethylaminopyridine (0.25 g, 2.1 mmol) in dichloromethane/EtOAc (95/5 vol %) was added N,N'-dicyclohexylcarbodiimide (4.75 g, 23.0 mmol). After stirring over a weekend at room temperature, the N,N'-dicyclohexylurea byproduct was removed and the filtrate was partially concentrated before being run through a silica plug (eluent was 100% dichloromethane then switched to 10% EtOAc in dichloromethane, v/v)) which gave two fractions. The less pure fraction was recrystallized from EtOAc which caused the "dimesogen" to crystallize out while the desired product remained in the mother liquor. The mother liquor and remaining fraction were combined (5.92 g) and concentrated onto silica before being purified via CombiFlash (eluent was 5% dichloromethane in hexanes) to give a material which was then recrystallized from EtOH to give the desired product (1.74 g). NMR showed that the product had a structure consistent with 4-(2,4-dihydroxybenzoyl)-3-hydroxyphenyl 4-(4-pentylcyclohexyl)benzoate, as represented by the following formula.

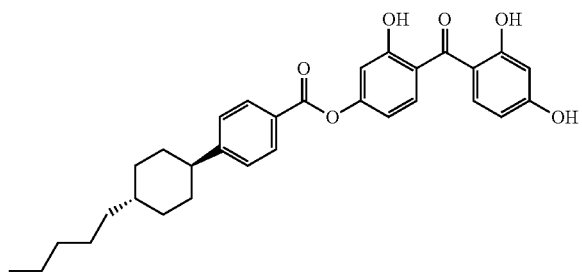 [SMILES: CCCCC[C@H]1CC[C@H](c2ccc(C(=O)Oc3ccc(C(=O)c4ccc(O)cc4O)c(O)c3)cc2)CC1]

Example 22

Step 1

In a one-neck, round bottom flask under a nitrogen blanket, 1H-benzo[d][1,2,3]triazole (2.60 g, 21.8 mmol) was dissolved in a solution of dichloromethane/THF (40 mL anhydrous, 50/50, v/v), followed by dropwise addition of $SOCl_2$ (0.55 mL, d=1.64 g/mL, 7.6 mmol). After stirring at room temperature for 1 hour, a solution of salicylic acid (1.00 g, 7.25 mmol) in THF (15 mL anhydrous), was added dropwise and allowed to stir for about 2 hours.

Step 2

A separate solution of 4'-pentyl-[1,1'-bi(cyclohexan)]-4-ol (2.76 g, 10.9 mmol) was dissolved in THF (10 mL, anhydrous) followed by addition of sodium hydride (0.47 g, 60% dispersion in mineral oil, 12 mmol). The reaction was stirred at room temperature under nitrogen for 10 minutes after which time the liquid was decanted off and added to the solution of step 1 above. After stirring overnight at room temperature under nitrogen, the material was passed through a silica plug (eluent was 5% EtOAc in hexane) to give a white solid which was recrystallized twice from EtOH/EtOAc (80/20, v/v) to yield a white solid. NMR showed that the product had a structure consistent with 4'-pentyl-[trans-trans-1,1'-bi(cyclohexan)]-4-yl 2-hydroxybenzoate, as represented by the following formula.

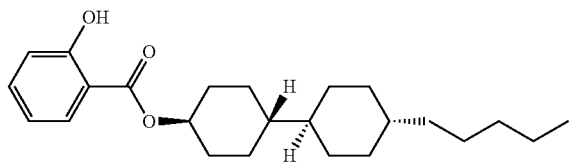 [SMILES: CCCCC[C@H]1CC[C@H]([C@H]2CC[C@H](OC(=O)c3ccccc3O)CC2)CC1]

mmol), and BHT (0.0328 g, 0.148 mmol) in dichloromethane (100 mL) was added N,N'-dicyclohexylcarbodiimide (3.52 g, 17.1 mmol). After stirring under nitrogen at room temperature for 5 hours under Nitrogen the N,N'-dicyclohexylurea byproduct was removed and the filtrate partially concentrated before being filtered through a silica plug (eluent was 10% EtOAc in a 50:50 solution of dichloromethane/hexanes, vol/vol %) to give a yellow, impure oil (8.9 g). The material was concentrated onto silica, then purified via CombiFlash (eluent was 20% EtOAc in hexanes, vol/vol %) to give an off-white solid (3.73 g) which was recrystallized from EtOH/EtOAc (75/25 vol/vol %). Yield: 3.17 g. NMR showed that the product had a structure consistent with 4-((4-benzoyl-3-hydroxyphenoxy)carbonyl)phenyl 4-((6-(acryloyloxy)hexyl)oxy)benzoate, as represented by the following formula.

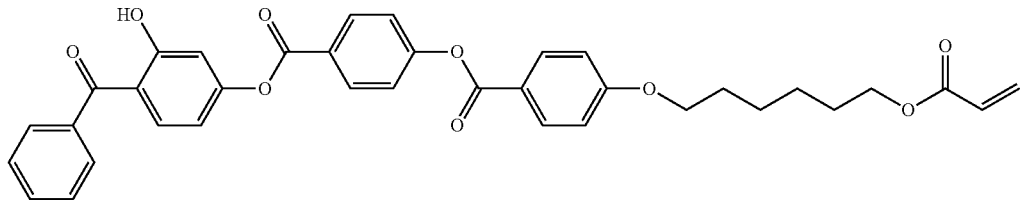 [SMILES: C=CC(=O)OCCCCCCOc1ccc(C(=O)Oc2ccc(C(=O)Oc3ccc(C(=O)c4ccccc4)c(O)c3)cc2)cc1]

Example 23

Example 24

Step 1

To a solution of 2,4-dihydroxybenzophenone (6.00 g, 28.0 mmol), 4-((tetrahydro-2H-pyran-2-yl)oxy)benzoic acid (6.22 g, 28.0 mmol) (made in accordance with the published procedure in Macromolecules 1995, 28, 3313-332), and 4-dimethylaminopyridine (0.3422 g, 2.801 mmol) in dichloromethane (100 mL) was added N,N'-dicyclohexylcarbodiimide (6.36 g, 30.8 mmol). After stirring under nitrogen at room temperature overnight, additional 4-((tetrahydro-2H-pyran-2-yl)oxy)benzoic acid (0.75 g, 3.4 mmol), 4-dimethylaminopyridine (0.0409 g, 0.33 mmol), and N,N'-dicyclohexylcarbodiimide (0.90 g, 4.4 mmol) were added. After stirring for 4 hours, N,N'-dicyclohexylurea byproduct was removed and the filtrate was partially concentrated before being filtered through a silica plug (eluent was 2.5% EtOAc in dichloromethane, v/v) to give and off-white solid (11.87 g) which was used directly for the next step without further purification.

Step 2

The product from Step 1 above was dissolved in a mixture of MeOH/THF (1/1 vol/vol %) (200 mL) before TsOH (1.07 g, 5.60 mmol) was added. After stirring at room temperature for 30 minutes, the solution was concentrated to about 100 mL total volume, and the product was precipitated by addition of ice-cold methanol (20 mL). The resulting solids were collected and dried under vacuum. NMR showed that the product had a structure consistent with 4-benzoyl-3-hydroxyphenyl 4-hydroxybenzoate (8.67 g), which was used for the next step without further purification.

Step 3

To a solution of 4 the product of step 2 above (5.00 g, 15.0 mmol), 4-((6-(acryloyloxy)hexyl)oxy)benzoic acid (4.38 g, 15.0 mmol), 4-dimethylaminopyridine (0.1825 g, 1.49

Step 1

The procedure of Step 4 of Example 3 was followed except 1-(6-(6-(6-(6-(6-(6-(6-(6-(4-(4-(4-(6-acrylyloxyhexyloxy)benzoyloxy)phenyloxycarbonyl) phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexyloxy)-6-oxohexanol was used in place of 6-((4'-(trans-4-pentylcycohexyl)-[1,1'-biphenyl]-4-yl)oxy)hexane-1-ol using trimethylamine as base. The crude product was purified by precipitation from dichloromethane/MeOH (1/10, v/v) at −20° C. to give an off-white solid, which was used directly for the next step without further purification.

Step 2

The procedure of Step 10 of Example 1 was followed except that the product of step 1 above (5.30 g) was used in place of trans, trans-4-((4-((8-(tosyloxy)octyl)oxy)benzoyl)oxy)phenyl 4'-pentyl-[1,1'-bi(cyclohexane)]-4-carboxylate. The crude product was purified through a silica plug eluting with 10% EtOAc in dichloromethane (v/v) with subsequent precipitation from dichloromethane/methanol (1/10, v/v) at 0° C. to yield an off-white solid. NMR showed the product had a structure consistent with (4-(1-(6-(6-(6-(6-(6-(6-(6-(6-(4-(4-(4-(6-acrylyloxyhexyloxy)benzoyloxy)phenyloxycarbonyl) phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexylxy)-2-hydroxyphenyl)(phenyl)methanone, as represented by the following formula.

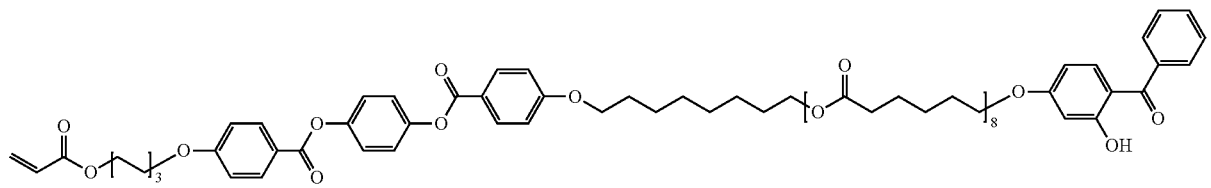

Example 25

To a solution of 4-(1H-benzo[d]imidazol-2-yl)benzene-1,3-diol (3.00 g, 13.3 mmol), 4-pentylcyclohexanecarboxylic acid (2.65 g, 13.4 mmol), and 4-dimethylaminopyridine (0.1607 g, 1.32 mmol) in dichloromethane (75 mL) was added N,N'-dicyclohexylcarbodiimide (3.24 g, 15.7 mmol). After stirring under nitrogen overnight, the N,N'-dicyclohexylurea byproduct was removed and the filtrate was concentrated onto silica before being chromatographed (eluent was 25% EtOAc in hexanes, vol/vol %). then recrystallized from ethyl acetate. Yield: 1.69 g. NMR showed that the product had a structure consistent with 4-(1H-benzo[d]imidazol-2-yl)-3-hydroxyphenyl 4-pentylcyclohexane-1-carboxylate, as represented by the following formula.

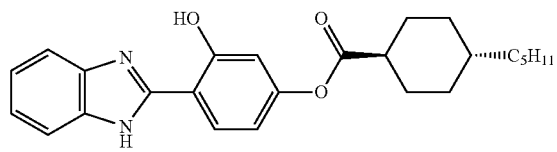

Example 26

Step 1

To a solution of 6-((4'-(4-pentylcyclohexyl)-[1,1'-biphenyl]-4-yl)oxy)hexyl 4-methylbenzenesulfonate (3.97 g, 6.88 mmol) and 2,4-dihydroxybenzaldehyde (0.95 g, 6.9 mmol) in THF (50 mL; anhydrous) was added potassium carbonate (1.89 g, 13.7 mmol). The reaction was heated at reflux overnight but significant starting material was still present. The reaction was heated under reflux, under nitrogen for another 4 days, with daily additions of 2,4-dihydroxybenzaldehyde (0.38 g, 0.46 g, 0.25 g, 0.11 g). The reaction was refluxed an additional two days with additions of $CsCO_3$ (0.42 g, 0.42 g) before the reaction reached completion. Once at room temperature, water was added causing the product to precipitate out of solution. The formed precipitate was collected via filtration and recrystallized from hot THF with ethanol added drop-wise until the solution remained slightly cloudy, yielding an off-white solid ((2.46 g).

Step 2

A solution of the product of step 1 above (2.46 g, 4.53 mmol), $Na_2S_2O_5$ (0.87 g, 4.6 mmol), and benzene-1,2-diamine (0.50 g, 4.6 mmol) in DMF (40 mL, anhydrous) and heated at 130° C. under nitrogen for about 8 hours. Water was added (~200 mL) to the cooled solution and after stirring in an ice bath the resulting dark brown solid was isolated via filtration. The material was concentrated onto silica and chromatographed (eluent was 10% EtOAc with 1% acetic acid in dichloromethane, v/v) to give a tan solid. NMR showed that the product had a structure consistent with 2-(1H-benzo[d]imidazol-2-yl)-5-((6-((4'-(trans-4-pentylcyclohexyl)-[1,1'-biphenyl]-4-yl)oxy)hexyl)oxy)phenol, as represented by the following formula.

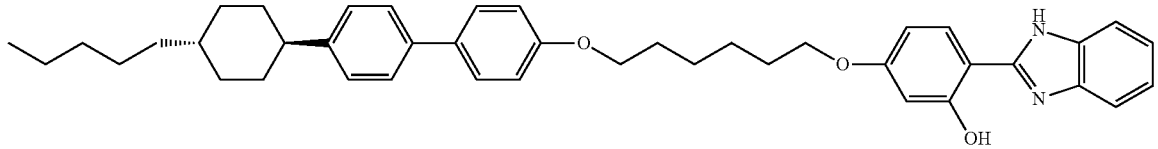 [SMILES: CCCCC[C@H]1CC[C@H](c2ccc(-c3ccc(OCCCCCCOc4ccc(-c5nc6ccccc6[nH]5)c(O)c4)cc3)cc2)CC1]

Example 27

To a reaction flask containing 6-((4'-(4-pentylcyclohexyl)-[1,1'-biphenyl]-4-yl)oxy)hexyl 4-methylbenzenesulfonate (8.00, 13.87 mmol), 4-(2H-benzo[d][1,2,3]triazol-2-yl)benzene-1,3-diol (3.15 g, 13.87 mmol) and potassium carbonate (3.75 g, 41.61 mmol) was added dry THF (200 mL). The mixture was heated to reflux for 24 hours under nitrogen, then poured into 500 mL of icy water. The formed precipitate was collected by filtration and recrystallized from THF/ethyl acetate (1/1, v/v) three times to yield a pale solid (2 g). NMR showed that the product had a structure consistent with 2-(1H-benzo[d]imidazol-2-yl)-5-((6-((4'-(trans-4-pentylcyclohexyl)-[1,1'-biphenyl]-4-yl)oxy)hexyl)oxy)phenol, as represented by the following formula.

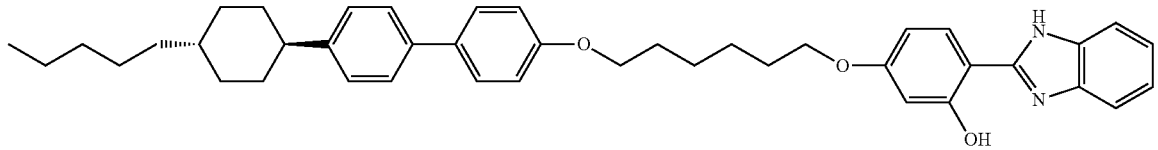 [SMILES: CCCCC[C@H]1CC[C@H](c2ccc(-c3ccc(OCCCCCCOc4ccc(-c5nc6ccccc6[nH]5)c(O)c4)cc3)cc2)CC1]

Example 28

Step 1

To a solution of 2-chloro-4,6-diphenyl-1,3,5-triazine (4.68 g, 17.5 mmol), made by following the published procedure (*Organic Letters*, 2008, vol. 10, #5 p. 709-712), and resorcinol (2.51 g, 22.8 mmol) in 1,2-dichloroethane (100 mL) was added $AlCl_3$ (3.11 g, 23.3 mmol). The resulting solution was heated overnight in a 60° C. oil-bath under nitrogen. The solvent was removed under reduced pressure and the resulting solid was suspended in water (200 mL). The dark yellow solid was recrystallized from ethanol to give 4-(4,6-Diphenyl-1,3,5-triazin-2-yl)benzene-1,3-diol in the form of a brown solid which was used for the next step without further purification.

Step 2

To a solution of the product of Step 1 above (1.85 g, 5.42 mmol), 4-((8-(4-((4-((4-methylbenzoyl)oxy)phenoxy)carbonyl)phenoxy)octyl)oxy)-4-oxobutanoic acid (3.17 g, 5.50 mmol), and 4-dimethylaminopyridine (0.0725 g, 0.593 mmol) in dichloromethane (75 mL) was added N,N'-dicyclohexylcarbodiimide (1.32 g, 6.40 mmol). After stirring under nitrogen at room temperature for 5 hours, the N,N'-dicyclohexylurea byproduct was removed and the filtrate was run through a short plug of silica (dichloromethane eluent) to give an off-white solid (4.98 g) which was then recrystallized from THF to give an off-white solid (3.71 g). NMR showed that the product had a structure consistent with 4-(4,6-diphenyl-1,3,5-triazin-2-yl)-3-hydroxyphenyl (8-(4-((4-((4-methylbenzoyl)oxy)phenoxy)carbonyl)phenoxy)octyl) succinate, as represented by the following formula, as represented by the following formula.

g) which was used without further purification. NMR showed that the major product had a structure consistent with 2-(2,4-dimethoxyphenyl)quinazoline

Step 3

To a solution of the product from Step 2 above (5.40 g) in dichloromethane (100 mL) at −78° C. was added $BBr_3$ (4.60 mL) dropwise over about 1 minute. The solution was stirred under nitrogen at −78° C. for one hour then warmed to room temperature over 3 hours. The solution was neutralized to about pH 8 with aqueous $Na_2CO_3$ followed by extraction with ethyl acetate (3×100 mL). The combined organic extracts were dried over $MgSO_4$, partially concentrated and filtered through a short silica plug to give a dark material (3.63 g). After concentrating onto silica, the material was chromatographed via CombiFlash to give a yellow solid (~1.5 g) which by NMR analysis was found to be the mono-methoxy material which. This was dissolved in dichloromethane (about 75 mL) and cooled to −78° C. followed by dropwise addition of $BBr_3$ (1.10 mL, 11.6 mmol) over about 1 minute. The solution was kept at −78° C. for about 45 minutes before being warmed to room temperature. The solution was heated under reflux for about 7 days. The solution was adjusted to about pH 8 using aqueous $Na_2CO_3$ and extracted with EtOAc (3×50 mL). The combined organic extracts were washed with brine, dried over $MgSO_4$ and concentrated to a dark oil which was then concentrated onto silica. The material was purified via CombiFlash (eluent was 20% EtOAc in hexanes, v/v) to give an orange oil (0.17 g). NMR showed that the product had a structure consistent with 4-(quinazolin-2-yl)benzene-1,3-diol.

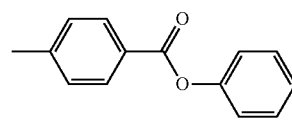
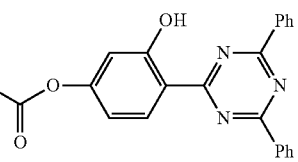

Example 29

Step 1

In a one-neck round bottom flask, 2,4-dimethoxybenzaldehyde (2.49 g) and 2-(aminomethyl)aniline (3.40 g) were dissolved in ethanol (75 mL) and stirred at room temperature overnight. Solvent was removed under reduced pressure, then water was added to yield a biphasic system which was extracted with ethyl acetate (3×50 mL). The combined organic extracts were washed with brine, dried over $MgSO_4$ and concentrated under reduced pressure to give a thick oil which slowly solidified to a white material (5.70 g) which was used without further purification. NMR showed that the product had a structure consistent with 2-(2,4-dimethoxyphenyl)-1,2,3,4-tetrahydroquinazoline.

Step 2

To a solution of the product from Step 1 above (5.60 g) in acetone (100 mL) was added $KMnO_4$ (4.09 g). The mixture was stirred for 6 hours, additional $KMnO_4$ was added (1.01 g) and the reaction stirred overnight followed by another addition of $KMnO_4$ (1.35 g). The mixture was stirred an additional 4 hours, quenched by adding 2-propanol (10 mL), filtered through diatomaceous earth and concentrated. The resulting residue was dissolved in ethyl acetate and filtered through a short silica plug to give an orange semi-solid (5.40

Step 4

To a solution of the product from Step 3 above (0.17 g), 4-((8-(4-((4-((4-methylbenzoyl)oxy)phenoxy)carbonyl)phenoxy)octyl)oxy)-4-oxobutanoic acid (0.42 g) and 4-dimethylaminopyridine (0.0880 g) in dichloromethane (5 mL) was added N,N'-dicyclohexylcarbodiimide (0.18 g). After stirring under nitrogen for 4 hours at room temperature, the solution was passed through a short pad of silica (eluent 5% EtOAc in dichloromethane, v/v) to give a yellow solid (0.44 g) which was then concentrated onto silica and chromatographed (2.5% EtOAc in dichloromethane, v/v) to give light yellow solid (0.2945 g). NMR showed that the product had a structure consistent 3-hydroxy-4-(quinazolin-2-yl)phenyl (8-(4-((4-((4-methylbenzoyl)oxy)phenoxy)carbonyl)phenoxy)octyl) succinate.

Example 30

Step 1

In a one-neck round bottom flask, 2-bromopyridine (1.00 g), (2,4-dimethoxyphenyl)boronic acid (1.15 g), and $Na_2CO_3$ (2.02 g) (made in accordance with the published procedure in *Dalton Trans.* 2014, 43 (15), 5667-5679) were stirred in a solution of THF (22.4 mL) and water (9.4 mL) before being degassed by sonicating under vacuum. $Pd(PPh_3)_4$ (0.34 g) was added and the solution was heated at reflux overnight under nitrogen. The solvent was removed under reduced pressure and the resulting residue was dissolved in ethyl acetate and washed with water. The aqueous layer was then extracted with ethyl acetate (3×50 mL) and the combined organic extracts were washed with brine and dried over MgSO$_4$. The residue was concentrated under reduced pressure, dissolved in dichloromethane and passed through a short plug of silica gel (eluent was dichloromethane). The resulting material was used without further purification.

Step 2

In a one-neck round bottom flask, the product from Step 1 above (2.67 g) and pyridine hydrochloride (21.55 g) (made in accordance with the published procedure in *J. Med. Chem.* 1998, 41 (15), 2732-2744) were heated at 160° C. under nitrogen for about 40 hours. Once at room temperature, the solution was diluted with water and ethyl acetate before being adjusted to about pH 8 using aqueous Na$_2$CO$_3$. The organic layer was reserved and the aqueous layer was extracted with ethyl acetate (3×75 mL). The combined organic extracts were washed with brine (50 mL), dried over MgSO$_4$ and concentrated to a dark oil. The material was then chromatographed via CombiFlash (eluent was 30% ethyl acetate in hexanes, v/v) to give a yellow solid (1.79 g). NMR showed that the product had a structure consistent with 4-(pyridin-2-yl)benzene-1,3-diol.

Step 3

To a solution of the product from Step 2 above (1.30 g), 4-((8-(4-((4-((4-methylbenzoyl)oxy)phenoxy)carbonyl)phenoxy)octyl)oxy)-4-oxobutanoic acid (4.01 g), and 4-dimethylaminopyridine (0.0889 g) in dichloromethane was added N,N'-dicyclohexylcarbodiimide (1.82 g). After stirring overnight at room temperature under nitrogen, the N,N'-dicyclohexylurea byproduct was removed and the filtrate was passed through a short plug of silica (eluent was dichloromethane then switched to 10% EtOAc in dichloromethane, v/v). The resulting material was then concentrated onto silica and chromatographed (eluent was 7% EtOAc in a 50/50 solution of dichloromethane/hexanes, v/v) to give an off-white solid (3.39 g). NMR analysis was consistent with 3-hydroxy-4-(pyridin-2-yl)phenyl (8-(4-((4-((4-methylbenzoyl)oxy)phenoxy)carbonyl)phenoxy)octyl) succinate, as represented by the following formula.

TABLE 1-continued

| Primer Layer Formulation | |
|---|---|
| Component | Amount |
| TRIXENE ® BI 7960[4] | 15.62 g |
| BYK ®-333[5] | 0.034 g |
| K-KAT ® 348[6] | 0.454 g |
| Gamma-Glycidoxypropyltrimethoxysilane | 1.79 g |
| TINUVIN ® 144[7] | 0.757 g |
| IRGANOX ® 245[8] | 0.757 g |
| Dipropylene Glycol Methyl Ether Acetate | 32.77 g |

[1]According to composition D of Example 1 in U.S. Pat. No. 6,187,444 replacing styrene with methyl methacrylate and 0.5% by weight of triphenyl phosphite was added.
[2]A polyalkylenecarbonate diol available from Great Lakes Chemical Corp.
[3]A blocked aliphatic polyisocyanate available from Covestro AG.
[4]A blocked trifunctional urethane crosslinker available from Baxenden Chemicals, Ltd
[5]A polyether modified polydimethylsiloxane available from BYK Chemie, USA
[6]A bismuth carboxylate catalyst available from King Industries.
[7]A hindered amine light stabilizer available from BASF Corporation.
[8]An antioxidant available from BASF Corporation.
The mixture was stirred at room temperature for 2 hours to yield a solution having 51.47 weight % final solids based on the total weight of the solution.

Part 2—Preparation of Liquid Crystal Alignment Formulation (LCAF).

A photoalignment material described in US Patent Application Publication No. US 2011/0135850 A1 as a Comparative Example was prepared by adding 6 weight percent of the photoalignment material to cyclopentanone, based on the total weight of the solution. This mixture was allowed to stir until the photoalignment material was completely dissolved.

Part 3—Preparation of the Coating Layer Formulation (CLF).

A coating layer formulation was prepared by combining the materials indicated in the following Table 2 and stirring for two hours at 80° C. to yield a homogeneous solution, then cooled to room temperature. All quantities are reported as parts by weight.

TABLE 2

| Coating Layer Formulation CLF-1 | |
|---|---|
| Component | CLF-1 |
| Anisole | 19.50 |
| BYK ®-322[1] | 0.020 |

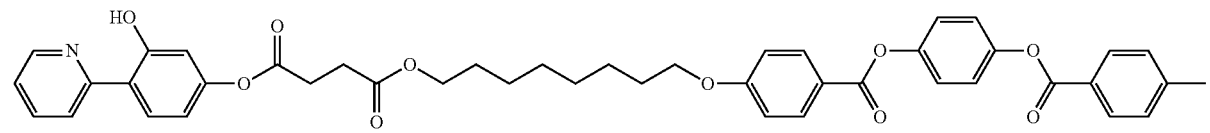 [SMILES: Cc1ccc(C(=O)Oc2ccc(OC(=O)c3ccc(OCCCCCCCCOC(=O)CCC(=O)Oc4ccc(-c5ccccn5)c(O)c4)cc3)cc2)cc1]

Part-B

Part 1—Preparation of the Primer Layer Formulation (PLF).

Into a suitable container equipped with a magnetic stir-bar the following materials were added in the amounts indicated in the following Table 1.

TABLE 1

| Primer Layer Formulation | |
|---|---|
| Component | Amount |
| Polyacrylate polyol[1] | 6.687 g |
| POLYMEG ® 1000[2] | 16.65 g |
| DESMODUR ® PL 340[3] | 21.90 g |

TABLE 2-continued

| Coating Layer Formulation CLF-1 | |
|---|---|
| Component | CLF-1 |
| 4-Methoxyphenol | 0.030 |
| RM257[2] | 12.60 |
| LCM-2[3] | 6.60 |
| LCM-3[4] | 5.40 |
| LCM-4[5] | 5.40 |
| IRGACURE ® 819[6] | 0.45 |

TABLE 2-continued

Coating Layer Formulation CLF-1

| Component | CLF-1 |
|---|---|
| PCDD 1[7] | 1.26 |
| PCDD 2[8] | 2.34 |

[1]An aralkyl modified poly-methyl-alkyl-siloxane available from BYK Chemie, USA.
[2]A liquid crystal monomer 4-(3-acryloyloxypropyloxy)-benzoic acid 2-methyl-1,4-phenylene ester, available commercially from EMD Chemicals, Inc.
[3]1-(6-(6-(6-(6-(6-(6-(6-(8-(4-(4-((1r,1's,4R,4'R)-4'-pentyl-[1,1'-bi(cyclohexane)]-4-carbonyloxy)2- or 3-methylphenyloxycarbonyl)phenoxy)octyloxy)-6-oxohexyloxy)-6-oxohexyloxy)-6-oxohexyloxy)-6-oxohexyloxy)-6-oxohexyloxy)-6-oxohexyloxy)-2-methylprop-2-en-1-one prepared according to procedures described in U.S. Pat. No. 7,910,019B2.
[4]1-(6-(6-(6-(6-(6-(6-(6-(8-(4-(4-(4-(6-acryloyloxyhexyloxy)benzoyloxy)phenoxycarbonyl)phenoxy)octyloxy)-6-oxohexyloxy)-6-oxohexyloxy)-6-oxohexyloxy)-6-oxohexyloxy)-6-oxohexyloxy)-6-oxohexanol, prepared in accordance with Example 17 in U.S. Pat. No. 7,910,019B2.
[5]4-(((1s,4r)-r-pentylcyclohexane-1-carbonyl)oxy)phenyl 4-((6-(acryloyloxy)hexyl)oxy)benzoate.
[6]A photoinitiator available from BASF Corporation.
[7]A photochromic dichroic dye of structure 3,3-bis(4-methoxyphenyl)-6-methoxy-7-(4-(4-(trans,trans-4'-pentyl-[1,1'-bi(cyclohexane)]-4-carbonyloxy)phenyl)piperazin-1-yl)-10,12-di(trifluoromethyl)-13,13-dimethyl-3,13-dihydro-indeno[2',3':3,4]naphtho[1,2-b]pyran prepared according to the procedure of example 44 in U.S. Pat. No. 8,518,546B2.
[8]A photochromic dichroic dye of structure 3-phenyl-3-(4-morpholinophenyl)-10-[4-(4-(4-(trans-4-pentylcyclohexyl)phenyl)benzamido)phenyl]-6-trifluoromethyl-13,13-dimethyl-3,13-dihydro-indeno[2',3':3,4]naphtho[1,2-b]pyran prepared in accordance with Example 33 in U.S. Pat. No. 8,545,984B2.

Additional Coating Layer formulations were prepared by combining CLF-1 with compounds of the Synthesis Examples of PART-A, as summarized in the following Table 3. The components were combined and stirred at 80° C. for one hour to achieve complete dissolution. All quantities are listed as parts by weight in the following Table 3.

TABLE 3

Additional Coating Layer Formulations

| Component | CLF-2 | CLF-3 | CLF-4 |
|---|---|---|---|
| CLF-1 | 100 | 100 | 100 |
| Compound of Example 3 | 0.98 | 2.94 | — |
| Compound of Example 16 | — | — | 1.39 |

Part 4—Preparation of the Topcoat Layer Formulation (TLF).

Into a suitable container equipped with a magnetic stir-bar the following materials were added in the amounts indicated in Table 4 and stirred at room temperature for two hours.

TABLE 4

Topcoat Layer Formulation (TLF).

| Component | Amount |
|---|---|
| Hydroxyethylmethacrylate | 4.97 g |
| Neopentyl glycol diacrylate | 65.45 g |
| DESMODUR ® PL 340[1] | 20.08 g |
| IRGACURE ® 819[2] | 0.25 g |
| Polybutyl Acrylate | 0.50 g |
| SILQUEST ® A-1100[3] | 5.83 g |
| Ethanol, anhydrous | 2.92 g |

[1]A blocked aliphatic polyisocyante available from Covestro AG.
[2]A photoinitiator available from BASF Corporation.
[3]Gamma-Aminopropyltriethoxysilane, available from Momentive Performance Materials.

Part 5—Preparation of the Hard Coat Formulation (HCF).

The HCF was prepared from the ingredients as summarized in Table 5 as follows: Charge 1 was added to a clean dry beaker and placed in an ice bath at 5° C. with stirring. Charge 2 was added resulting in an exotherm to 50° C. The temperature of the resulting reaction mixture was cooled to approximately 20-25° C. and Charge 3 was added with stirring. Charge 4 was added to adjust the pH to 5.5. Charge 5 was added and the solution was mixed for half an hour. The resulting solution was filtered through a 0.45 micron capsule filter and stored at 4° C. until use.

TABLE 5

Hard coat formulation (HCF).

| Component | Amount |
|---|---|
| Charge 1 | |
| Glycidoxypropyltrimethoxysilane | 32.40 g |
| Methyltrimethoxysilane | 345.50 g |
| Charge 2 | |
| Aqueous nitric acid (nitric acid 1 g/7000 g water) | 292.00 g |
| Charge 3 | |
| Propylene glycol monomethyl ether | 228.00 g |
| Charge 4 | |
| 25% Tetramethylammonium hydroxide in methanol | 0.45 g |
| Charge 5 | |
| BYK ®-306[1] | 2.00 g |

[1]A solution of polyether-modified polydimethylsiloxane available from BYK Chemie, USA.

Part 6—Procedures Used for Preparing the Substrate and Coating Stacks Summarized in Table 6.

Corona Treatment

Where indicated below, prior to the application of any of the reported coating layers, the substrate or coated substrate was subject to corona treatment by passing on a conveyor belt in a Tantec EST Systems Power Generator HV 2000 series corona treatment apparatus having a high voltage transformer. The substrates were exposed to corona generated by 70.00 KV and 1000 Watts, while traveling on a conveyor at a belt speed 3 ft/minute (91.4 cm/minute).

Substrate Preparation

Square substrates measuring 5.08 cm by 5.08 cm by 0.318 cm (2 inches (in.) by 2 in. by 0.125 in.) prepared from CR-39® monomer were obtained from Homalite, Inc. Each substrate was cleaned by wiping with a tissue soaked with acetone, dried with a stream of air and corona treated as described above.

Coating Procedure for the Primer Layer

For samples receiving a primer layer, the PLF was applied to the test substrates by spin-coating on a portion of the surface of the test substrate by dispensing approximately 1.5 mL of the solution and spinning the substrates at 975 revolutions per minute (rpm) for 4 seconds, followed by 1500 rpm for 2 seconds followed by 2500 rpm for 1 second yielding a target film thickness of 8 microns. Afterwards, the coated substrates were placed in an oven maintained at 125° C. for 60 minutes, then cooled to room temperature. The coated substrates were then corona treated as described above.

Coating Procedure for the Liquid Crystal Alignment Layer

The LCAF was applied to the test substrates by spin-coating on a portion of the surface of the test substrate by dispensing approximately 1.0 mL of the solution and spinning the substrates at 800 revolutions per minute (rpm) for 3 seconds, followed by 1,000 rpm for 7 seconds, followed by 2,500 rpm for 4 seconds yielding a target film thickness of less than one micron. Afterwards, the coated substrates were placed in an oven maintained at 120° C. for 30 minutes, then cooled to room temperature.

The dried photoalignment layer on each of the substrates was at least partially ordered by exposure to linearly polarized ultraviolet radiation. The light source was oriented such that the radiation was linearly polarized in a plane perpendicular to the surface of the substrate. The amount of ultraviolet radiation that each photoalignment layer was exposed to was measured using a UV POWER PUCK™ High energy radiometer from EIT Inc., and was as follows: UVA 0.018 W/cm$^2$ and 5.361 J/cm$^2$; UVB 0 W/cm$^2$ and 0 J/cm$^2$; UVC 0 W/cm$^2$ and 0 J/cm$^2$; and UW 0.005 W/cm$^2$ and 1.541 J/cm$^2$. After ordering at least a portion of the photo-orientable polymer network, the substrates were cooled to room temperature and kept covered, and were not subject to corona treatment.

Coating Procedure for the Coating Layer

The Coating Layer Formulations, as summarized in Table 6, were applied by spin coating at a rate of 400 revolutions per minute (rpm) for 6 seconds, followed by 800 rpm for 6 seconds onto the at least partially ordered photoalignment materials on the test substrates, yielding a target film thickness of approximately 20 microns. Each coated substrate was placed in an oven at 60-75° C. for 30 minutes. Afterwards they were cured under two ultraviolet lamps in a UV Curing Oven Machine designed and built by Belcan Engineering under a nitrogen atmosphere while moving continuously on a conveyor belt operating at a linear rate of 61 cm/minute (2 ft/minute). The oven operated at peak intensity of 0.388 Watts/cm$^2$ of UVA and 0.165 Watts/cm$^2$ of UVV and UV dosage of 7.386 Joules/cm$^2$ of UVA and 3.337 Joules/cm$^2$ of UVV. Those coated substrates receiving a further topcoat layer were corona treated as described above. Those coated substrates which were not to receive a further topcoat layer were heated at 105° C. for 3 hours.

Coating Procedure for the Topcoat Layer

Where indicated, the TLF was applied by spin coating at a rate of 1,400 revolutions per minute (rpm) for 10 seconds onto the cured CLF coated substrates to yield a target film thickness of approximately 8 microns. Afterwards the substrates were cured under two ultraviolet lamps in the UV Curing Oven Machine designed and built by Belcan Engineering in nitrogen atmosphere while moving continuously on a conveyor belt operating at a linear rate of 183 cm/minute (6 ft/minute). The oven operated at peak intensity of 1.887 Watts/cm$^2$ of UVA and 0.694 Watts/cm$^2$ of UVV and UV dosage of 4.699 Joules/cm$^2$ of UVA and 1.787 Joules/cm$^2$ of UVV. With those coated substrates receiving a further hard coat layer as indicated in Table 6, the UV cured layer was subject to corona treatment as described above. Those coated substrates which were not to receive a further hard coat layer, were heated at 105° C. for 3 hours.

Coating Procedure for the Hard Coat Layer

Where indicated, the HCF was applied by spin coating at a rate of 1,400 revolutions per minute (rpm) for 12 seconds onto the cured topcoat layer coated substrates to yield a target film thickness of two microns. Post curing of the coated substrates was completed at 105° C. for 3 hours.

The coating stacks for the samples prepared as described above are summarized in the following Table 6. In the following Table 6, an "X" in a cell indicates that a particular layer was present in the coating stack, while a blank cell indicates that a particular layer was not present in the coating stack. As summarized in the following Table 6, each coating stack included a "Coating Layer (CLF)" (i.e., CLF-1, or CLF-2, or CLF-3, or CLF-4).

TABLE 6

Coating stacks

| Example | Primer Layer (PLF) | Liquid Crystal Alignment Layer (LCAF) | Coating Layer (CLF) | Topcoat Layer (TLF) | Hard Coat Layer (HCF) |
|---|---|---|---|---|---|
| CE-A |  | X | CLF-1 |  |  |
| CE-B | X | X | CLF-1 |  |  |
| CE-C | X | X | CLF-1 | X |  |
| CE-D | X | X | CLF-1 | X | X |
| E |  | X | CLF-2 |  |  |
| F | X | X | CLF-2 |  |  |
| G | X | X | CLF-2 | X |  |
| H | X | X | CLF-2 | X | X |
| I |  | X | CLF-3 |  |  |
| J | X | X | CLF-3 |  |  |
| K | X | X | CLF-3 | X |  |
| L | X | X | CLF-3 | X | X |
| CE-M |  | X | CLF-1 |  |  |
| CE-N |  | X | CLF-1 | X |  |
| O |  | X | CLF-4 |  |  |
| P |  | X | CLF-4 | X |  |

Part 7—Photochromic Performance Tests Including Absorption Ratio and Optical Response Measurements.

Absorption ratios (AR) for each of the substrates having a coating containing photochromic dichroic dyes (PCDD) were determined as follows. A Cary 6000i UV-Visible spectrophotometer was equipped with a self-centering sample holder mounted on a rotation stage (Model M-060-PD from Polytech, PI) and the appropriate software. A polarizer analyzer (Moxtek PROFLUX® polarizer) was placed in the sample beam before the sample. The instrument was set with the following parameters: Scan speed=600 nm/min; Data interval=1.0 nm; Integration time=100 ms; Absorbance range=0-6.5; Y mode=absorbance; X-mode=nanometers; and the scanning range was 380 to 800 nm. Options were set for 3.5 SBW (slit band width), and double for beam mode. Baseline options were set for Zero/baseline correction. Also, 1.1 and 1.5 (about 2.6 together) Screen Neutral Density filters were in the reference path for all scans. The coated substrate samples were tested in air, at room temperature (22.7° C.±2.4° C.) maintained by the lab air conditioning system.

Orientation of the sample polarizer to be parallel and perpendicular to the analyzer polarizer was accomplished in the following manner. The Cary 6000i was set to 443 nm for samples containing DD-2 and 675 nm for samples containing DD-1, and the absorbance was monitored as the sample was rotated in small increments (0.1 to 5 degrees, e.g., 5, 1, 0.5 and 0.1 degrees). The rotation of the sample was continued until the absorbance was maximized. This position was defined as the perpendicular or 90 degree position. The parallel position was obtained by rotating the stage 90 degrees clock-wise or counter-clockwise. Alignment of the samples was achieved to ±0.10.

The absorption spectra were collected at both 90 and 0 degrees for each sample. Data analysis was handled with the Igor Pro software available from WaveMetrics. The spectra were loaded into Igor Pro and the absorbance values were used to calculate the absorption ratios at 443 nm and 675 nm. The calculated absorption ratios are listed in Table 7.

Prior to response testing on an optical bench, the substrates were conditioned by exposing them to 365 nm ultraviolet light for 10 minutes at a distance of about 14 cm from the source of electromagnetic radiation, in order to pre-activate the photochromic molecules. The UVA irradiance at the sample was measured with a Licor Model Li-1800 spectroradiometer and found to be 22.2 Watts per square meter. The samples were then placed under a halogen lamp (500 W, 120 V) for about 10 minutes at a distance of about 36 cm from the lamp in order to bleach, or inactivate, the photochromic compound in the samples. The illuminance at the sample was measured with the Licor spectroradiometer and found to be 21.9 Klux. The samples were then kept in a dark environment for at least 1 hour prior to testing in order to cool and continue to fade back to a ground state.

An optical bench was used to measure the optical properties of the coated substrates and derive the absorption ratio and photochromic properties. Each test sample was placed on the optical bench with an activating light source (a Newport/Oriel Model 66485 300-Watt Xenon arc lamp fitted with a UNIBLITZ® VS-25 high-speed computer controlled shutter that momentarily closed during data collection so that stray light would not interfere with the data collection process, a SCHOTT® 3 mm KG-1 band-pass filter, which removed short wavelength radiation, neutral density filter(s) for intensity attenuation and a condensing lens for beam collimation) positioned at a 30° to 35° angle of incidence to the surface of the test sample. The arc lamp was equipped with a light intensity controller (Newport/Oriel model 68950).

A broadband light source for monitoring response measurements was positioned in a perpendicular manner to a surface of the test sample. Increased signal of shorter visible wavelengths was obtained by collecting and combining separately filtered light from a 100-Watt tungsten halogen lamp (controlled by a LAMBDA® UP60-14 constant voltage powder supply) with a split-end, bifurcated fiber optical cable. Light from one side of the tungsten halogen lamp was filtered with a SCHOTT® KG1 filter to absorb heat and a HOYA® B-440 filter to allow passage of the shorter wavelengths. The other side of the light was either filtered with a SCHOTT® KG1 filter or unfiltered. The light was collected by focusing light from each side of the lamp onto a separate end of the split-end, bifurcated fiber optic cable, and subsequently combined into one light source emerging from the single end of the cable. A 4 inch (10.2 cm) light pipe was attached to the single end of the cable to insure proper mixing. The broad band light source was fitted with a UNIBLITZ® VS-25 high-speed computer controlled shutter that momentarily opened during data collection.

Polarization of the light source was achieved by passing the light from the single end of the cable through a Moxtek, PROFLUX® Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at 23° C.±0.1° C. maintained by a temperature controlled air cell.

To align each sample, a second polarizer was added to the optical path. The second polarizer was set to 900 of the first polarizer. The sample was placed in an air cell in a self-centering holder mounted on a rotation stage (Model No M-061. PD from Polytech, PI). A laser beam (Coherent-ULN 635 diode laser) was directed through the crossed polarizers and sample. The sample was rotated (in 30 steps as course moves and in 0.10 steps as fine moves) to find the minimum transmission. At this point the sample was aligned either parallel or perpendicular to the Moxtek polarizer and the second polarizer as well as the diode laser beam was removed from the optical path. The sample was aligned ±0.2° prior to any activation.

To conduct the measurements, each test sample was exposed to 6.7 W/m$^2$ of UVA from the activating light source for 10 to 20 minutes to activate the photochromic compound. An International Light Research Radiometer (Model IL-1700) with a detector system (Model SED033 detector, B Filter, and diffuser) was used to verify exposure at the beginning of each day. Light from the monitoring source that was polarized to the 0° polarization plane was then passed through the coated sample and focused into a 1" integrating sphere, which was connected to an OCEAN OPTICS® S2000 spectrophotometer using a single function fiber optic cable. The spectral information, after passing through the sample, was collected using OCEAN OPTICS® OOIBase32 and OOIColor software, and PPG propriety software. While the photochromic material was activated, the position of the polarizing sheet was rotated back and forth to polarize the light from the monitoring light source to the 90° polarization plane and back. Data was collected for approximately 600 to 1200 seconds at 5-second intervals during activation. For each test, rotation of the polarizers was adjusted to collect data in the following sequence of polarization planes: 0°, 90°, 90°, 0°, etc.

Absorption spectra were obtained and analyzed for each test sample using the Igor Pro software (available from WaveMetrics). The change in the absorbance in each polarization direction for each test sample was calculated by subtracting out the 0 time (i.e., unactivated) absorption measurement for the samples at each wavelength tested. Average absorbance values were obtained in the region of the activation profile where the photochromic response of the photochromic compound was saturated or nearly saturated (i.e., the regions where the measured absorbance did not increase or did not increase significantly over time) for each sample by averaging absorbance at each time interval in this region. The average absorbance values in a predetermined range of wavelengths corresponding $\lambda_{max-vis}$+/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the photochromic compound was then calculated by averaging these individual absorption ratios.

Change in optical density ($\Delta$OD) from the bleached state to the darkened state was determined by establishing the initial transmittance, opening the shutter from the xenon lamp to provide ultraviolet radiation to change the test lens from the bleached state to an activated (i.e., darkened) state. Data was collected at selected intervals of time, measuring the transmittance in the activated state, and calculating the change in optical density according to the formula: $\Delta OD=\log(\% Tb/\% Ta)$, where % Tb is the percent transmittance in the bleached state, % Ta is the percent transmittance in the activated state and the logarithm is to the base 10. Measurements were made at the photopic (Phot) wavelength as well as at wavelengths that were an average of 440 nm and 570 nm and are reported in Table 7.

The fade half-life (T½) is the time interval in seconds for the $\Delta$OD of the activated form of the photochromic compounds in the test samples to reach one half the $\Delta$OD measured after fifteen minutes, or after saturation or near-saturation was achieved, at room temperature after removal of the source of activating light, e.g., by closing the shutter.

The results for the Examples according to the present invention and Comparative Examples (CE) of PART-B are summarized in Table 7. The coating stacks for Examples E through L were prepared concurrently with Comparative Examples A through D. The coating stacks of Examples O and P were prepared and tested alongside Comparative Examples M and N.

TABLE 7

Photochromic properties and absorbance ratios of Coating Stacks.

| Example | Phot | ΔOD 440 nm | ΔOD 570 nm | Fade T½ | AR |
|---|---|---|---|---|---|
| CE-A | 0.63 | 0.68 | 0.66 | 226 | 5.83 |
| CE-B | 0.64 | 0.68 | 0.66 | 228 | 5.74 |
| CE-C | 0.63 | 0.67 | 0.65 | 238 | 5.78 |
| CE-D | 0.64 | 0.68 | 0.66 | 233 | 5.61 |
| E | 0.60 | 0.64 | 0.63 | 219 | 6.31 |
| F | 0.60 | 0.65 | 0.63 | 221 | 6.31 |
| G | 0.60 | 0.65 | 0.63 | 218 | 6.21 |
| H | 0.61 | 0.66 | 0.64 | 236 | 6.21 |
| I | 0.57 | 0.61 | 0.59 | 204 | 7.07 |
| J | 0.57 | 0.61 | 0.59 | 211 | 7.07 |
| K | 0.57 | 0.62 | 0.60 | 220 | 6.82 |
| L | 0.58 | 0.62 | 0.60 | 217 | 6.80 |
| CE-M | 0.59 | 0.63 | 0.63 | 239 | 5.84 |
| CE-N | 0.60 | 0.64 | 0.64 | 248 | 5.61 |
| O | 0.59 | 0.61 | 0.62 | 242 | 6.04 |
| P | 0.59 | 0.62 | 0.62 | 247 | 5.78 |

The results summarized in Table 7 demonstrate that coating stacks according to the present invention that include a coating layer (CLF), which includes a compound according to the present invention (CLF-2, CLF-3, or CLF-4) possess improved dichroic properties in the activated state (as indicated by AR values of greater magnitude), as compared to comparative coating stacks that include a coating layer (CLF), which does not include a compound according to the present invention (CLF-1).

The present invention has been described with reference to specific details of particular embodiments thereof. It is not intended that such details be regarded as limitations upon the scope of the invention except insofar as and to the extent that they are included in the accompanying claims.

What is claimed is:

1. A compound represented by at least one of the following Formulas (III), (IV), (V), (VIII), and (IX),

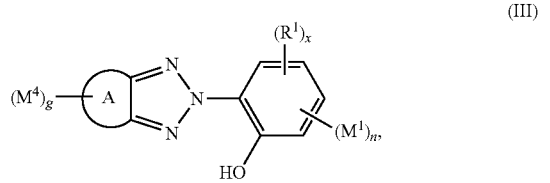

(III)

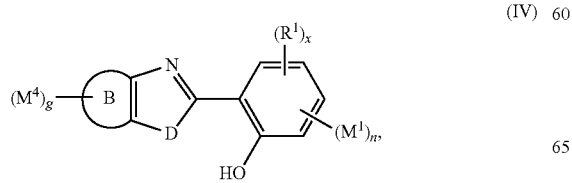

(IV)

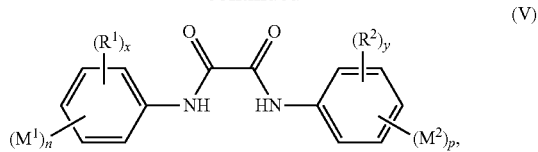

(V)

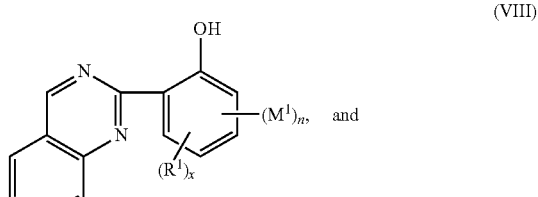

(VIII)

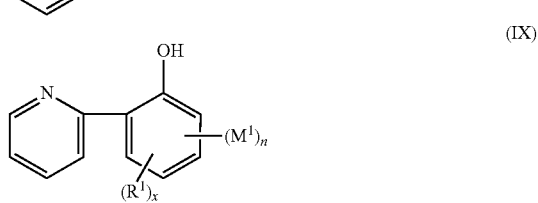

(IX)

wherein independently for each of Formulas (III), (IV), (V), (VIII), and (IX), $R^1$ independently for each x, and $R^2$ independently for each y, are in each case independently selected from the group consisting of hydrogen, hydrocarbyl, substituted hydrocarbyl, and —$OR^7$, where each $R^7$ is independently selected from the group consisting of hydrogen, hydrocarbyl, and substituted hydrocarbyl, wherein the hydrocarbyl and substituted hydrocarbyl of $R^1$, $R^2$, and $R^7$ are in each case independently and optionally interrupted with at least one of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from the group consisting of hydrogen, hydrocarbyl and substituted hydrocarbyl, $M^1$ independently for each n, $M^2$ independently for each p, and $M^4$ independently for each g, are in each case independently represented by the following Formula (X),

(X)

wherein independently for each Formula (X), $L^1$ in each case is independently selected from the group consisting of at least one of: a single bond; —O—; —S—; —C(O)—; —S(O)—; —SO$_2$—; —N=N—; —N($R_{11}$')— where $R_{11}$' is selected from hydrogen, hydrocarbyl or substituted hydrocarbyl; —Si($OR_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl; hydrocarbyl, and substituted hydrocarbyl, each optionally and independently interrupted with at least one of —O—, —S—, —C(O)—, —C(O)O—, —S(O)—, —SO$_2$—, —N=N—, —N($R_{11}$')— where $R_{11}$' is selected from the group consisting of hydrogen, hydrocarbyl or substituted hydrocarbyl, —Si($OR_8$')$_w$($R_8$')$_e$—, where w and e are each independently 0 to 2, provided that the sum of w and e is 2, and each $R_8'$ is independently selected from the group consisting of hydrogen, hydrocarbyl and substituted hydrocarbyl, and combinations of two or more thereof, t is 1 to 4, m is, independently for each t, from 0 to 8, $L^2$ is independently for each m selected from the group consisting of divalent linear or branched $C_1$-$C_{25}$ alkyl, divalent linear or branched $C_1$-$C_{25}$ perhaloalkyl, and divalent linear or branched $C_2$-$C_{25}$ alkenyl, in each case optionally interrupted with at least one of —O—, —S—, —C(O)—, —C(O)O—, —OC(O)O—, —S(O)—, —SO$_2$—, —N(R$^9$)—, and —Si(R$^9$)(R$^{10}$)— wherein $R^9$ and $R^{10}$ are each independently selected from the group consisting of hydrogen, hydrocarbyl and substituted hydrocarbyl, q is, independently for each t, from 0 to 8, provided that the sum of m and q is at least one for each t, and provided that q is at least 1 for at least one t, $L^3$ independently for each q is represented by the following Formula (XI-1),

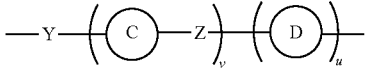

Formula (XI-1)

Y is, independently for each q, a divalent linking group selected from the group consisting of a single bond, —O—, —S—, —C(O)—, —C(O)O—, —OC(O)O—, —S(O)—, —SO$_2$—, —N(R$^9$)—, —N(R$^9$)—C(O)—O—, —C(O)—N(R$^9$)—, and —Si(R$^9$)(R$^{10}$)— wherein $R^9$ and $R^{10}$ are each independently selected from the group consisting of hydrogen, hydrocarbyl and substituted hydrocarbyl, v and u are each independently, for each q, selected from 0 to 5, provided that the sum of v and u is at least 2 for each q that is greater than zero, Z is, independently for each v, a divalent linking group selected from the group consisting of a single bond, —O—, —S—, —C(O)—, —C(O)O—, —OC(O)O—, —S(O)—, —SO$_2$—, —N(R$^9$)—, —N(R$^9$)—C(O)—O—, —C(O)—N(R$^9$)—, and —Si(R$^9$)(R$^{10}$)— wherein $R^9$ and $R^{10}$ are each independently selected from the group consisting of hydrogen, hydrocarbyl and substituted hydrocarbyl, the divalent rings,

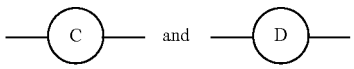

are each independently selected, for each v and each u, from the group consisting of divalent aryl, substituted divalent aryl, divalent heteroaryl, substituted divalent heteroaryl, divalent cycloalkyl, substituted divalent cycloalkyl, divalent heterocycloalkyl, and substituted divalent heterocycloalkyl, $E^1$ is selected from the group consisting of hydrogen, hydrocarbyl, substituted hydrocarbyl each optionally interrupted with at least one of —O—, —S—, —C(O)—, —C(O)O—, —OC(O)O—, —S(O)—, —SO$_2$—, —N(R$^9$)—, and —Si(R$^9$)(R$^{10}$)— wherein $R^9$ and $R^{10}$ are each independently selected from the group consisting of hydrogen, hydrocarbyl and substituted hydrocarbyl, and (meth)acryloyl, provided that a direct $L^1$-$L^2$ link between $L^1$ and $L^2$ is free of two heteroatoms linked together, a direct $L^1$-$L^3$ link between $L^1$ and $L^3$ is free of two heteroatoms linked together, and each direct $L^2$-$L^3$ link between each directly linked $L^2$ and $L^3$ is free of two heteroatoms linked together;

for Formula (III),
x is from 0 to 4,
n is from 0 to 4, provided that the sum of x and n is 4,
g is from 0 to 6, provided that the sum of n and g is at least 1, and
Ring-A is selected from the group consisting of aryl, substituted aryl, heteroaryl, and substituted heteroaryl, for Formula (IV),
x is from 0 to 4,
n is from 1 to 4, provided that the sum of x and n is 4,
g is from 0 to 6, provided that the sum of n and g is at least 1,
Ring-B is selected from the group consisting of aryl, substituted aryl, heteroaryl, and substituted heteroaryl, and
D is selected from the group consisting of O, S, and N—R$_2$', wherein $R_2'$ is selected from the group consisting of hydrogen, hydrocarbyl, and substituted hydrocarbyl, each optionally and independently interrupted with at least one of —O—, —S—, —C(O)—, —C(O)O—, —S(O)—, —SO$_2$—, —N═N—, —N(R$_{11}'$)— where $R_{11}'$ is selected from the group consisting of hydrogen, hydrocarbyl or substituted hydrocarbyl, —Si(OR$_8'$)$_w$(R$_8'$)$_e$—, where w and e are each independently 0 to 2, provided that the sum of w and e is 2, and each $R_8'$ is independently selected from the group consisting of hydrogen, hydrocarbyl and substituted hydrocarbyl, and combinations of two or more thereof, for Formula (V),
x is from 0 to 5,
n is from 0 to 5, provided the sum of x and n is 5,
y is from 0 to 5, and
p is from 0 to 5, provided the sum of y and p is 5, provided that the sum of n and p is at least 1, for Formula (VIII),
x is from 0 to 3, and
n is from 1 to 4, provided that the sum of x and n is 4, for Formula (IX),
x is from 0 to 3, and
n is from 1 to 4, provided that the sum of x and n is 4, wherein at least one $L^3$ independently is a mesogenic group, and said compound is a mesogenic compound.

2. The compound of claim 1 wherein,
independently for each of Formulas (III), (IV), (V), (VIII), and (IX),
$R^1$ independently for each x, and $R^2$ independently for each y, are in each case independently selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, heteroaryl, and —OR$^7$, where each $R^7$ is independently selected from the group consisting of hydrogen, $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl, independently for each Formula (X), and independently for each M¹, independently for each M², and independently for each M⁴, m is at least 1 for at least one t, L², independently for each m, is selected from the group consisting of divalent linear or branched $C_1$-$C_{25}$ alkyl and divalent linear or branched $C_1$-$C_{25}$ perhaloalkyl, in each case optionally interrupted with at least one of —O—, —C(O)O—, and —OC(O)O—, L³, independently for each q, is represented by the following Formula (XI-2),

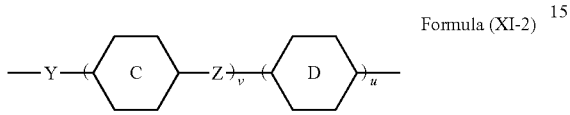

Formula (XI-2)

wherein the divalent rings,

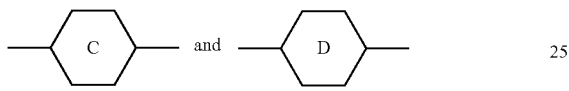

are each independently selected, for each v and each u, from the group consisting of phenylen-1,4-diyl, substituted phenylen-1,4-diyl, cyclohexan-1,4-diyl, substituted cyclohexan-1,4-diyl, pyrimidin-2,5-diyl, substituted pyrimidin-2,5-diyl, pyridine-2,5-diyl, substituted pyridine-2,5-diyl, naphthalene-2,6-diyl, naphthalene-1,4-diyl, substituted naphthalene-2,6-diyl, 1,2,3,4-tetrahydronaphthalene-2,6-diyl, 1,2,3,4-tetrahydronaphthalene-2,6-diyl in which the aromatic ring is substituted, decahydronaphthalene-2,6-diyl, indane-2,5(6)-diyl, fluorene-2,-7-diyl, phenanthrene-2,7-diyl, 9,10-dihydrophenanthrene-2,7-diyl, (1,3,4)thiadiazol-2,5-diyl, (1,3)thiazol-2,5-diyl, (1,3)thiazol-2,4-diyl, thiophen-2,4-diyl, thiophen-2,5-diyl, (1,3)dioxan-2,5-diyl, piperidin-1,4-diyl, and piperazin-1,4-diyl, and E¹ is in each case independently selected from the group consisting of hydrogen, linear or branched $C_1$-$C_{25}$ alkyl, linear or branched $C_2$-$C_{25}$ alkenyl, each optionally interrupted with at least one of —O— and —C(O)O—;

for Formula (III),
Ring-A is aryl or substituted aryl, and for Formula (IV),
Ring-B is aryl or substituted aryl, and
$R_2'$ of D is selected from the group consisting of hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

3. The compound of claim 2 wherein,
independently for each of Formulas (III), (IV), (V), (VIII), and (IX),
$R^1$ independently for each x, and $R^2$ independently for each y, are in each case independently selected from the group consisting of hydrogen, linear or branched $C_1$-$C_{10}$ alkyl, and —OR⁷, where each R⁷ is independently selected from the group consisting of hydrogen, and linear or branched $C_1$-$C_{10}$ alkyl, independently for each Formula (X), and independently for each M¹, independently for each M², and independently for each M⁴, L², independently for each m, is selected from the group consisting of divalent linear or branched $C_1$-$C_{10}$ alkyl and divalent linear or branched $C_1$-$C_{10}$ perfluoroalkyl, in each case optionally interrupted with at least one of —O—, —C(O)O—, and —OC(O)O—, independently for each L³, Z is, independently for each v, selected from the group consisting of a single bond, —O—, and —C(O)O—, and the divalent rings,

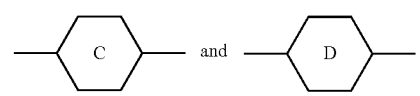

are each independently selected, for each v and each u, from the group consisting of phenylen-1,4-diyl, substituted phenylen-1,4-diyl, cyclohexan-1,4-diyl, and substituted cyclohexan-1,4-diyl, and E¹ is in each case independently selected from the group consisting of hydrogen and linear or branched $C_1$-$C_{10}$ alkyl optionally interrupted with at least one of —O— and —C(O)O—;

for Formula (III),
Ring-A is phenyl, and
g is from 0 to 4, provided that the sum of n and g is at least 1, and for Formula (IV),
Ring-B is phenyl,
$R_2'$ of D is selected from the group consisting of hydrogen and linear or branched $C_1$-$C_{10}$ alkyl, and
g is from 0 to 4, provided that the sum of n and g is at least 1.

4. The compound of claim 1 wherein,
at least one of, divalent Ring-(C) and divalent Ring-(D), are each independently selected from the group consisting of divalent aryl, substituted divalent aryl, divalent heteroaryl, and substituted divalent heteroaryl.

5. The compound of claim 2 wherein,
at least one of, divalent Ring-(C) and divalent Ring-(D), are each independently selected from the group consisting of phenylen-1,4-diyl, substituted phenylen-1,4-diyl, pyrimidin-2,5-diyl, substituted pyrimidin-2,5-diyl, pyridine-2,5-diyl, substituted pyridine-2,5-diyl, naphthalene-2,6-diyl, substituted naphthalene-2,6-diyl, and phenanthrene-2,7-diyl.

6. The compound of claim 3 wherein,
at least one divalent Ring-(C) and at least one divalent Ring-(D) are each independently selected from the group consisting of phenylen-1,4-diyl and substituted phenylen-1,4-diyl.

7. The compound of claim 3 wherein,
for Formula (III),
the sum of n and g is 1,
for Formula (IV),
the sum of n and g is 1,
for Formula (V),
the sum of n and p is 1,
for Formula (VIII),
n is 1, and
for Formula (IX),
n is 1.

8. The compound of claim 3 wherein, each $L^3$ is independently selected from the group consisting of the following formulas,

Formula XI(A)

Formula XI(B)

Formula XI(C)

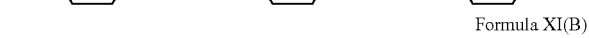

Formula XI(D)

Formula XI(E)

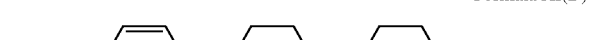

Formula XI(F)

Formula XI(G)

Formula XI(H)

Formula XI(I)

Formula XI(J)

Formula XI(K)

Formula XI(L)

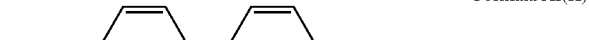

-continued

Formula XI(M)

Formula XI(N)

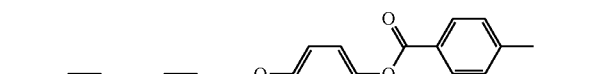

and

Formula XI(O)

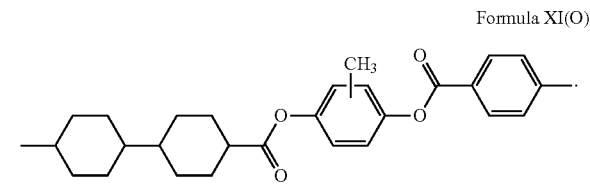

9. The compound of claim 1, wherein said compound is a mesogenic ultraviolet light absorbing compound.

10. A composition comprising said compound of claim 1.

11. The composition of claim 10 further comprising at least one of, (i) a photochromic compound, (ii) a dichroic compound, (iii) a photochromic-dichroic compound, and (iv) a fixed tint.

12. The composition of claim 10 further comprising a liquid crystal material.

13. An article of manufacture comprising said compound of claim 1.

14. The article of manufacture of claim 13, wherein said article of manufacture is an optical element comprising:
an optical substrate; and
a layer over at least a portion of a surface of said optical substrate, wherein said layer comprises said compound of claim 1.

15. The optical element of claim 14, wherein said layer is at least partially aligned by exposing at least a portion of said layer to at least one of, a magnetic field, an electric field, linearly polarized radiation, and shear force.

16. The optical element of claim 14, wherein said layer comprises a liquid crystal phase having at least one of, a nematic phase, a smectic phase, and a chiral nematic phase.

17. The optical element of claim 14, wherein said layer is selected from a primer layer, a protective layer, a photochromic layer, an alignment layer, and an antireflective layer.

18. The optical element of claim 14, further comprising at least one further layer, wherein each further layer is independently selected from a primer layer, a protective layer, a photochromic layer, an alignment layer, and an antireflective layer.

19. The optical element of claim 14, wherein said optical element is selected from the group consisting of an ophthalmic element, a display element, a window, a mirror, and a liquid crystal cell element.

20. The optical element of claim 19, wherein said ophthalmic element is selected from the group consisting of a corrective lens, a non-corrective lens, a contact lens, an intra-ocular lens, a magnifying lens, a protective lens, and a visor.

21. The optical element of claim 14, wherein said layer further comprises a photochromic-dichroic compound, and said layer is a photochromic layer.

22. The optical element of claim 21, wherein said photochromic-dichroic compound comprises a residue of a photochromic compound, wherein said photochromic compound is selected from the group consisting of indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds.

23. The optical element of claim 14, wherein said layer further comprises a fixed tint, and said layer is a dichroic layer.

* * * * *